(12) United States Patent
Neirynck et al.

(10) Patent No.: US 7,993,652 B2
(45) Date of Patent: *Aug. 9, 2011

(54) IMMUNOPROTECTIVE INFLUENZA ANTIGEN AND ITS USE IN VACCINATION

(75) Inventors: Sabine Neirynck, Lokeren (BE); Willy Min Jou, Destelbergen (BE); Walter Fiers, Destelbergen (BE)

(73) Assignee: FVlaams Interuniversitair Instituut Voors Biotechnologie, Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/795,506

(22) Filed: Jun. 7, 2010

(65) Prior Publication Data
US 2010/0297161 A1    Nov. 25, 2010

Related U.S. Application Data

(63) Continuation of application No. 09/498,046, filed on Feb. 4, 2000, now Pat. No. 7,731,972.

(51) Int. Cl.
*A61K 39/00* (2006.01)
*A61K 39/145* (2006.01)

(52) U.S. Cl. .............. 424/192.1; 424/186.1; 424/209.1; 435/69.1

(58) Field of Classification Search .................. None
See application file for complete search history.

(56) References Cited

U.S. PATENT DOCUMENTS

| | | | |
|---|---|---|---|
| 3,919,044 | A | 11/1975 | Melnick et al. |
| 5,691,189 | A | 11/1997 | Kurtz et al. |
| 5,843,446 | A | 12/1998 | Ladd et al. |
| 5,871,747 | A | 2/1999 | Gengoux-Sedlik et al. |
| 6,169,175 | B1 | 1/2001 | Frace et al. |

FOREIGN PATENT DOCUMENTS

| | | |
|---|---|---|
| AU | 49273/90 | 8/1990 |
| WO | WO 92/22575 | 12/1992 |
| WO | WO 94/06472 | 3/1994 |
| WO | WO 98/23735 | 6/1998 |
| WO | WO 99/07839 | 2/1999 |
| WO | WO 01/49886 | 7/2001 |

OTHER PUBLICATIONS

Alford et al., Proc Soc Exp Biol Med. 122(3):800-804 (1966).
Allen et al., "Influenza Virus RNA Segment 7 Has the Coding Capacity for Two Polypeptides", Virology, 107:548-551 (1980).
Arnon, et al., "Synthetic recombinant vaccines against viral agents" Int Arch Allergy Immunol 108(4):321-326 (1995).
Asanuma, et al., "Cross-protection against influenza virus infection in mice vaccinated by combined nasal/subcutaneous administration" Vaccine 1301:3-5 (1995).
Bachmayer, et al., "Potency of influenza vaccines: mouse protection experiments in correlation to field studies in man" Dev. Biol Stand 28:336-339 (1975).
Baez, et al., "Gene composition of high-yielding influenza vaccine strains obtained by recombination" J Infect Dis 141:362-365 (1980).
Bastin, et al., "Use of synthetic peptides of influenza nucleoprotein to define epitopes recognized by class I-restricted cytotoxic T lymphocytes" J Exp. Med. 165:1508-1523 (1987)I.
Bednarek, et al., "The minimum peptide from the influenza-virus matrix protein. Extra and intracellular loading of HLA-A2" J Immunol 147:4047-4053 (1991).
Ben-Ahmeida, et al., "IgG subclass response and protection against challenge following immunisation of mice with various influenza A vaccines" J Med Microbiol 40(4):261-269 (1994).
Berendt, et al., "Evaluation of commercially prepared vaccines for experimentally induced type A/New Jersey/8/76 influenza virus infections in mice and squirrel monkeys" J. Infect Dis 136 Suppl:S712-717(1977).
Betakova, et al., "The NB protein is an integral component of the membrane of influenza B virus" J Gen Virol 77(Pt 11);2689-2694 (1996).
Black, R.A. et al., "Antibody Response to the M2 Protein of Influenza A Virus Expressed in Insect Cells", Journal of General Virology 74:143-146 (1993).
Bodmer, et al., "Enhanced Recognition of a Modified Peptide Antigen by Cytotoxic T Cells Specific for Influenza Nucleoprotein" Cell 52:253-258 (1988).
Borisova et at, "Recombinant Core Particles of Hepatitis B Virus Exposing Foreign Antigenic Determinants on Their Surface," FEBS Letters 259: 121-124 (1989).
Bottex, et al., "Comparative immunogenicity of live influenza viruses and their solubilized neuraminidases: results, of mouse protection experiments" Arch Virol 70(2):83-89 (1981).
Brassard, et al., "Influenza B virus NB glycoprotein is a component of the virion" Virology 220(2): 350-360 (1996).
Brett, et al., "Human T Cell Recognition of Influenza A Nucleoprotein. Specificity and Genetic Restriction of Immunodominant T Helper Cell Epitopes" J Immunol 147:984-991 (1991).
Brown et al., "Foreign Epitopes in Immunodominant Regions of Hepatitis B Core Particles are Highly Immunogenic and Conformationally Restricted," Vaccine 9:595-601 (1991).
Ceppelini, et al., "Binding of labelled influenza matrix peptide to HLA DR in living B lymphoid cells" Nature 339, 392-394 (1989).
Cerundolo, et al., "CD8 independence and specificity of cytotoxic T-lymphocytes restricted by HLA Aw68.1" Proc Roy Soc Lond Series B Biol Sci 244:169-177 (1991).
Charbit et al., "Probing the Topology of a Bacterial Membrane Protein by Genetic Insertion of a Foreign Epitope; Expression at the Cell Surface," EMBO J. 5:3029-3037 (1986).
Charbit et al., "Presentation of Two Epitopes of the preS2 Region of Hepatitis B Virus on Live Recombinant Bacteria", J. Immunol., 139:1658-1664 (1987).
Chen, et al., "Protection against influenza B virus infection by immunization with DNA vaccines" Vaccine 19:1446-1455 (2001).

(Continued)

*Primary Examiner* — Stacy B Chen
(74) *Attorney, Agent, or Firm* — Husch Blackwell LLP

(57) ABSTRACT

The present invention relates to an influenza antigen, comprising a fusion product of at least the extracellular part of a conserved influenza membrane protein or a functional fragment thereof and a presenting carrier, which may be a presenting (poly)peptide or a non-peptidic structure, such as glycans, peptide mimetics, synthetic polymers. The invention further relates to a vaccine against influenza, comprising at least an antigen of the invention, optionally in the presence of one or more excipients. The invention also relates to use of the antigen, a method for preparing the antigen and acceptor cells expressing the antigen.

30 Claims, 35 Drawing Sheets

OTHER PUBLICATIONS

Clarke et al., "Presentation and immunogenicity of Viral Epitopes on the Surface of a Hybrid Hepatitis B Virus Core Particles Produced in Bacteria," J. General Virology 71: 1109-1117 (1990).

Clarke et al, "Improved Immunogenicity of a Peptide Epitope After Fusion to Hepatitis B Core Protein," Nature 330:381-384 (1987).

Cox et al., "Identification of Sequence Changes in the Cold-Adapted, Live Attenuated Influenza Vaccine Strain, A/Ann Arbor/6/60(H2N2)", Virology 167:554-567 (1988).

Cruse, et al., Illustrated Dictionary of Immunology, CRC Press, Boca Raton, pp. 46 and 229 (1995).

Deck, et al., "Characterization of humoral immune responses induced by an influenza hemagglutinin DNA vaccine" Vaccine 15(1):71-78 (1997).

De Filette et al., "Universal influenza A vaccine: optimization of M2-based constructs" Virology. Jun. 20, 337(1):149-161 (2005).

De Filette et al., "The universal influenza vaccine M2e-HBc administered intranasally in combination with the adjuvant CTA1-DD provides complete protection" Vaccine. Jan. 30, 2006a; 24(5):544-551.

De Filette et al., "Improved design and intranasal delivery of an M2e-based human influenza A vaccine" Vaccine. Nov. 10, 2006b; 24(44-46);6597-6601.

De Filette et al., "An influenza A vaccine based on tetrameric ectodomain of matrix protein 2" J Biol Chem. Apr. 25, 2008a; 283(17):11382.

De Filette et al., "Universal influenza A M2e-HBc vaccine protects against disease even in the presence of pre-existing anti-HBc antibodies" Vaccine. Dec. 2, 2008b; 26(51):6503-6507.

de Haan, et al., "Mucosal immunoadjuvant activity of liposomes: induction of systemic IgG and secretory IgA responses in mice by intranasal immunization with an influenza subunit vaccine and coadministered liposomes" Vaccine 13(2):155-162 (1995).

Deroo, et al., "Recombinant neuraminidase vaccine protects against lethal influenza" Vaccine 14(6):561-569 (1996).

de Velasco, et al., "Synthetic peptides representing T-cell epitopes act as carriers in pneumococcal polysaccharide conjugate vaccines" Infect Immun 63(3):961-968 (1995).

DiBrino, et al., "HLA-A1 and HLA-A3 T-cell epitopes derived from influenza-virus proteins predicted from peptide binding motifs" J Immunol 151:5930-5935 (1993).

Dong, et al., "An HLA-B35-restricted epitope modified at an anchor residue results in an antagonist peptide" Eur J Immunol 26:335-339 (1996).

Dorland's Illustrated Dictionary, 1994, 28th ed., Philadelphia; WB Sauders Company, p. 1254.

Dorland's Illustrated Medical Dictionary, 27.sup.th ed., W.B. Saunders Company, Philadelphia, pp. 57, 1746, and 1799 (1988).

Estabrook, et al., "Monoclonal antibodies: their importance to surgeons" J. Invest. Surg. 2(3): 211-222 (1989) abstract only.

Eliasson et al., "CTA1-M2e-DD: a novel mucosal adjuvant targeted influenza vaccine" Vaccine. Feb. 26, 2008; 26(9):1243-1252.

Ernst et al., "Protection against H1, H5, H6 and H9 influenza A infection with liposomal matrix 2 epitope vaccines" Vaccine. Jun. 12, 2006; 24(24):5158.

Fan et al., "Preclinical study of influenza virus A M2 peptide conjugate vaccines in mice, ferrets, and rhesus monkeys" Vaccine. Aug. 13, 2004; 22(23-24):2993-3003.

Fields, et al., Virology 3rd ed., 1996, Philadelphia; Lippencott, Williams, and Wilkins, pp. 1400 and 1417.

Fields, Virology 4th ed., p. 1541 (2001).

Fiers et al., "Soluble recombinant influenza vaccines" Philos Trans R Soc Lond B Biol Sci. Dec. 29, 2001; 356(1416):1961.

Fiers et al., "A universal human influenza A vaccine" Virus Res. Jul. 2004; 103(1-2):173-176.

Francis et al., "Peptide Vaccines Based on Enhanced Immunogenicity of Peptide Epitopes Presented with T-Cell Determinants or Hepatitis B Core Protein," In: Antibodies, Antigens, and Molecular Mimicry, Methods in Enzymology vol. 178, J.J. Lagone, editor, pp. 659-676, Academic Press, Inc., New York (1989).

Francis et al, "Immunological Properties of Hepatitis B Core Antigen Fusion Proteins," Proc. Natl. Acad. Sci. 87:2545-2549 (1990).

Friede, et al., "Selective induction of protection against influenza virus infection in mice by a lipid-peptide conjugate delivered in liposomes" Vaccine 12(9):791-797 (1994).

Fundamental Immunology, Third ed., W. E. Paul editor, Raven Press, New York, pp. 1311-1312 (1993).

Gao, et al., "Identification and Characterization of T Helper Epitopes in the Nucleoprotein of Influenza A virus" J Immunol 143:3007-3014 (1989).

Gao, "Priming of influenza virus-specific cytotoxic T lymphocytes vivo by short synthetic peptides" J Immunol 147:3268-3273 (1991).

Gerhard et al., "Prospects for universal influenza virus vaccine", Emerging Infectious Diseases, 12(4):569-574 (Apr. 2006).

Ghazi, et al., "Comparative antibody responses and protection in mice immunised by oral or parenteral routes with influenza virus subunit antigens in aqueous form or incorporated into ISCOMs" J Med Microbiol 42(1):53-61 (1995).

Ghazi, et al., "Immunogenicity of influenza and HSV-1 mixed antigen ISCOMs in mice" Arch Virol 140(6):1015-1031 (1995).

Gotch, et al., "Cytotoxic T lymphocytes recognize a fragment of influenza virus matrix protein in association with HLA-A2" Nature 326:881-882 (1987).

Govorkova, et al., "Cross-protection of mice immunized with different influenza A (H2) strains and challenged with viruses of the same HA subtype" Acta Virol 41(5):251-257 (1997).

Gray, et al., "pH-induced conformational changes of membrane-bound influenza hemagglutinin and its effect on target lipid bilayers" Protein Science 7(11):2359-2373 (1998) abstract only.

Hay, "Functional Properties of the Virus Ion Channels" Textbook of Influenza 7:74-81 (1998).

Heinen et al., "Vaccination of pigs with a DNA construct expressing an influenza virus M2-nucleoprotein fusion protein exacerbates disease after challenge with influenza A virus" J Gen Virol. Aug. 2002; 83(Pt 8):1851-1859.

Hirabayashi, et al., "Comparison of intranasal inoculation of influenza HA vaccine combined with cholera toxin B subunit with oral or parenteral vaccination" Vaccine 8(3):243-248 (1990).

Hjorth, et al., "The effect of syntex adjuvant formulation (SAF-m) on humoral immunity to the influenza virus in the mouse" Vaccine 15(5):541-546 (1997).

Hongo, et al., "Identification of a second protein encoded by influenza C virus RNA segment 6" J Gen Virol 75(Pt12):3503-3510 (1994).

Hongo, et al., "Characterization of a second protein (CM2) encoded by RNA segment 6 of influenza C virus" J Virol 71(4):2786-2792 (1997).

Huleatt et al., "Potent immunogenicity and efficacy of a universal influenza vaccine candidate comprising a recombinant fusion protein linking influenza M2e to the TLR5 ligand flagellin" Vaccine 2007 25(42):7313-7321.

Ionescu et al., "Pharmaceutical and Immunological Evaluation of Human Papillomavirus Viruslike Particle as an Antigen Carrier" J. Pharm. Sci. Jan. 2006; 95(1):70-79.

Jegerlehner, et al., "Influenza a Vaccine Based on the Extracellular Domain of M2: Weak protection Mediated via Antibody-Dependent NK Cell Activity" Journal of Immunology 172:5598-5605 (2004).

Jemski, et al., "Aerosol vaccination with a live, temperature-sensitive recombinant influenza virus" Infect Immun 13(3):818-824 (1976).

Justewicz, et al., "Antibody-forming cell response to virus challenge in mice immunized with DNA encoding the influenza virus hemagglutinin" J Virol 69(12):7712-7717 (1995).

Justewicz, et al., "Long-term maintenance of B cell immunity to influenza virus hemagglutinin in mice following DNA-based immunization" Virology 2224(1):10-17 (1996).

Katz et al., "Immune Mechanisms of Protection Induced by Vaccination of BALB/c Mice with Influenza A Virus M2 Protein," In, Options for the Control of Influenza III, Leo Brown, et al. (eds.), pp. 837-843 Elsevier, B.V., (1996).

Katz, et al., "Adjuvant activity of the heat-labile enterotoxin from enterotoxigenic *Escherichia coli* for oral administration of inactivated influenza virus vaccine" J Infect Dis 175(2):352-363 (1997).

Kikuta, et al., "Cross-protection against influenza B type virus infection by intranasal inoculation of the HA vaccines combined with cholera toxin B subunit" Vaccine 8(6):595-599 (1990).

Kilbourne, et al., "Purified influenza A virus N2 neuraminidase vaccine is immunogenic and non-toxic in humans" Vaccine 13(18):1799-1803 (1995).

Kitikoon et al., "Matrix 2 Protein Contributes to Protection Against Different H1 Swine Influenza Isolates", 5th International Symposium on Emerging and Re-emerging Pig Diseases, Karakow, Poland Jun. 24-27, 2007.

Neirynck et al., "A universal influenza A vaccine based on the extracellular domain of the M2 protein" Nature Medicine, Oct., 5(10):1157-1163 (1999).

Oukka, et al., "Protection against lethal viral infection by vaccination with nonimmunodominant peptides" J Immunol 157(7):3039-3045 (1996).

Parker, et al., "Influenza A virus. A model for viral antigen presentation to cytotoxic T lymphocytes" Seminars in Virology 7:61-73 (1996).

Pang, et al. "A novel particulate influenza vaccine induces long-term and broad-base immunity in mice after oral immunization" J Virol 66(2):1162-1170 (1992).

Parkin, et al., "Genetically engineered live attenuated influenza A virus vaccine candidates" J Virol 71(4):2772-2778 (1997).

Parks et al., "Transposition of domains between the M2 and HN viral membrane proteins results in polypeptides which can adopt more than one membrane orientation" J. Cell Biol., 109:2023-2032 (1989).

Pekosz, et al., "The CM2 protein of influenza C virus is an oligomeric integral membrane glycoprotein structurally analogous to influenza A virus M2 and influenza B virus NB proteins" Virology 237(2):439451 (1997).

Piard, J Bacteriol., 179:3068-3072 (1997).

Potter, et al., "Immune response of mice to immunization with subunit influenza A vaccine in DTP vaccine" Vacine 13(3):253-260 (1995).

Pouwels, et al., "The Potential of Lactobacillus As a Carrier for Oral Immunization: Development and Preliminary Characterization of Vector Systems for Targeted Delivery of Antigens" The Journal of Biotechnology. 44:183-192 (1996).

Pumpens et al., "Hepatitis B Virus Core Particles as Epitope Carriers," Intervirology 38:63-74 (1995).

Reichert, et al., "Effect of neuraminidase on potency of inactivated influenza virus vaccines in mice" Dev Biol Stand 28:319-323 (1995).

Renegar, "Influenza virus infections and immunity: a review of human and animal models" Lab Anim Sci 42(3):222-232 (1992).

Ripka, et al., "Peptidomimetic design" Curr Opin Chem Biol 2(4):441-452 (1998).

Rota, et al., "Comparison of inactivated, live and recombinant DNA vaccines against influenza virus in a mouse model" Virus Res 16(1):83-93 (1990).

Rotzschke, et al., "Isolation and analysis of naturally processed viral peptides as recognized by cytotoxic T-cells" Nature 348:252-254 (1990).

Sansom, et al., "Influenza Virus M.sub.2 Protein: A Molecular Modelling Study of the Ion Channel" Protein Engineering 6:65-74. (1993).

Shapira, et al., "A synthetic vaccine against influenza with built-in adjuvanticity" Int J Immunopharmacol 7(5):719-723 (1985).

Simeckova-Rosenberg, et al., "Protection of mice against lethal viral infection by synthetic peptides corresponding to B- and T-cell recognition sites of influenza A hemagglutinin" Vaccine 13(10):927-932 (1995).

Slepushkin, et al., "Protection of mice against influenza A virus challenge by vaccination with baculovirus-expressed M2 protein" Vaccine 13(15)1399-1402 (1995).

Sunstrom, et al., "Ion channels formed by NB, an influenza B virus protein" J Membr Biol 150(2)127-132 (1996).

Sweetser, et al., "Recognition of preprocessed endogenous antigen by class I but not class II MHC-restricted T cells" Nature 342:180-182 (1989).

Tamura, et al. "Cross-protection against influenza virus infection afforded by trivalent inactivated vaccines inoculated intranasally with cholera toxin B subunit" J Immunol; 149(3): 981-988(1992).

Tamura, et al., "*Escherichia coli* heat-labile enterotoxin B subunits supplemented with a trace amount of the holotoxin as an adjuvant for nasal influenza vaccine" Vaccine 12(12):1083-1089 (1994).

Tamura, et al., "Formulation of inactivated influenza vaccines for providing effective cross-protection by intranasal vaccination in mice" Vaccine 12(4):310-316 (1994).

Taylor et al., (2009) In Abstract book of "The Twelfth Annual Conference on Vaccine Research", Baltimore, Apr. 2009, p. 130, S10.

Thimme, et al., "Mx1 but Not MxA Confers Resistance against Tick-Borne Dhri Virus in Mice", Virology 211:296-301 (1995).

Tosteson, et al., "Reconstitution of the Influenza Virus M.sub.2 Ion Channel in Lipid Bilayers", The Journal of Membrane Biology 142:117-126 (1994).

Townsend, et al., "The epitopes of influenza nucleoprotein recognized by cytotoxic T lymphocytes can be defined with short synthetic peptides" Cell 44, 959-968 (1986).

Treanor et al., "Passively Transferred Monoclonal Antibody to the M2 Protein Inhibits Influenza A Virus Replication in Mice," Journal of D5 Virology, 64(3):1375-1377 (1990).

Uger, et al., "Creating CTL targets with epitope-linked b2-microglobulin constructs" J Immunol 160:1598-1605 (1998).

Ulmer, et al., "Protective immunity by intramuscular injection of low doses of influenza virus DNA vaccines" Vaccine 12(16):1541-1544 (1994).

Ulrich, "Core Particles of Hepatitis B Virus as Carrier for Foreign Epitopes", Advances in Virus Research 50:141-182 (1998).

Verhoeyen, et al., "Antigenic drift between the haemagglutinin of the Hong Kong influenza strains A/Aichi/2/68 and A/Victoria/3/75" Nature 286:771-775 (1980).

von Brunn et al., "Principal Neutralizing Domain of HIV-1 is Highly Immunogenic when Expressed on the Surface of Hepatitis B Core Particles," Vaccine 11:817-824 (1993).

Waldman, et al., "Age-dependent antibody response in mice and humans following oral influenza immunization" J Clin Immunol 7(4):327-332.(1987).

Webster, et al., "Efficacy of equine influenza vaccines for protection against A/Equine/Jilin/89 (H3N8)—a new equine influenza virus" Vaccine 11(10):987-993 (1993).

Wells et al. "*Lactococcus lactis*: High-level Expression of Tetanus Toxin Fragment C and Protection Against Lethal Challenge", Molecular Microbiology, 8(6):1155-1162 (1993).

Williams, et al., "Determination of the orientation of an integral membrane protein and sites of glycosylation by oligonucleotide-directed mutagenesis: influenza B virus NB glycoprotein lacks a cleavable signal sequence and has an extracellular NH2-terminal region" Mol. Cell. Biol. 6:4317-4328 (1986).

Wu et al., "Characterization of immunity induced by M2e of influenza virus" Vaccine 2007 25(52):8868-8873.

Zebedee et al., "Characterization of the Influenza Virus M2 Integral Membrane Protein and Expression at the Infected-Cell Surface from Cloned cDNA," J. Virology 56:502-511 (1985).

Zebedee, et al., "Influenza A virus M2 protein: monoclonal antibody restriction of virus growth and detection of M2 in virions" Journal of Virology 62(8):2762-2772 (1988).

Zharikova, et al., "Influenza type A virus escape mutants emerge in vivo in the presence of antibodies to the ectodomain of matrix protein 2" Journal of Virology 79(11):6644-6654 (2005).

Zou et al., "The epitope recognized by a monoclonal antibody in influenza A virus M2 protein is immunogenic and confers immune protection" Int Immunopharmacol. Apr. 2005: 5(4):631-5.

Opposition Letter dated Sep. 4, 2006 to European Patent No. EP 0 996 717 B1.

Notice of Opposition to European Patent No. EP 0 996 717 B1 dated Sep. 5, 2006.

Opposition Letter dated Sep. 5, 2006 to European Patent No. EP 0 996 717 B1.

Opposition Letter dated Sep. 7, 2006 to European Patent No. EP 0 996 717 B1.

(English version) Insertie Van Nucleoproteine T-Cel Epitoop Van Het Influenza A Virus in Het M2-Hepatitis B Core Fusie-Eiwit, by Bart Bamps, Promotor: Professor Willy Min Jou, Begeleider: Sabine Neirynck, Laboratorium voor Moleculaire Biologie VIB, Universiteit GENT, Academiejaar 1996-1997, Academic Degree obtained Jul. 2, 1997.

(English version) Een Expressieplasmide Leidend Tot De Presentatie Van Influenza M2 Eiwitepitopen Op Het *E. coli* Celoppeervlak, by Sabine Neirynck, Promotor: Professor W. Fiers, Laboratorium voor Moleculaire Biologie VIB, Rijksuniversiteit GENT, Academiejarr 1987-1988, Academic Degree obtained Sep. 30, 1988.

Acambis, plc. Press release Jan. 3, 2008.

Clinical Trial dated Jul. 6, 2009.

Kodihalli, et al., "Cross-protection among lethal H5N2 influenza viruses induced by DNA vaccine to the hemagglutinin" J Virol 71(5):3391-3396 (1997).

Kovacsovics-Banowski et al., "Efficient Major Histocompatibility Complex Class I Presentation of Exogenous Antigen Upon Phagocytosis by Macrophages" Proc. Natl. Acad. Sci., 90:4942-4946 (1993).

Lamb, et al., "Influenza Virus M.sub.2 Protein is an Integral Membrane Protein Expressed on the Infected-Cell Surface" Cell 40:627-633 (1985).

Levi, et al., "Intranasal immunization of mice against influenza with synthetic peptides anchored to proteosomes" Vaccine 13(14):1353-1359 (1995).

Levi, et al., "Synthetic recombinant influenza vaccine induces efficient long-term immunity and cross-strain protection" Vaccine 14(1):85-92 (1996).

Liu, et al., "N-terminus of M2 protein could induce antibodies with inhibitory activity against influenza virus replication", FEMS Immunology and Medical Microbiology 35:141-146(2003).

Liu, et al., "High epitope density in a single recombinant protein molecule of the extracellular domain of influenza A virus M2 protein significantly enhances protective immunity" Vaccine 23:366-371 (2004).

Lovgren, et al., "An experimental influenza subunit vaccine (iscom): induction of protective immunity to challenge infection in mice after intranasal or subcutaneous administration" Clin Exp Immunol 82(3):435439 (1990).

Masihi, et al., "Effects of mycobacterial fractions and muramyl dipeptide on the resistance of mice to aerogenic influenza virus infection" Int J Immunopharmacol 5(5):403-410 (1983).

Masihi, et al., "Effect of immunomodulator adamantylamide dipeptide on antibody response to influenza subunit vaccines and protection against aerosol influenza infection" Vaccine 8(2):159163 (1990).

Mbawuike, et al., "Vaccination with inactivated influenza A virus during pregnancy protects neonatal mice against lethal challenge by influenza A viruses representing three subtypes" J Virol 64(3):1370-1374 (1990).

Mbawuike, et al., "Enhancement of the protective efficacy of inactivated influenza A virus vaccine in aged mice by IL-2 liposomes" Vaccine 8(4):347-352 (1990).

Mbawuike, et al., "Influenza A subtype cross-protection after immunization of outbred mice with a purified chimeric NS1/HA2 influenza virus protein" Vaccine 12(14):1340-1348 (1994).

McEwen, J. et al. (1992), "Synthetic Recombinant Vaccine Expressing Influenza Haemagglutinin Epitope, in *Salmonella flagellin* Leads to Partial Protection in Mice" Vaccine, 10(6):405-411 (1992).

McMichael, et al., "HLA B37 determines an influenza A virus nucleoprotein epitope recognized by human cytotoxic T lymphocytes" J Exp. Med. 164:1397-1406 (1986).

Meitin, et al., "Enteric immunization of mice against influenza with recombinant vaccinia" Proc Nat's Acad Sci USA 91(23):11187-11191 (1994).

Milich et al., "The Hepatitis Nucleocapsid as a Vaccine Carrier Moiety", An NY Acad Sci. 754: 187-201 (1995).

Milligan, et al., "The recognition of a viral antigenic moiety by class I MHC-Restricted Cytolytic T Lymphocytes is limited by the availability of the endogenously processed antigen" J Immunol 145:3188-3193 (1990).

Monto, et al., "Clinical Signs and symptoms Predicting Influenza Infection" Archive of Internal Medicine 160:3243-3247 (2000).

Moore, "Designing peptide mimetics" Trends Pharmacol Sci 15(4):124-129.

Mozdzanowska, et al., "Induction of influenza type A virus-specific resistance by immunization of mice with a synthetic multiple antigenic peptide vaccine that contains ectodomains of matrix protein 2" Vaccine 21:2616-2626 (2003).

Figure 1
A
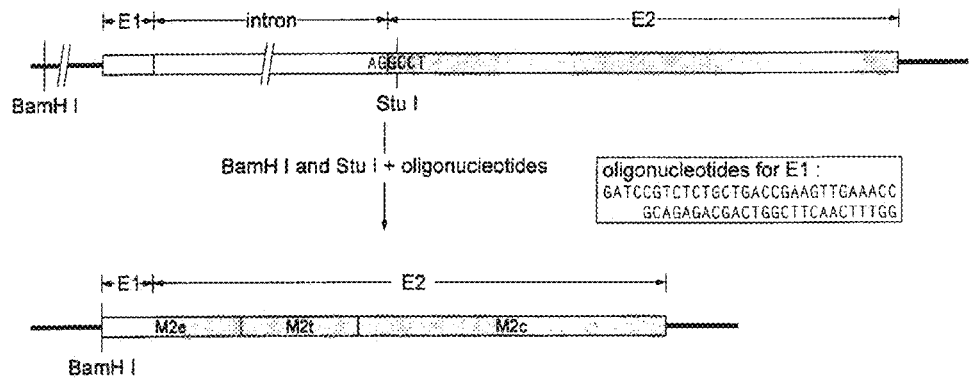
B
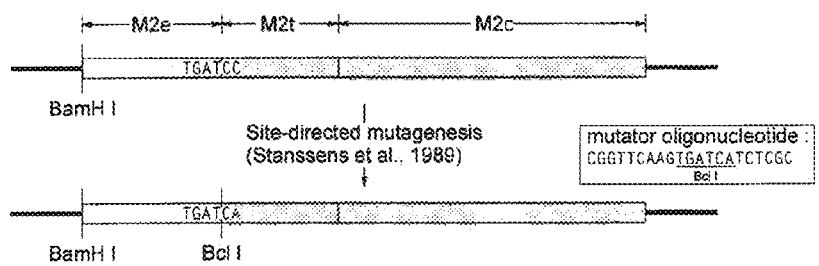
C
|  | 2 | 3 | 4 | 5 | 6 | 7 | 8 | 9 | 10 | 11 |
|---|---|---|---|---|---|---|---|---|---|---|
| Nucleotide sequence: | TCT | CTG | CTG | ACC | GAA | GTT | GAA | ACC | CCT | ATC |
| Amino acid sequence: | Ser | Leu | Leu | Thr | Glu | Val | Glu | Thr | Pro | Ile |
| 12 | 13 | 14 | 15 | 16 | 17 | 18 | 19 | 20 | 21 | 22 | 23 | 24 |
|---|---|---|---|---|---|---|---|---|---|---|---|---|
| AGA | AAC | GAA | TGG | GGG | TGC | AGA | TGC | AAC | GGT | TCA | AGT | GAT |
| Arg | Asn | Glu | Trp | Gly | Cys | Arg | Cys | Asn | Gly | Ser | Ser | Asp |

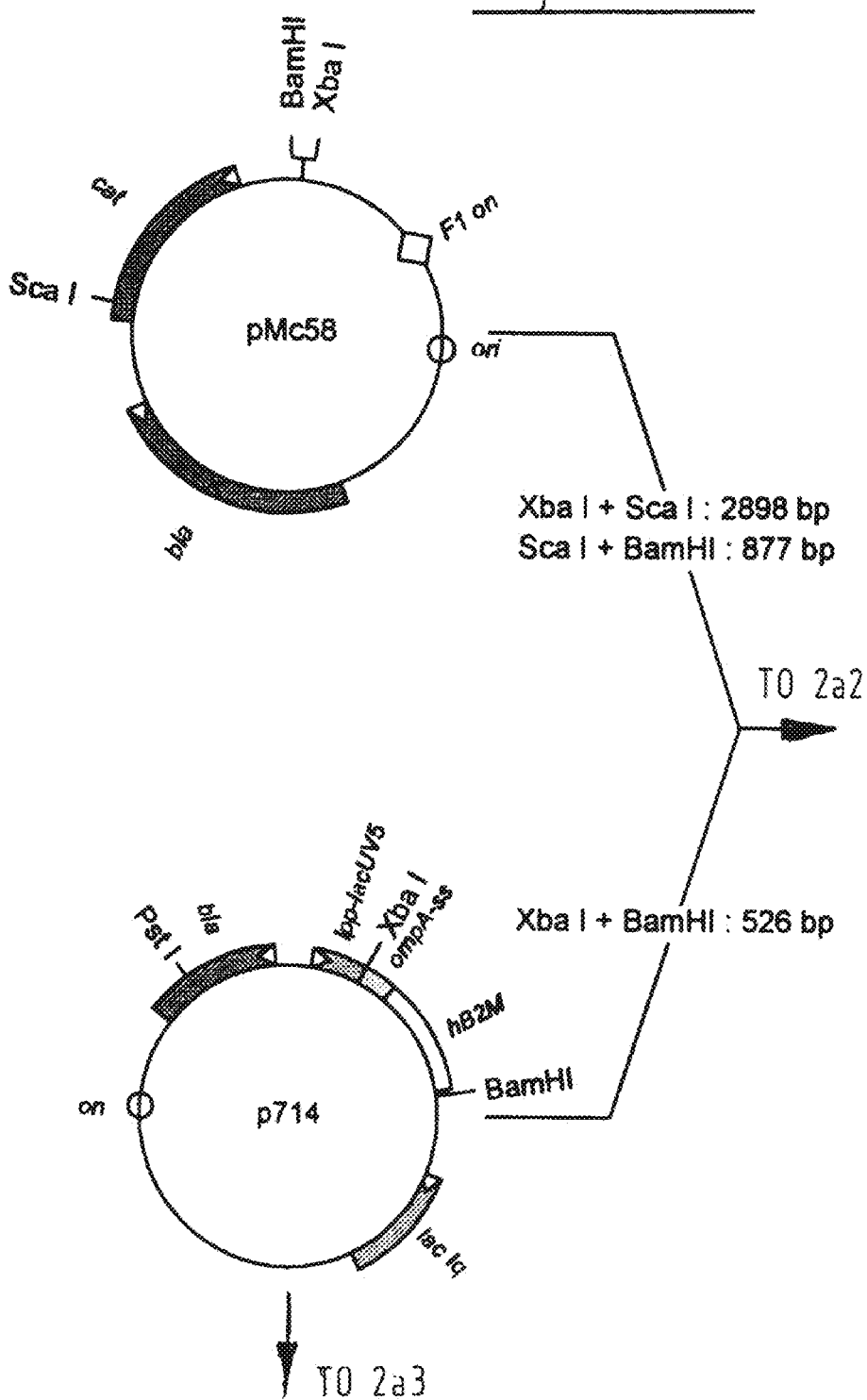

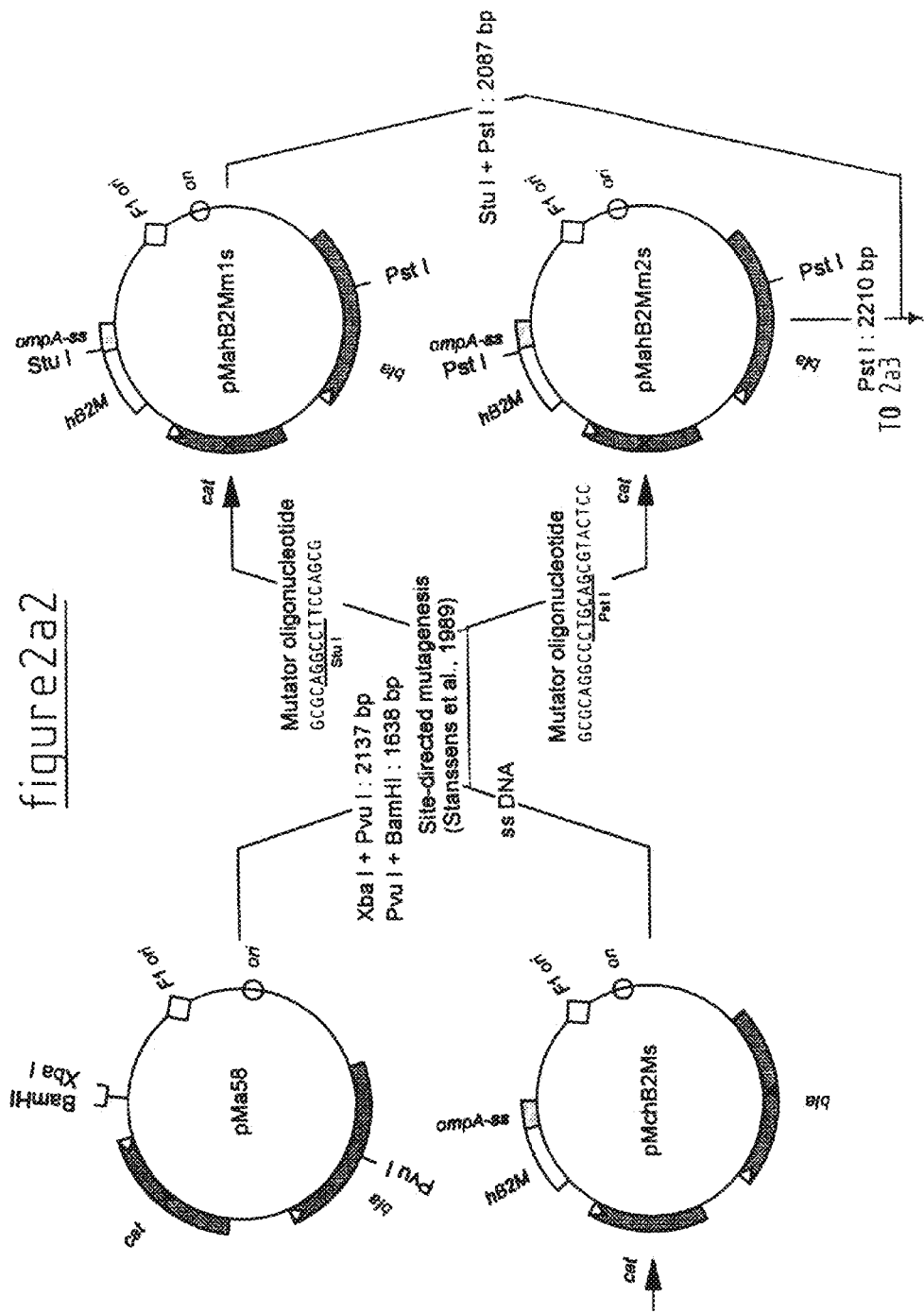

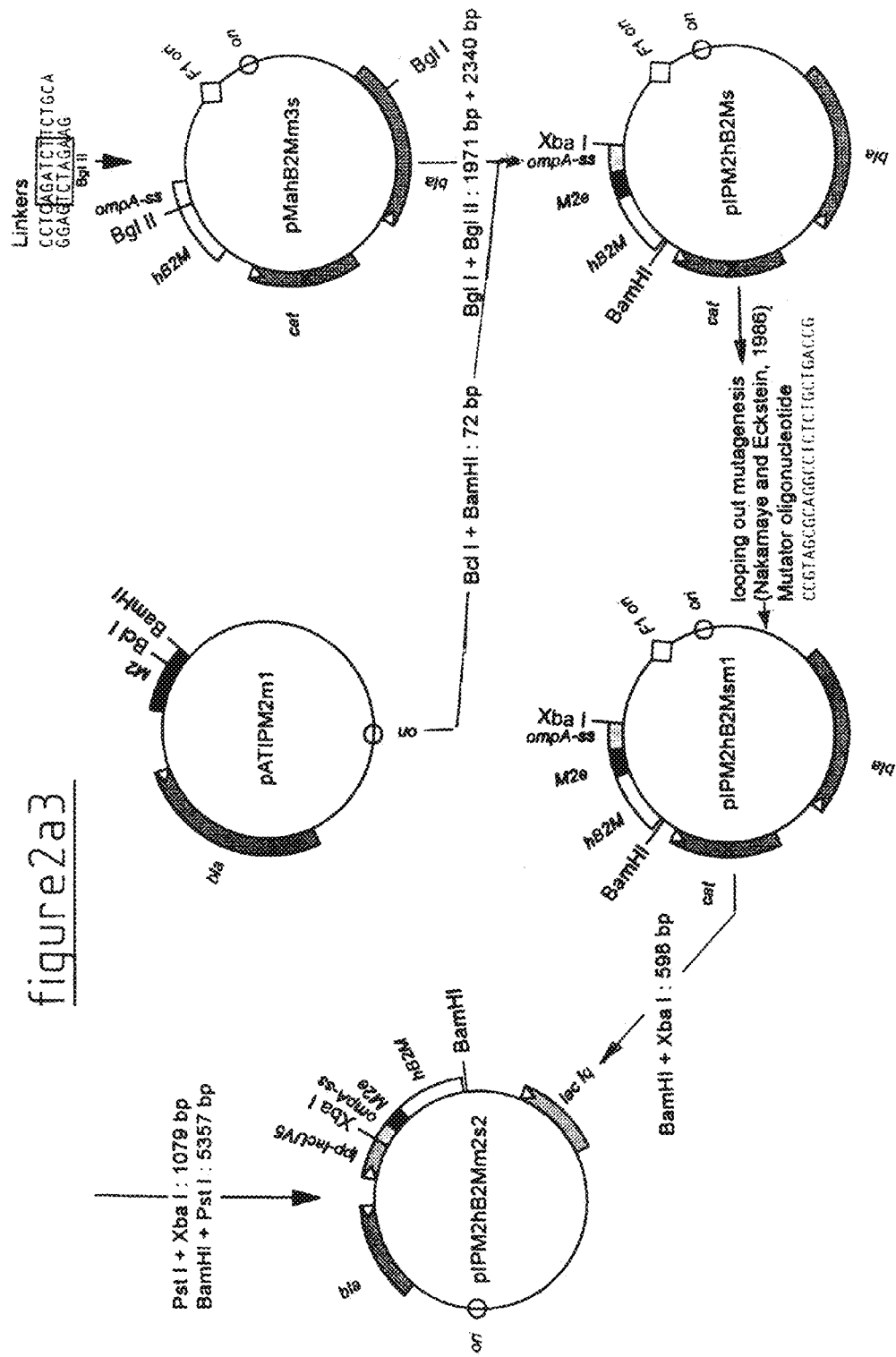

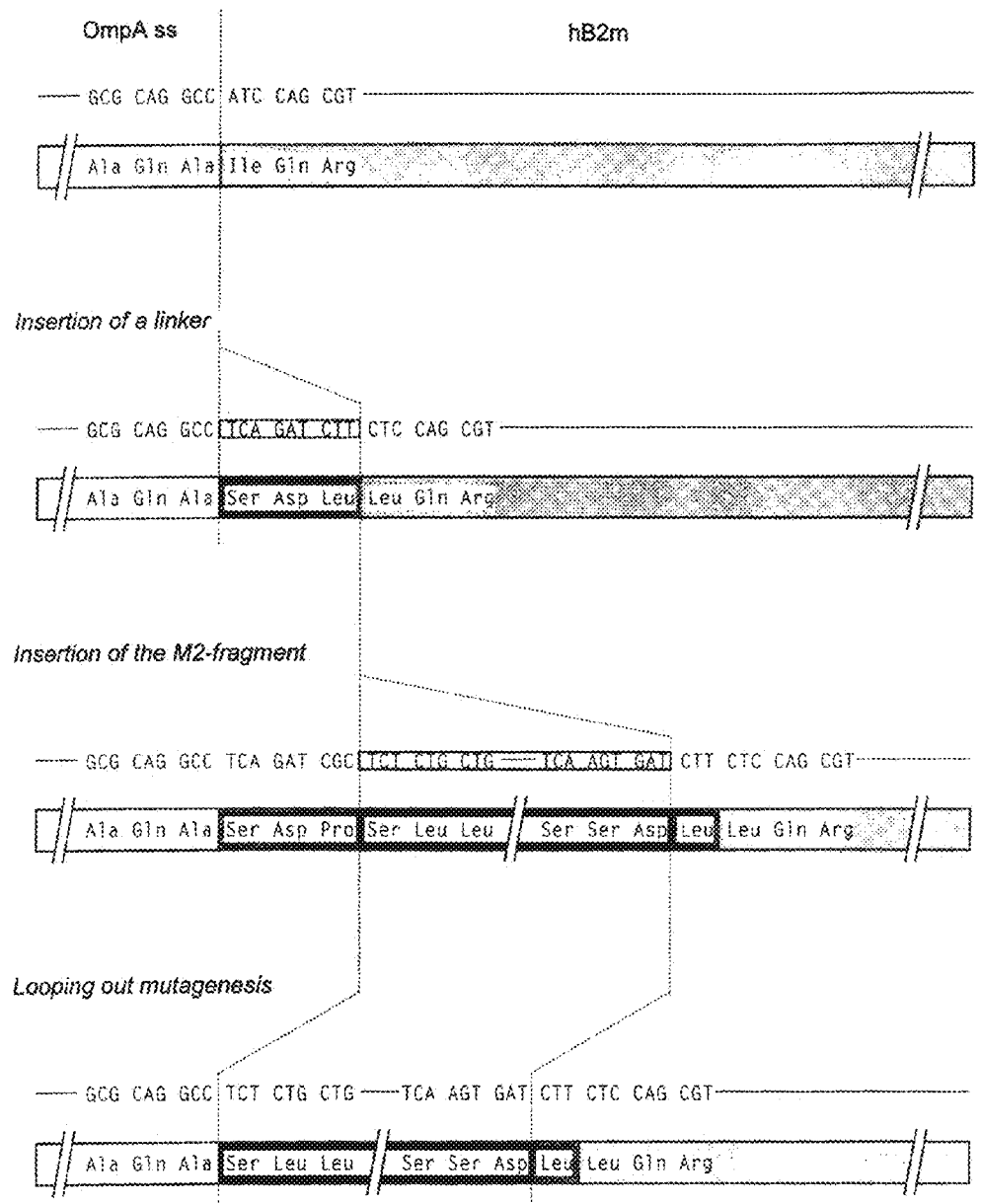

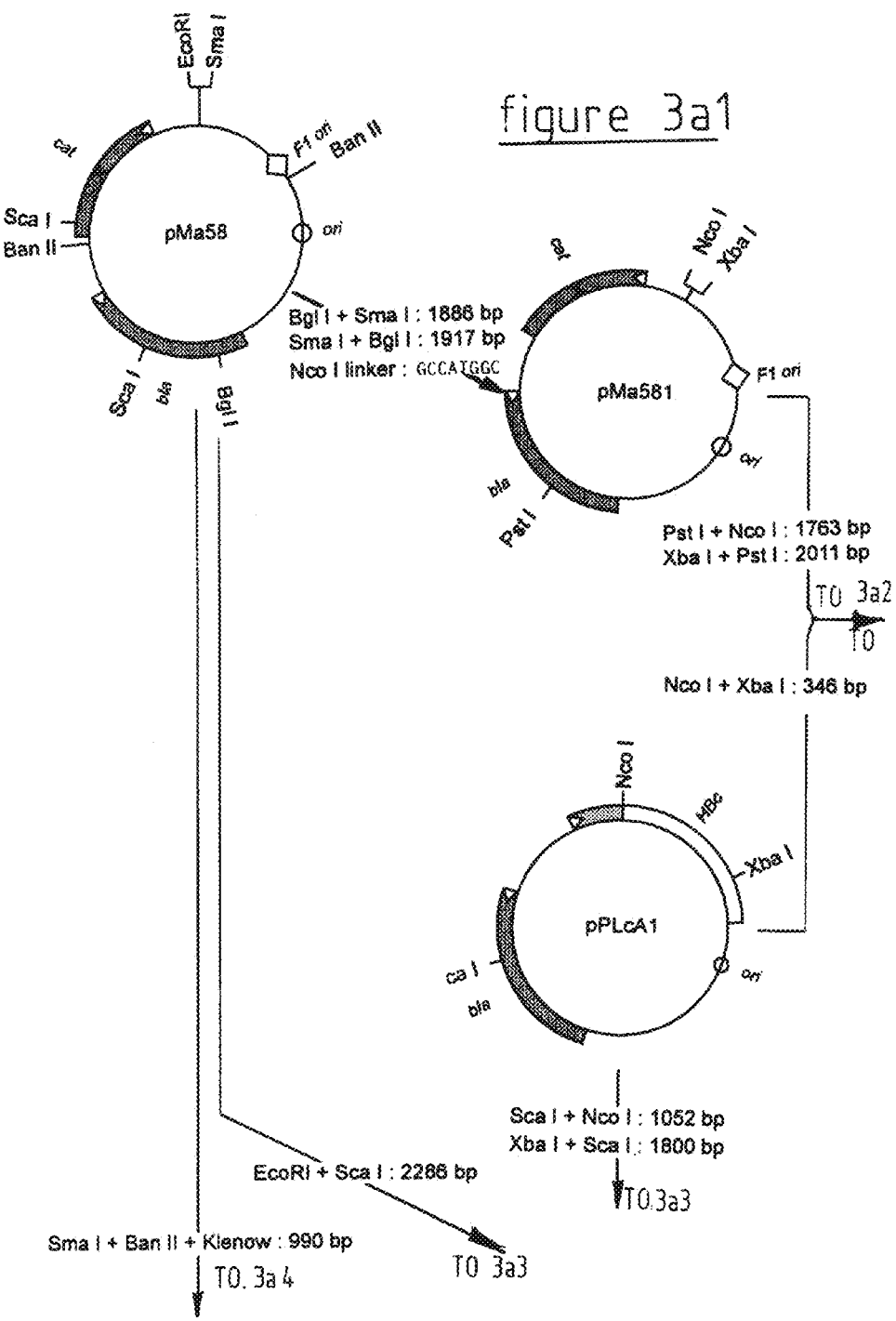

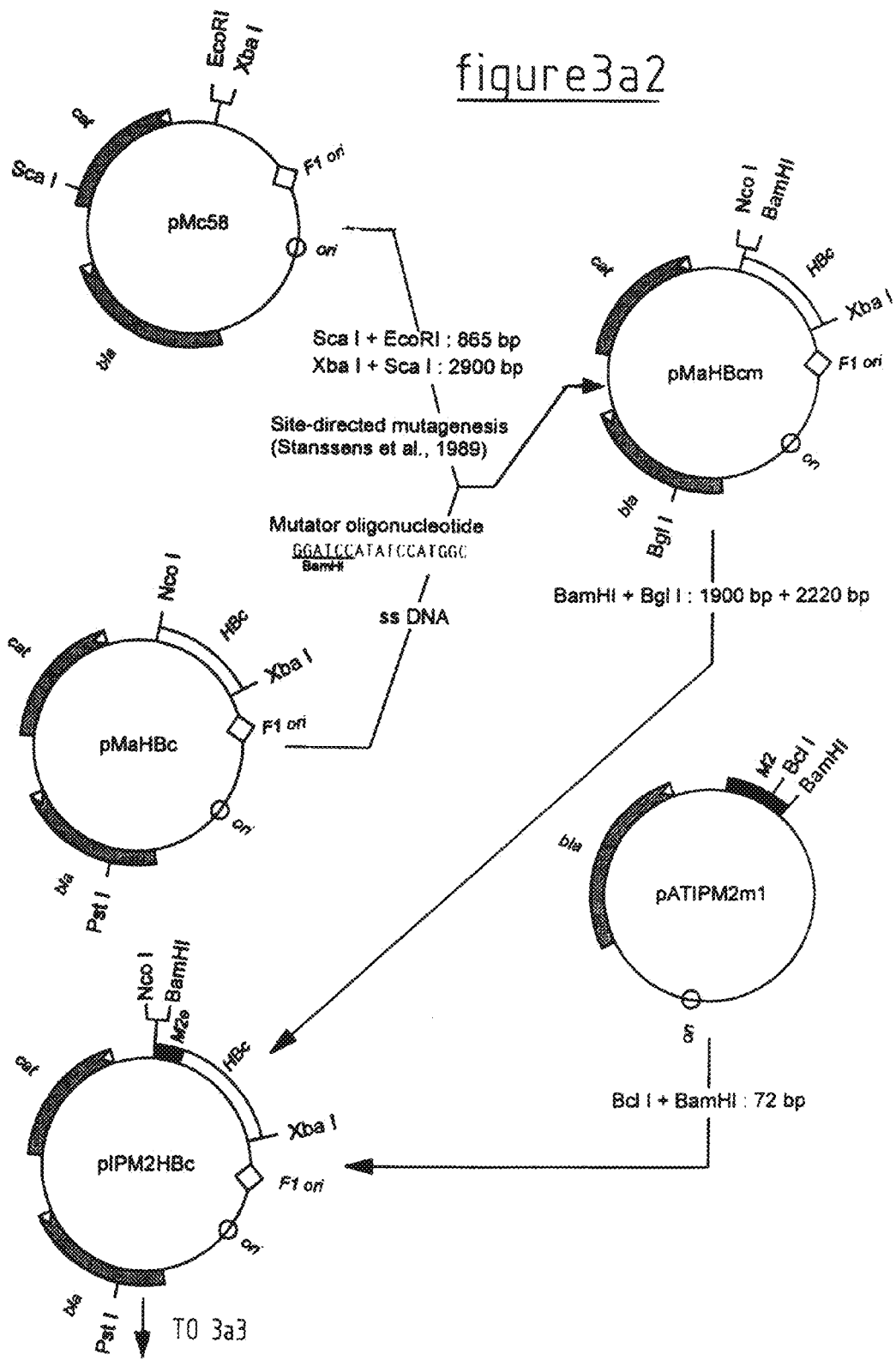

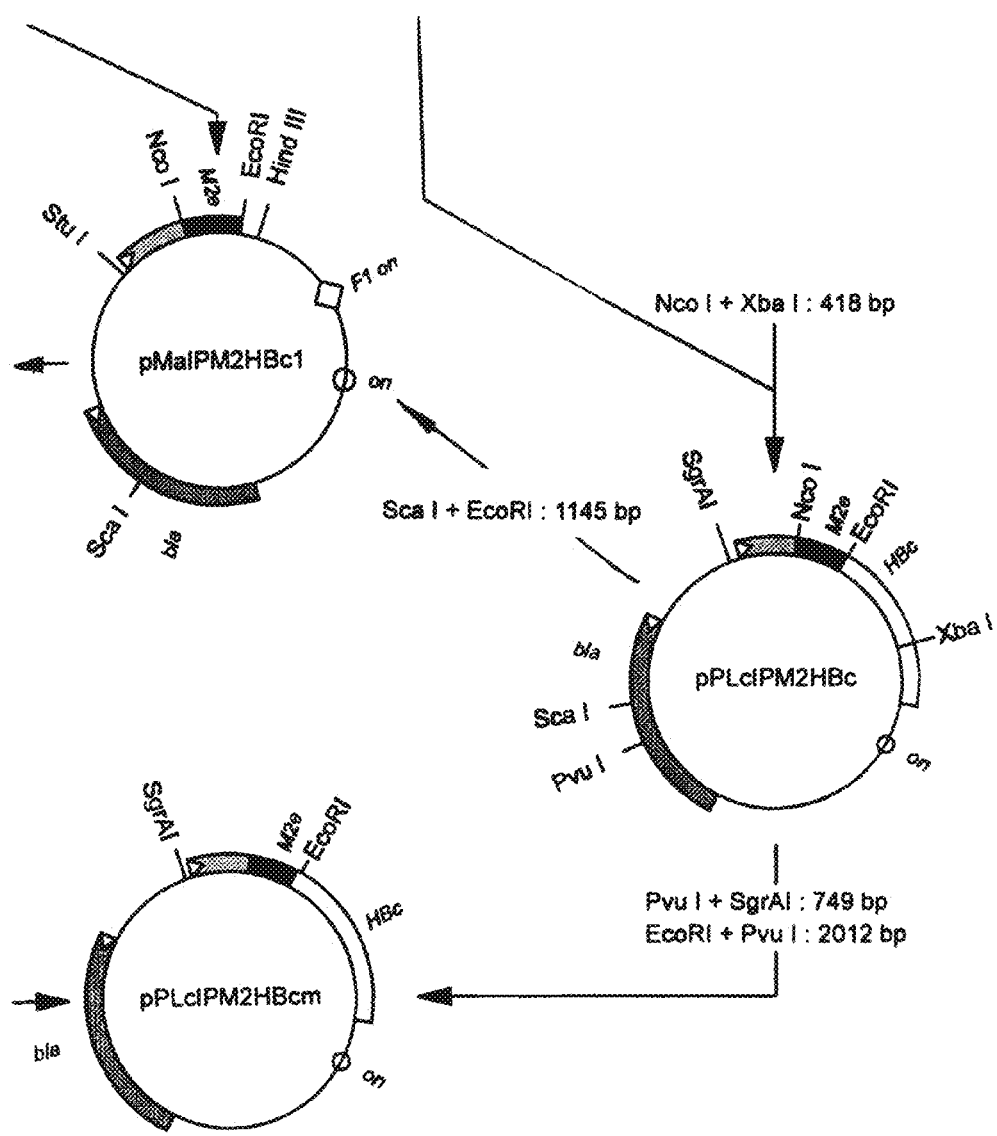

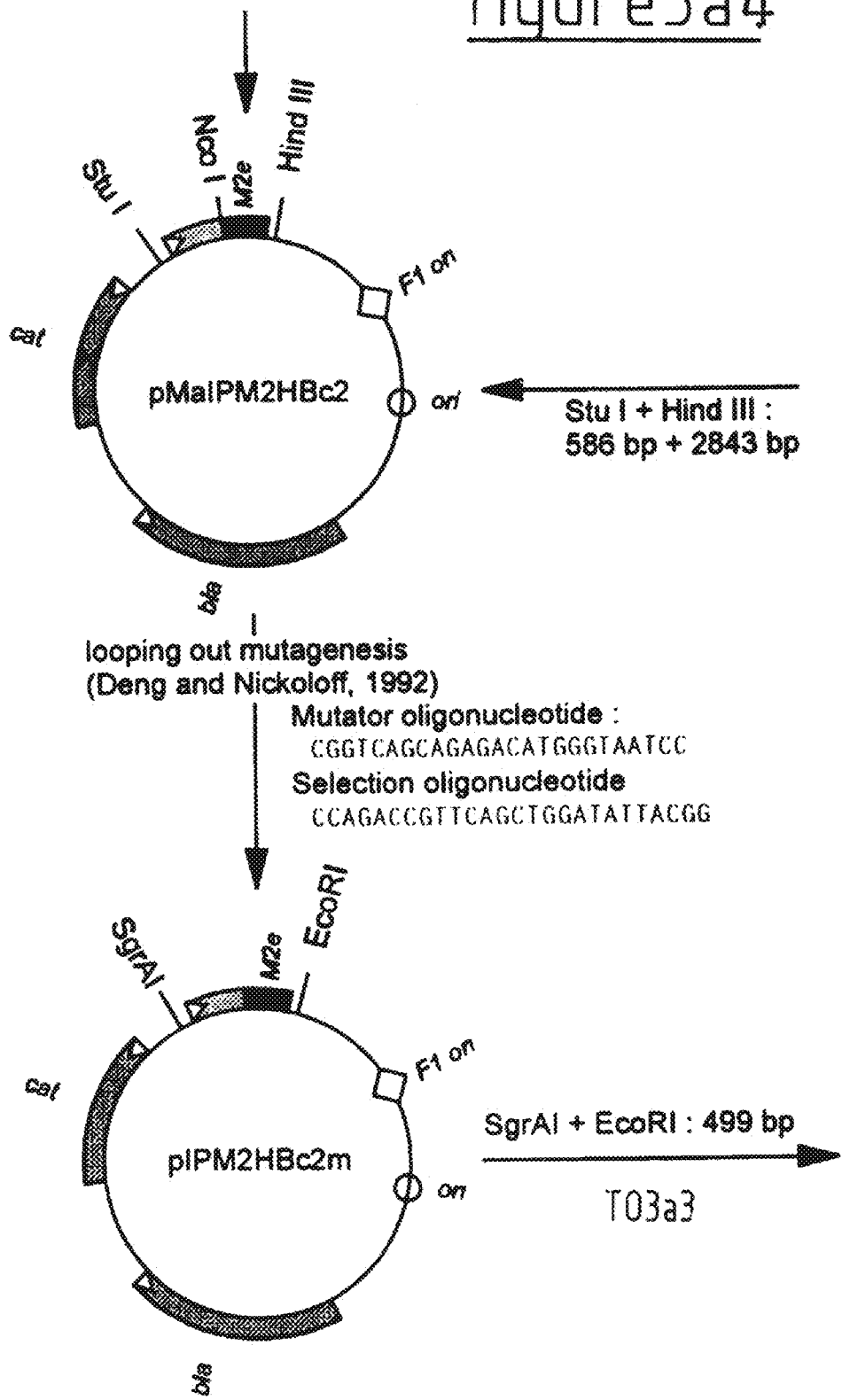

Figure 6

| | | | | | | | |
|---|---|---|---|---|---|---|---|
| ATG | TCT | CTG | CTG | ACC | GAA | GTT | GAA |
| Met | Ser | Leu | Leu | Thr | Glu | Val | Glu |
| | Ser | Leu | Leu | Thr | Glu | Val | Glu |
| | Ser | Leu | Leu | Thr | Glu | Val | Glu |

Nucleotide sequence of *ipm2hbcm*
Translated amino acid sequence
Amino terminus of the fusion protein IPM2HBcm
Amino terminus of the M2 protein of A/Udorn/72 fig. 8D
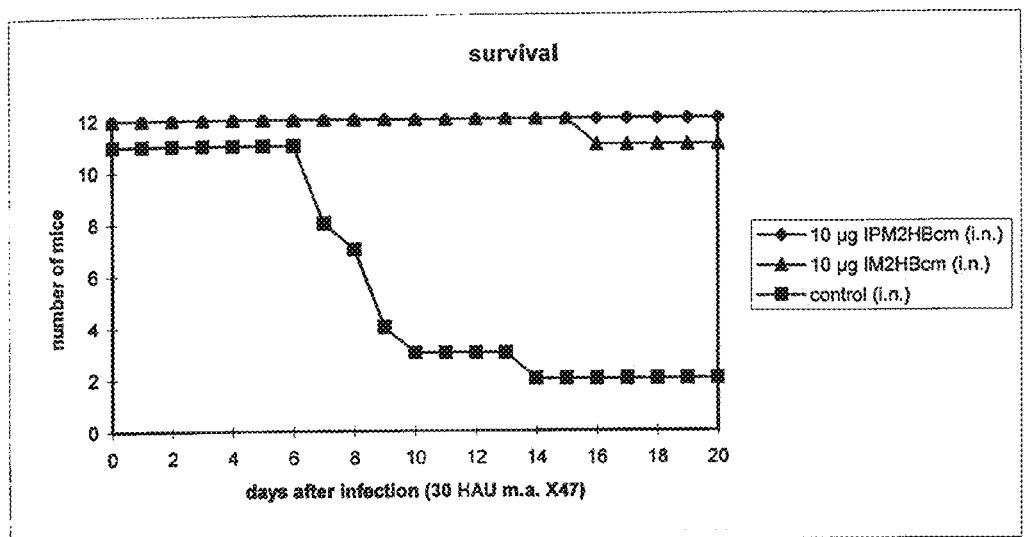
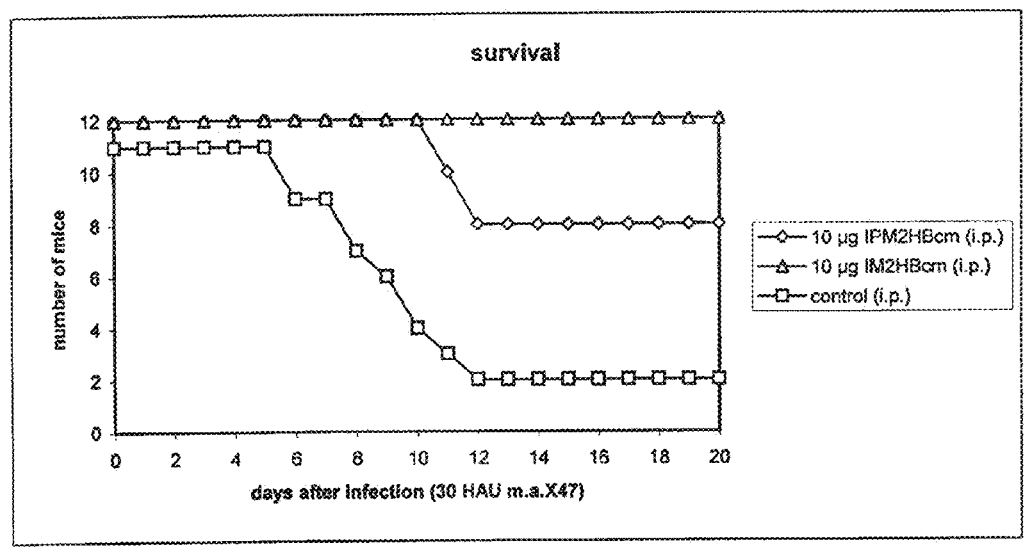
fig. 8C
| | surviving mice |
|---|---|
| 10 µg IPM2HBcm (i.n.) | 12/12 |
| 10 µg IM2HBcm (i.n.) | 11/12 |
| control (i.n.) | 2/11 |
| 10 µg IPM2HBcm (i.p.) | 8/12 |
| 10 µg IM2HBcm (i.p.) | 12/12 |
| control (i.p.) | 2/12 |

Figure 13

HBcs (27-mer)
　　C A T G G A T A T G G A T C C T T A T A A A G A A T T
　　　<u>　</u>
　　　start M2s (23-mer)
　　C A T G T C T C T G C T G A C C G A A G T T G
　　　<u>　</u>
　　　start M2Ls (29-mer)
　　C A T G T C T T T A T T A A C C G A A G T T G A A A C C C
　　　<u>　</u>
　　　start HBca (39-mer)
　　C G T G A T C A A C T A G T T C A C T A A C A T T G A G A T T C C C G A G A T
　　　　BclI　　　SpeI　stop

Figure 17

M2Ca (33-mer)
CG<u>GGATCC</u>CCACTTGAATCGTTACATCTGCACC
  BamH I

M2LSs (30-mer)
<u>TCTTTATTA</u>ACCGAAGTTGAAACCCCTATC
  Ser

C3ds (35-mer)
CCGCGCCCACCCGACGA<u>GATCT</u>CGGATCTACCCCC
                Bgl II

C3da (38-mer)
GC<u>ACTAGT</u>TCAA<u>GGATCC</u>GATCCGAACTCTTCAGATCC
  Spe I   stop  BamH I

Figure 19

TTFCs (35-mer)
CGGGATCCGACACCAATTCCATTTTCTTATTCTAA
    BamH I

TTFCa (25-mer)
GGGGATCCACTAGTTTAATCATTTG
    Bcl I    Spe I   stop

M2Ls (29-mer)
CATGTCTTTATTAACCGAAGTTGAAACCC
    start

Figure 22

GP67s (25-mer)
GCT<u>ACTAGT</u>AAATCAGTCACACCAA
     SpeI

GP67a (33-mer)
CG<u>AAGCTT</u>GC<u>CGGC</u>AAAGGCAGAATGCGCCGCC
  HindIII    NaeI

Figure 23

M2Ss (23-mer)
TCTCTGCTGACCGAAGTTGAAAC

UM2ECa (50-mer)
CG<u>AAGCTT</u><u>ACTAGT</u>TCAC<u>GGATCC</u>CCACTTGAATCGTTGCATCTGCACCC
  HindIII   SpeI   stop   BamHI

IMMUNOPROTECTIVE INFLUENZA ANTIGEN AND ITS USE IN VACCINATION

CROSS REFERENCE TO RELATED APPLICATION

Pursuant to 35 U.S.C. §§120 and 365(c), this application claims benefit of parental application Ser. No. 09/498,046, filed Feb. 4, 2000, now U.S. Pat. No. 7,731,972, that claimed the benefit of international application PCT/EP98/05106, filed Aug. 5, 1998, designating the United States, which application claimed the benefit of prior European application EP 97202434.3, filed Aug. 5, 1997.

FIELD OF THE INVENTION

The present invention relates to new immunoprotective influenza antigens, which are non-existent in nature. The invention further relates to the use of the antigens for vaccination and to vaccines containing them, as well as to methods for preparing the antigens.

BACKGROUND OF THE INVENTION

Influenza is caused by an RNA virus of the myxovirus group. Influenza viruses can be classified into three types (A, B and C), based on antigenic differences in the nucleoprotein and the matrix protein. Type A and B influenza viruses each contain 8 RNA segments, while type C only has 7 RNA segments. Influenza A is most important and is very pathogenic for man, as well as for animals, for example pigs and horses. Type B influenza causes disease in humans. Influenza C is less severe and was isolated from humans and pigs. The virus is transmitted through the air, mainly in droplets expelled during coughing and sneezing. The influenza viruses cause an infection of the respiratory tract, that is usually accompanied with coughing, high fever and myalgia. Although an influenza infection does not often lead to the death of the infected individual, the morbidity can be severe. As a consequence thereof influenza epidemics may lead to substantial economic loss. Furthermore, influenza infection can be more dangerous for certain groups of individuals, such as those having suffered from a heart attack, CARA patients or elderly. A vaccine against influenza is therefore highly desirable.

The influenza A virus contains in its membrane two highly immunogenic, but very variable proteins, the haemagglutinin and the neuraminidase. Due to the variability of these two proteins a broad spectrum long lasting vaccine against influenza A has so far not been developed. The influenza vaccine commonly used, has to be adapted almost every year to follow the antigenic drift of the virus. In these circumstances the vaccine can protect about 80% of the immunized persons. When more drastic changes occur in the virus, known as antigenic shift, the vaccine is no longer protective.

SUMMARY OF THE INVENTION

It is therefore the object of the present invention to provide a new immunoprotective antigen for use in vaccines which is not based on the rapidly changing haemagglutinin and/or neuraminidase and which therefore lacks the disadvantages of these known antigens and vaccines based thereon.

In the research that led to the present invention it was found that well conserved membrane proteins of influenza other than haemagglutinin and neuraminidase can be used for eliciting protection. Particularly useful for this approach is the membrane protein M2.

BRIEF DESCRIPTION OF THE DRAWINGS

FIG. 1: Construction of pATIPM2 ml.
E1 and E2=first and second exon of the influenza M2 protein
M2e=extracellular part of the M2 protein,
M2t=transmembrane part; and
M2c=cytoplasmic tail.
Bold line=vector
(a) removal of the intron out of the m2 gene SEQ ID NO: 59, E1 top and bottom [SEQ ID NOs:6, 7]
(b) introduction of a BclI site between the extracellular part and the transmembrane domain of the M2 protein, mutator [SEQ ID NO:8]
(c) nucleotide (SEQ ID NO:9) and amino acid sequence (SEQ ID NO:10) of the extracellular part of the M2 protein of A/PR/8/34, nucleotide sequence and amino acid sequence [SEQ ID NOs:9, 10].

FIG. 2: Construction of pIPM2hB2Mm2s2.
Ori=origin of replication,
Cat=chloramphenicol acetyltransferase,
Bla=β-lactamase,
Lpp=lipoprotein,
hB2M=human $\beta_2$-microglobulin,
ompa-ss=signal sequence of the outer membrane protein A of *E. coli*,
ssDNA=single-stranded DNA,
M2e=extracellular part of the M2 protein.
(a) Construction flow scheme, FIG. 2a2 mutator sequences (top and bottom) [SEQ ID NOs:11 and 12], FIG. 2a3 linkers (top and bottom) [SEQ ID NOs:13 and 14], FIG. 2a3 mutator [SEQ ID NO:15]
(b) Details of key sequences that include paired oligonucleotide and encoded amino acid sequences of SEQ ID NOs:44-51.

Figure 4:
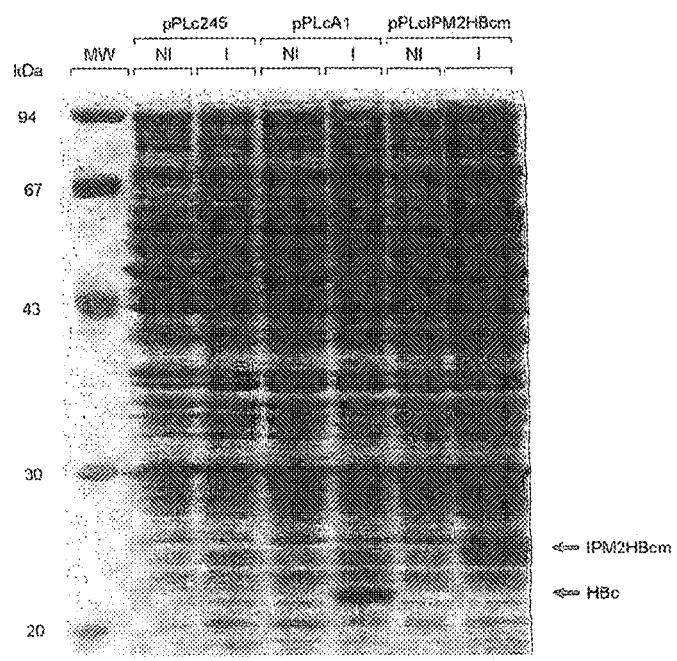
FIG. 4: Analysis of the soluble fraction, corresponding to 150 μl original culture, of strain MC1061[pcI857] containing the plasmids pPLc245 (control), pPLcA1 (expression of HBc) or pPLcIPM2HBcm (expression of IPM2HBcm) respectively, on a SDS 12.5% PAGE. After the electrophoresis the gel was stained with Coomassie brilliant blue.
MW=molecular weight marker,
NI=not induced culture,
I=induced culture.

or pPLcIPM2HBcm (expression of IPM2HBcm) respectively, as in FIG. 4. After electrophoresis, the relevant proteins were revealed by a Western blotting experiment. Detection with (A) a monoclonal antibody against HBc and (B) a monoclonal antibody specific for the extracellular part of the M2 protein.

MW=molecular weight marker,
NI=not induced culture,
I=induced culture.

FIG. 6: Sequence of the amino terminus of the M2 protein compared to the amino terminus of IPM2HBcm as an oligonucleotide, its translated amino acid residue sequence (SEQ ID NOs: 19 and 20) the amino acid residue sequence of the amino terminus of the fusion protein IPM2HBcm (SEQ ID NO: 21), as experimentally determined. Sequence of A/Udorn/72 SEQ ID NO: 62, (Lamb and Zebedee, 1985).

Figure 7:
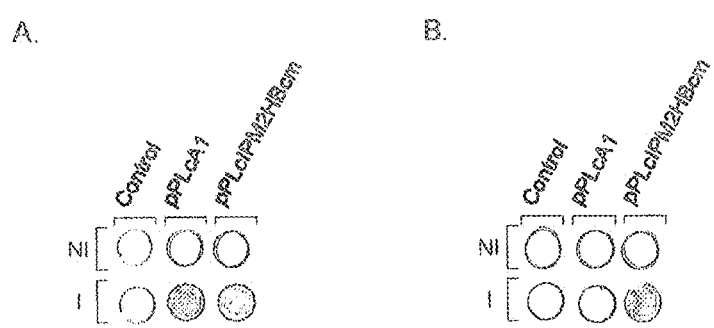

FIG. 7: Soluble fractions of strain MC1061 [pcI857] transformed with pPLc245 (control), pPLcA1 (expression of HBc) or pPLcIPM2HBcm (expression of IPM2HBcm), respectively, analyzed in a native state by means of a dot blot. Detection with (A) a monoclonal antibody against HBc and (B) a monoclonal antibody specific for the extracellular part of the M2 protein.
NI=not induced culture,
I=induced culture.

Figure 8:
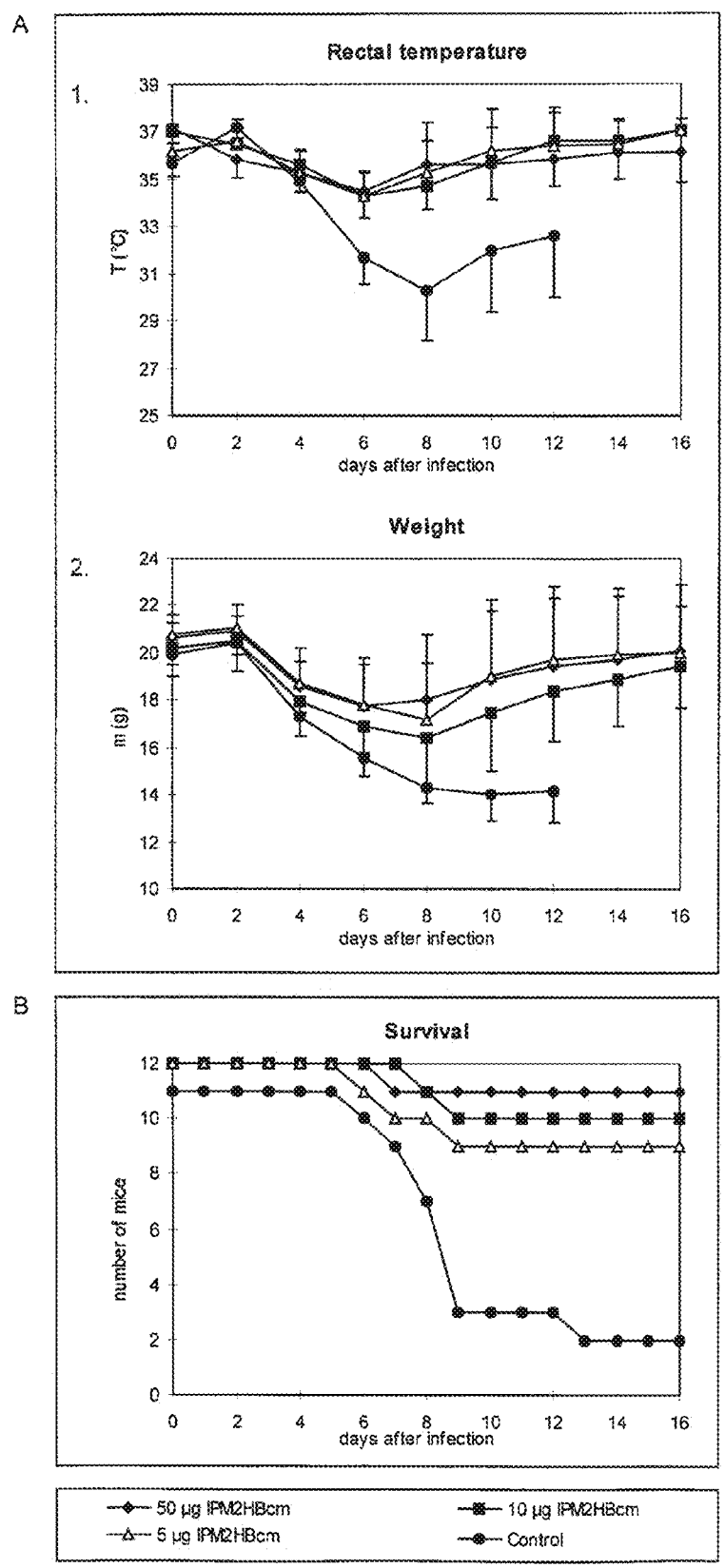

FIG. 8: Overview of (A1) rectal temperature, (A2) weight and (B) survival of the mice vaccinated with IPM2HBcm after a lethal challenge with 5 $LD_{50}$ m.a. A/PR/8/34. The statistical significance was calculated by the Fisher's exact test. Mice immunized with different doses of antigen were compared to the control group. The following results were obtained: for 50 µg IPM2HBcm p<0.001; for 10 µg p<0.005 and for the 5 µg dose p<0.05. FIG. 8C shows the survival of the mice vaccinated intraperitoneally with IPM2HBcm, and IM2HBcm, respectively, after a lethal challenge with 30 HAU X-47. FIG. 8D shows the survival of the mice vaccinated intranasally with IPM2HBcm, and IM2HBcm, respectively, after a lethal challenge with HAU X-47.

Figure 9:
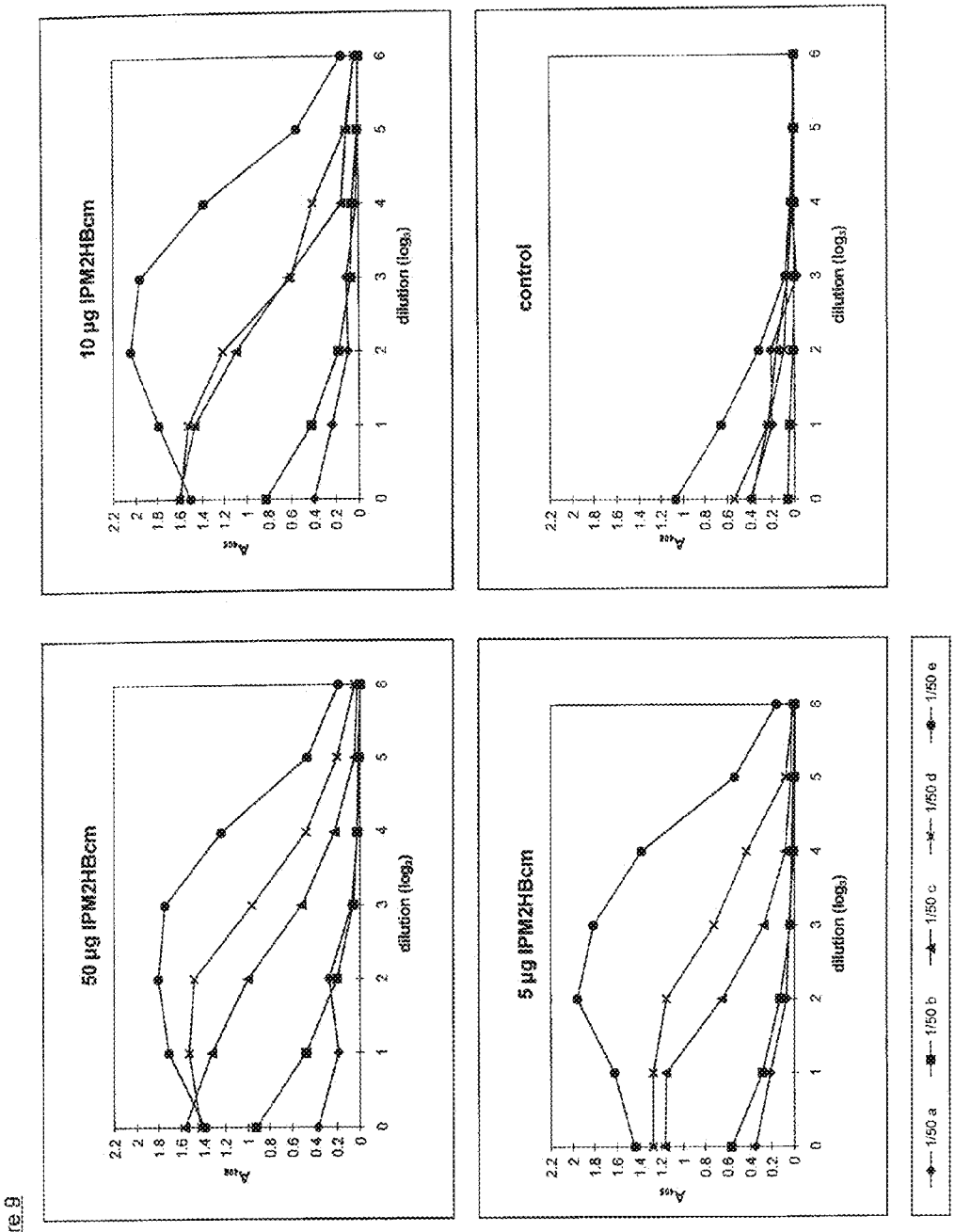

FIG. 9: Analysis of the serum samples of the four set ups reported in FIG. 8. The pre-immune serum (a), the serum taken after the first (b), after the second (c) and after the third (d) immunization and the serum taken after challenge (e) were initially diluted 1/50. The consecutive dilution steps were 1/3. The plotted absorbance is a corrected value obtained as described in Results, Analysis of the serum samples.

Figure 10:
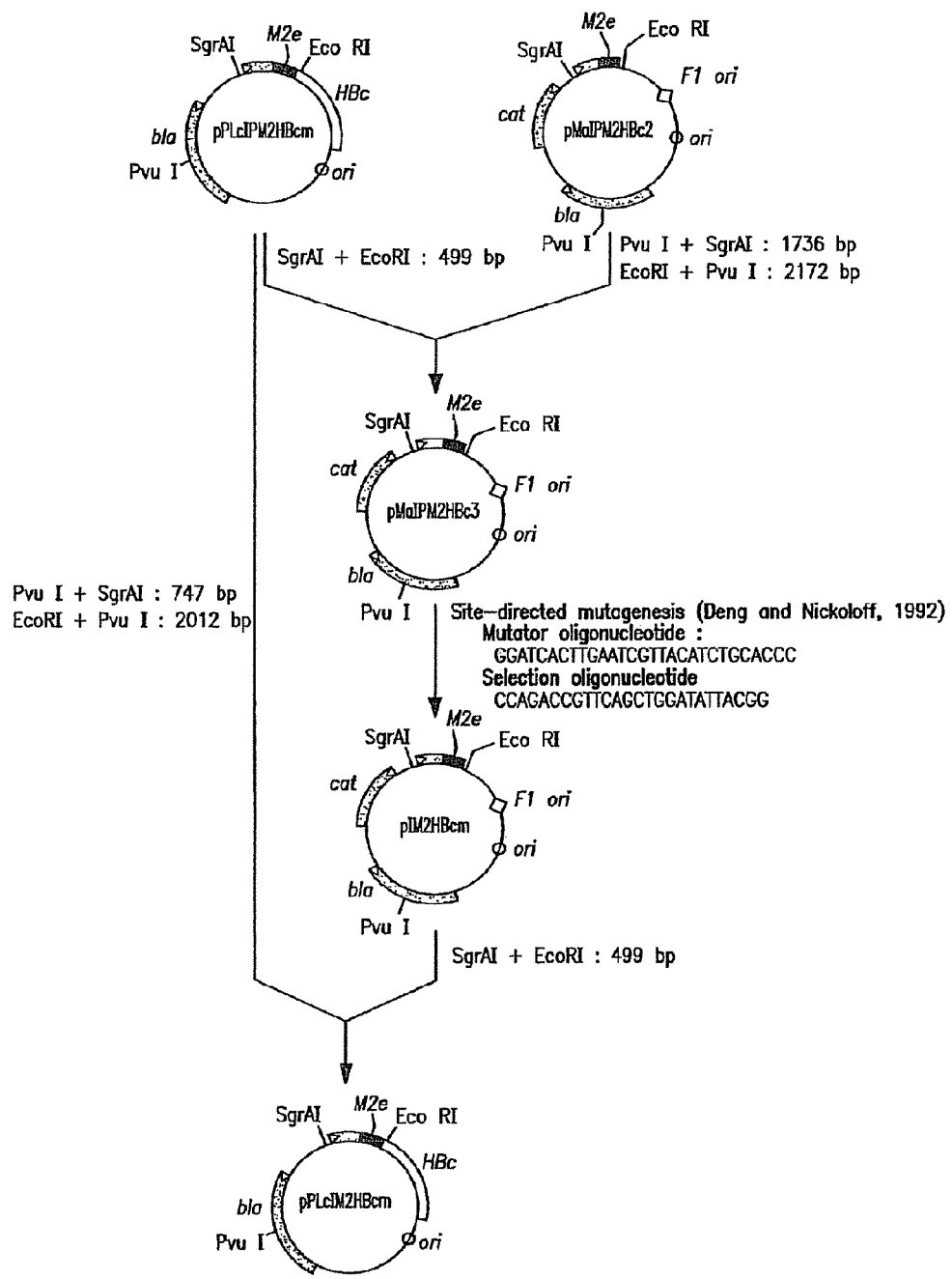

FIG. 10: Construction of pPLcIM2HBcm including the site-directed mutagenesis mutator oligonucleotide (SEQ ID NO: 22) and selection oligonucleotide (SEQ ID NO: 23),
ori=origin of replication,
cat=chloramphenicol acetyltransferase,
bla=β-lactamase,
M2e=extracellular part of the M2 protein,
HBc=hepatitis B core.

Figure 11:
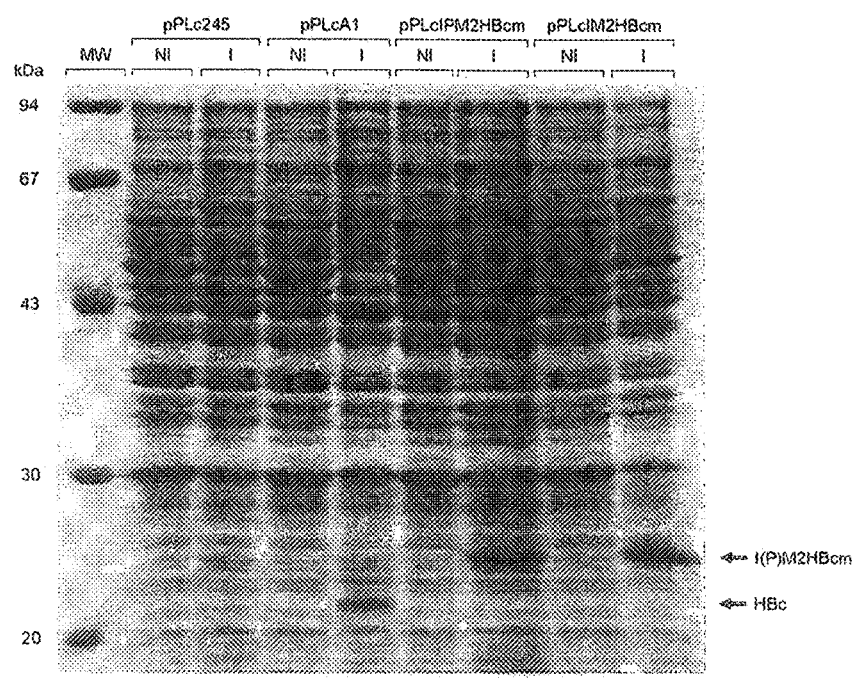

FIG. 11: Analysis of the soluble fraction, containing 5 µg HBc or I(P)M2HBcm (as determined in an ELISA (see Materials and Methods)), of strain MC1061 [pcI857] containing respectively the plasmids pPLc245 (control), pPLcA1 (expression of HBc), pPLcIPM2HBcm (expression of the fusion protein IPM2HBcm with the extracellular part of the M2 protein derived from A/PR/8/34) or PPLcIM2HBcm (expression of IM2HBcm, containing the more universal M2 sequence) on a SDS 12.5% PAGE-gel.
MW=molecular weight marker,
NI=not induced,
I=induced culture.

Figure 12:
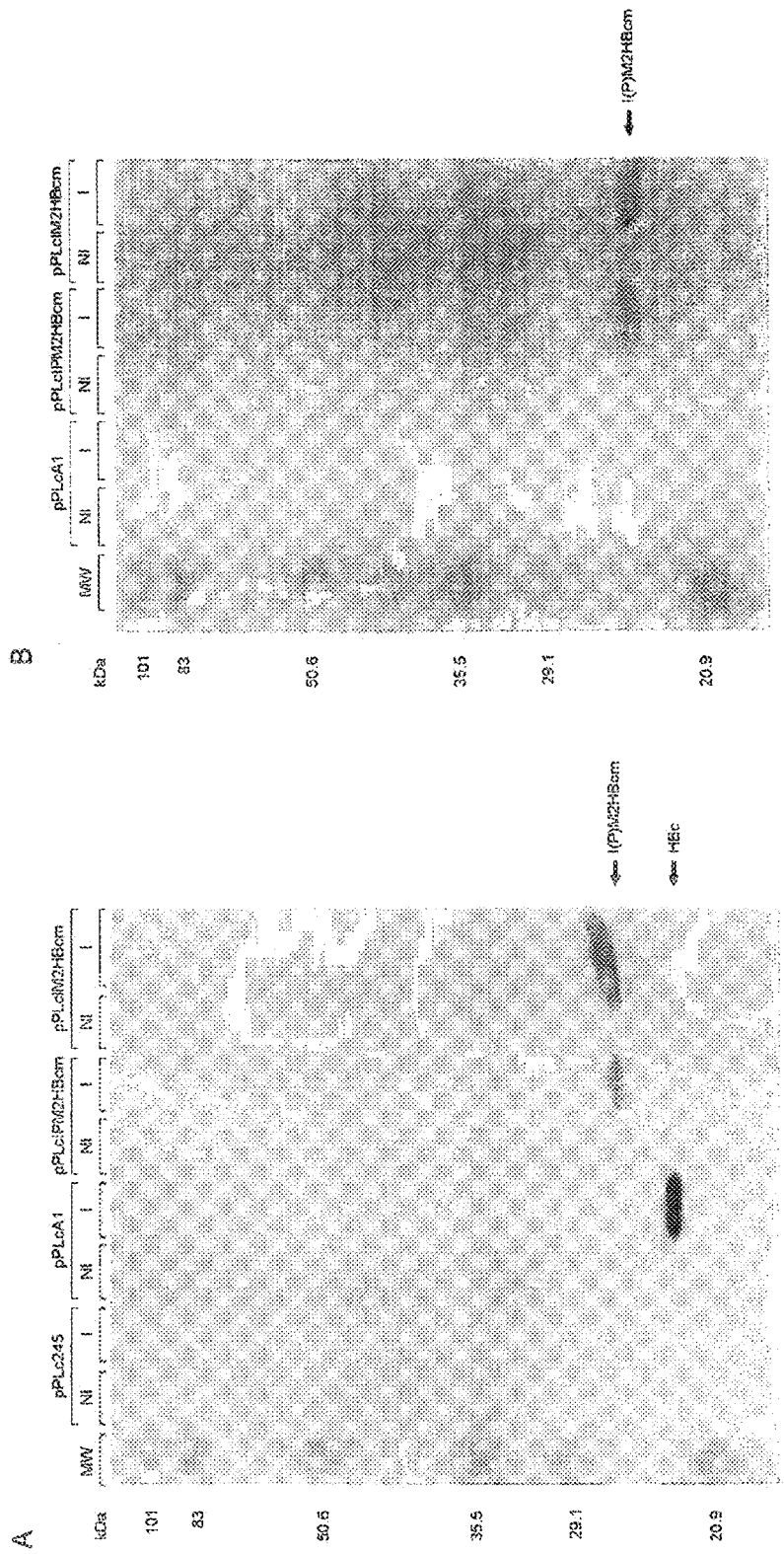

FIG. 12: Analysis of the soluble fraction, containing 2.5 µg HBc or I(P)M2HBcm (as determined in an ELISA (see Materials and Methods)), of strain MC1061 [pcI857] containing respectively the plasmids pPLc245 (control), pPLcA1 (expression of HBc), pPLcIPM2HBcm (expression of IPM2HBcm) or pPLcIM2HBcm (expression of IM2HBcm) on a Western blot (see Materials and Methods). Detection with (A) a monoclonal antibody directed against HBc and (B) a monoclonal antibody specific for the extracellular part of the M2 protein.
MW=molecular weight marker,
NI=not induced,
I=induced culture.

FIG. 13: Overview of the oligonucleotides (SEQ ID NOs: 24-27) used for PCR amplification of HBc and $i(p)_{m2}$HBc. 's' or 'a' following the name of the oligonucleotide stands for the use of these primers in the sense (s) or anti-sense (a) orientation. The boxed sequence indicates the changed Leu codons.

Figure 14:
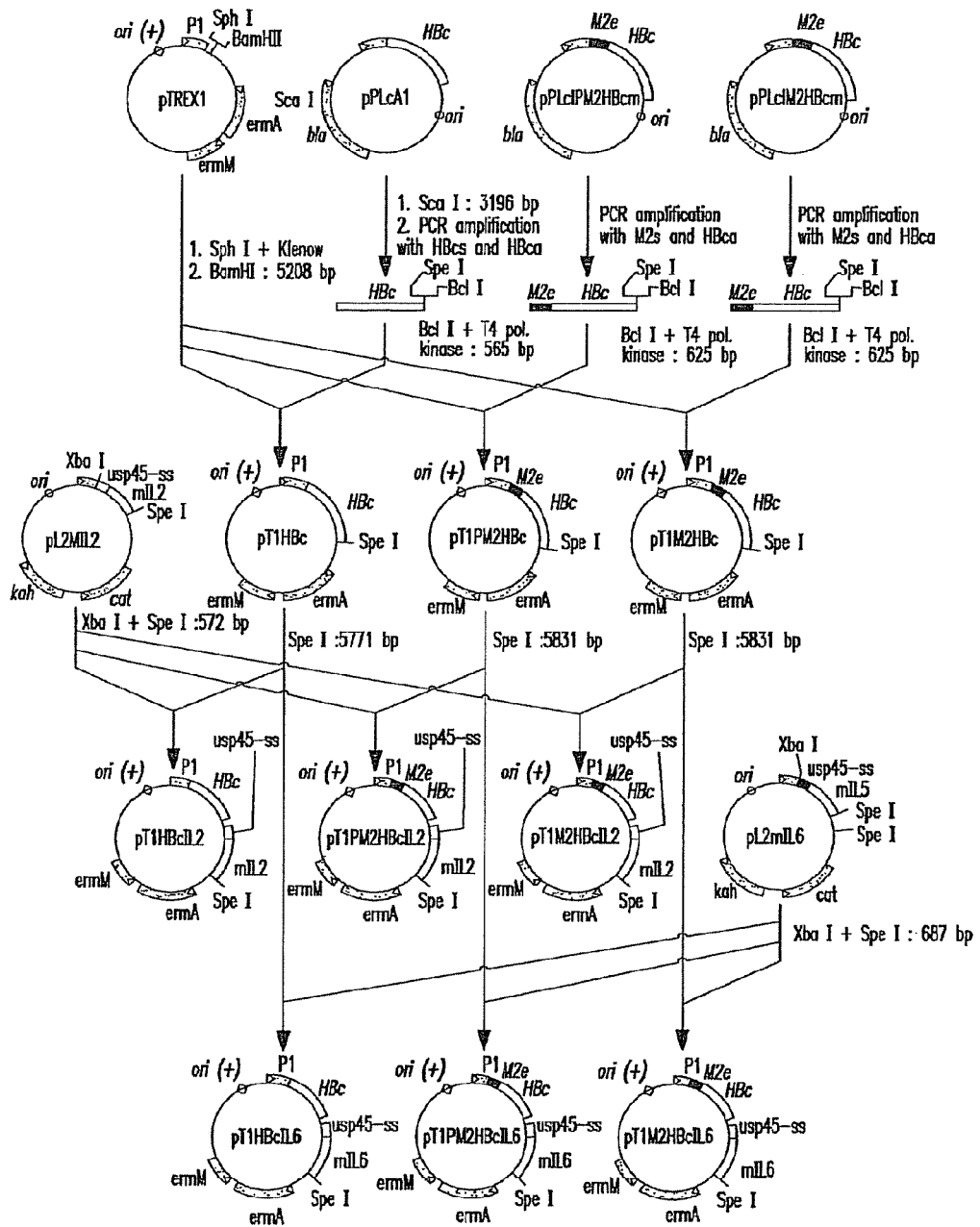

FIG. 14: Overview of the construction of hbc and m2hbc fusions in vectors for *L. lactis*
ori=origin of replication for *E. coli E. coli*,
ori(+)=origin of replication for *L. lactis*
ermA and ermM=erythromycin resistance genes,
P1=*L. lactis* promoter,
Bla=β-lactamase,
HBc=hepatitis B core,
M2e=extracellular part of the M2 protein,
usp45-ss=signal sequence of usp45,
mIL2=murine interleukin 2 and
mIL6=murine interleukin 6.

Figure 15:
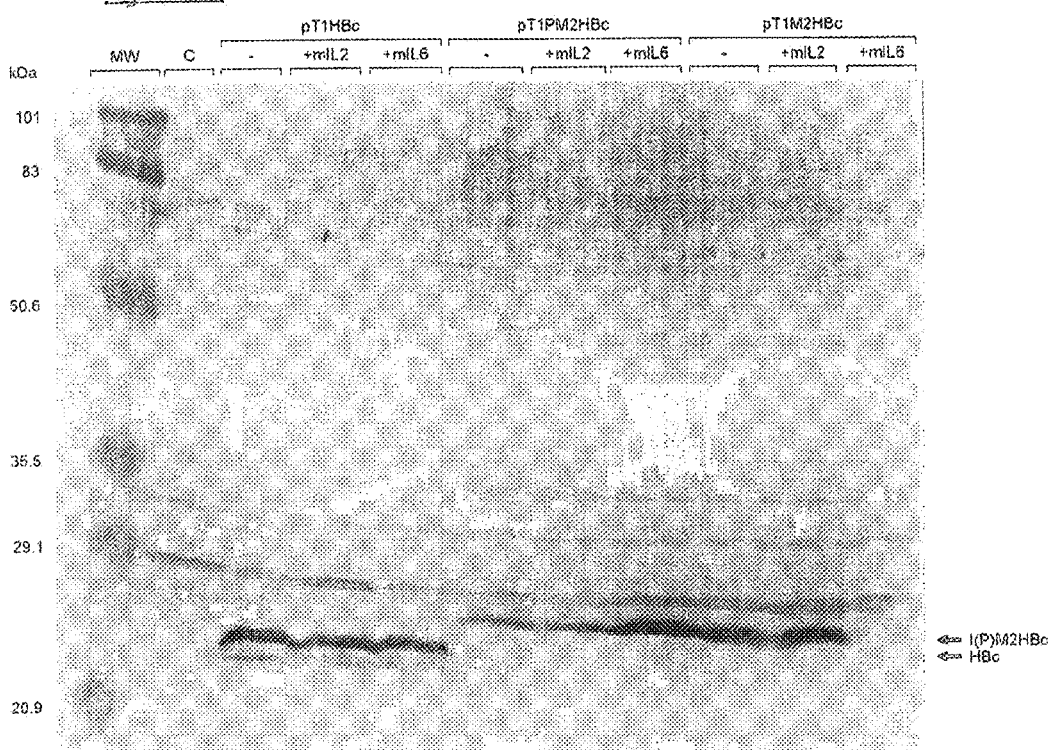

FIG. 15: Analysis of the expression of Hepatitis B core (HBc) and M2-HBc fusion proteins in a Western blot. An equivalent of $10^9$ *L. lactis* bacteria of strain MG1363 containing respectively pTREX1 (control), pT1HBc, pT1HBcIL2, pT1HBcIL6 (expression of HBc alone or in combination with mIL2 or mIL6, respectively), pT1PM2HBc, pT1PM2HBcIL2, pT1PM2HBcIL6 (expression of IPM2HBcm alone or in combination with mIL2 or mIL6, respectively), pT1M2HBc, pT1M2HBcIL2, pT1M2HBcIL6 (expression of IM2HBcm alone or in combination with mIL2 or mIL6, respectively), was analyzed in a SDS 12.5% PAGE-gel. The first antibody, p-anti-HBc (Dako Corporation, Carpinteria, Calif., USA) was diluted 5000 times. The bound antibodies were detected with a 1/2000 dilution of the polyclonal anti-rabbit IgG labeled with alkaline phosphatase (Southern Biotechnology Associates, Birmingham, Ala., USA). I(P)M2HBc stands for either IPM2HBcm or IM2HBcm.
MW=molecular weight marker,
C=control and
—=expression of the antigen alone.

Figure 16:
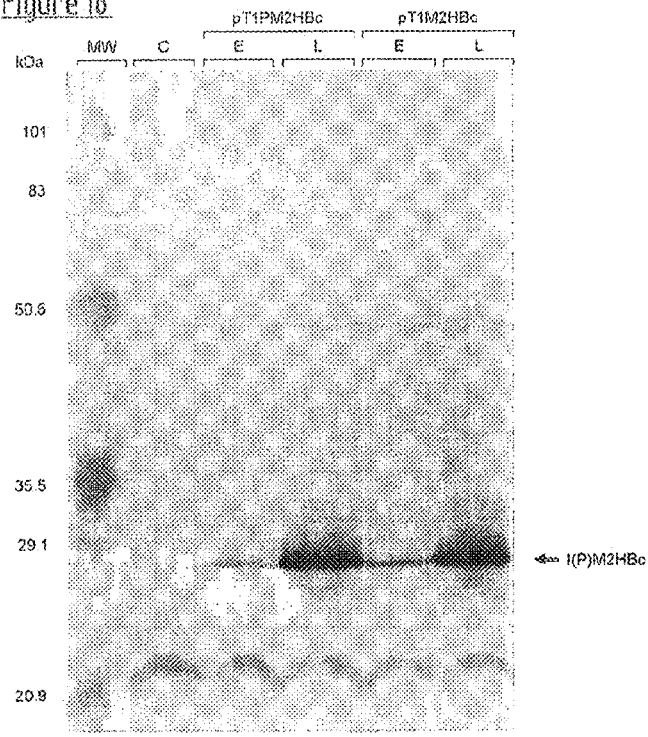

FIG. 16: Analysis of the expression of M2-HBc fusion proteins in a Western blot. An equivalent of 2 to 3×10⁹ *L. lactis* bacteria of strain MG1363 containing respectively pT1HBc (control), pT1PM2HBc, pT1PM2LHBc (expression of IPM2HBcm), pT1M2HBc, pT1M2LHBc (expression of IM2HBcm), was separated on a SDS 12.5% PAGE-gel. The fusion proteins were detected with an IgG fraction of a polyclonal mouse anti-M2e antibody (see Materials and Methods). The bound antibodies were detected with a 1/2000 dilution of the alkaline phosphatase conjugated polyclonal anti-mouse IgG (γ-chain specific) (Southern Biotechnology Associates, Birmingham, Ala., USA).
MW=molecular weight marker,
C=control,
E=leucine codons optimal for use in *E. coli* and
L=leucine codons optimal for use in *L. lactis*.

These are the plasmids pT1PM2LHBc and pT1M2LHBc, respectively. I(P)M2HBc stands for either IPM2HBcm or IM2HBcm.

FIG. 17: Overview of the oligonucleotides (SEQ ID NOs: 28-31) used for PCR amplification of the extracellular part of the M2 protein and C3d.

's' or 'a' following the code name of the oligonucleotide stands for the use of these primers in the sense (s) or anti-sense (a) orientation. The boxed region indicates the changed Leu codons.

Figure 18:
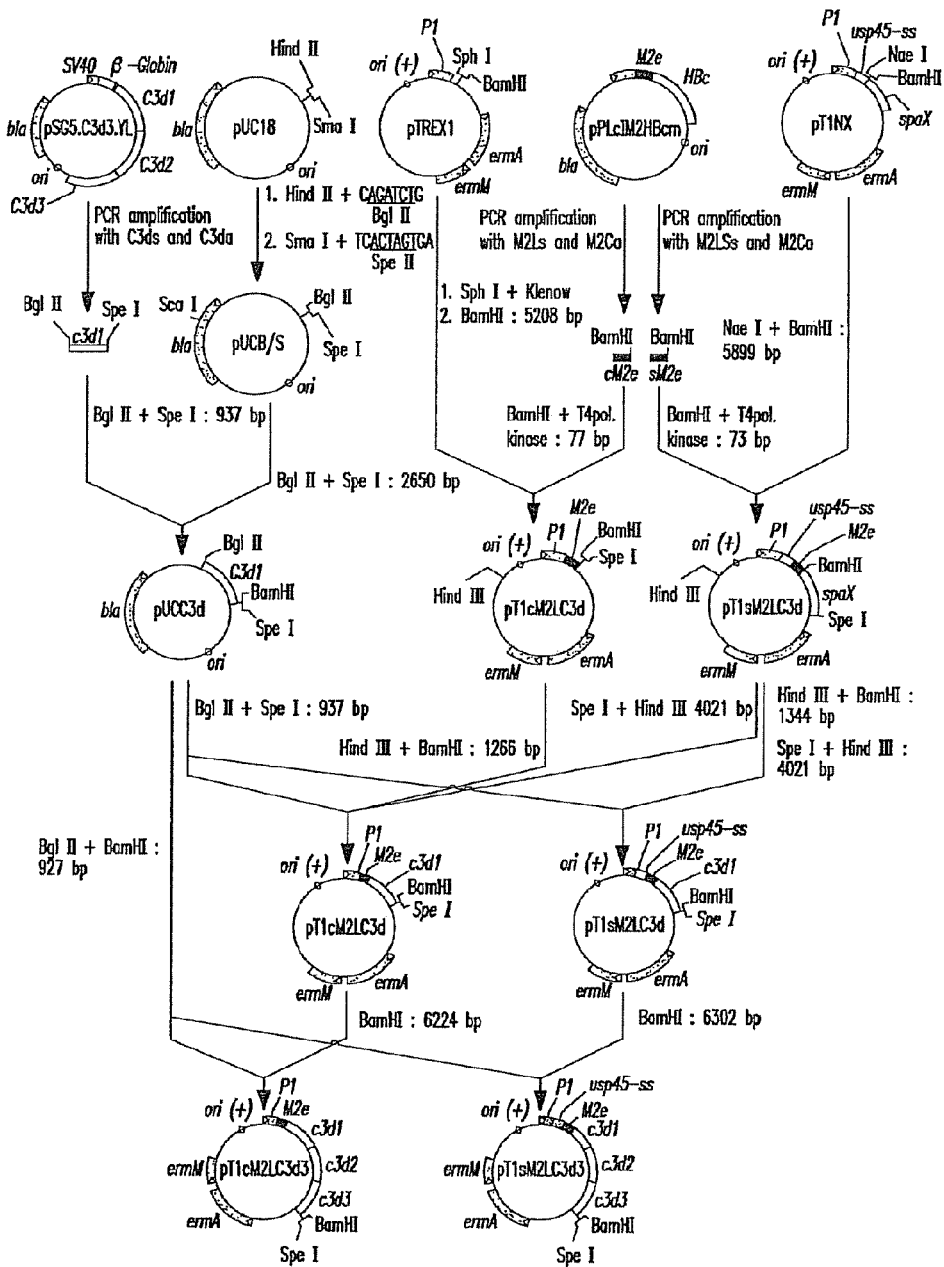

FIG. 18: Overview of the construction of m2c3d3 fusions in L. lactis.
ori=origin of replication for E. coli.
ori(+)=origin of replication for L. lactis,
ermA and ermM=erythromycin resistance genes,
P1=L. lactis promoter,
Bla=β-lactamase,
M2e=extracellular part of the M2 protein,
usp45-ss=signal sequence of usp45,
spaX=anchor sequence derived from Staphylococcus aureus protein A,
C3d=complement protein 3 fragment d, and
mIL6=murine interleukin 6.

FIG. 19: Overview of the oligonucleotides (SEQ ID NOs: 32-34) used for PCR amplification of TTFC and m2TTFC. 's' or 'a' following the name of the oligonucleotide stands for the use of these primers in the sense (s) or anti-sense (a) orientation. The boxed region indicates the changed Leu codons.

Figure 20:
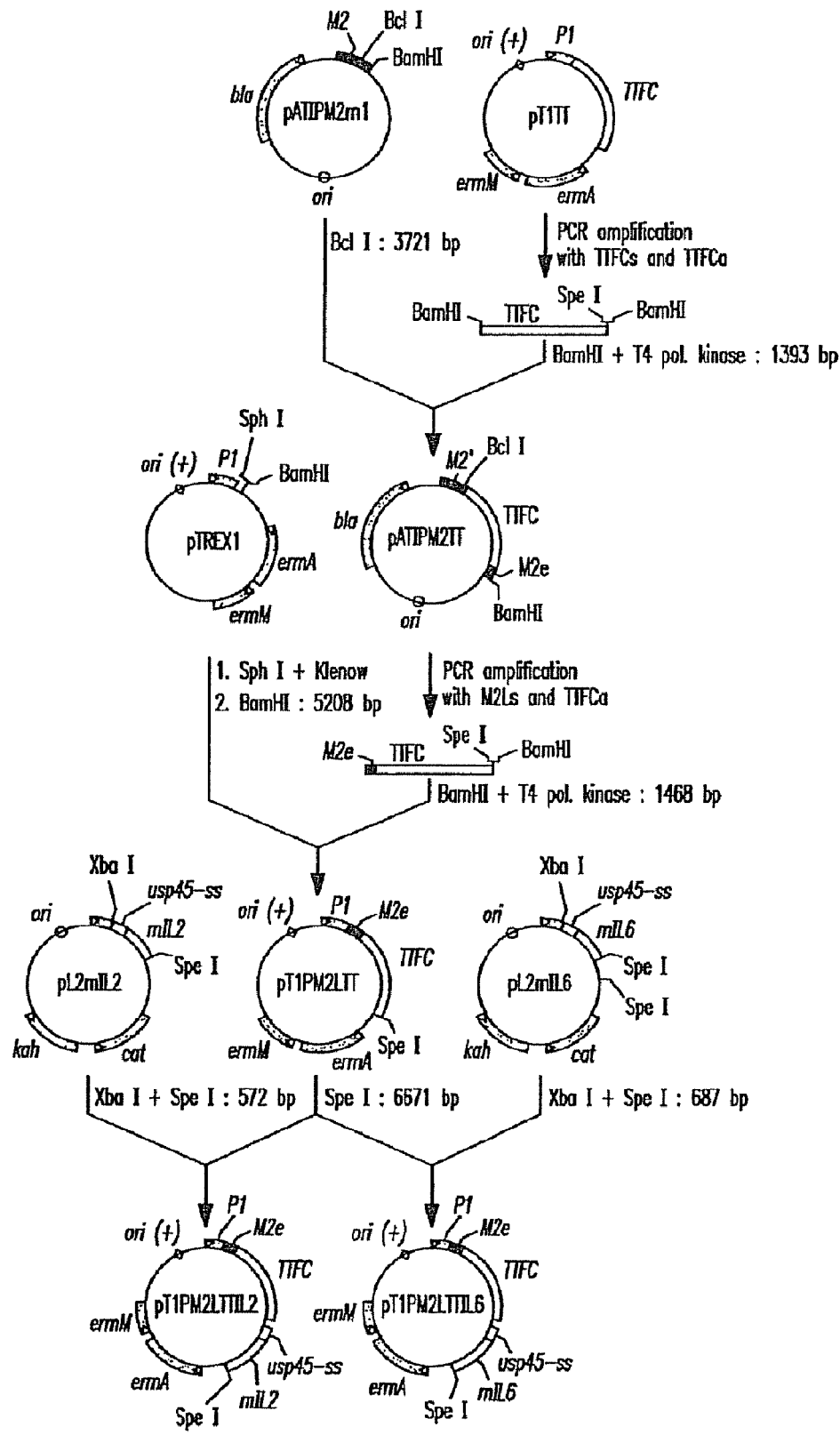

FIG. 20: Overview of the construction of m2TTFC in vectors for L. lactis.
ori=origin of replication for E. coli,
ori(+)=origin of replication for L. lactis
ermM and ermμ=erythromycin resistance genes,
P1=L. lactis promoter,
Bla=β-lactamase,
TTFC=tetanus toxin fragment C,
M2e=extracellular part of the M2 protein,
usp45-ss=signal sequence of usp45,
mIL2=murine interleukin 2, and
mIL6=murine interleukin 6.

Figure 21:
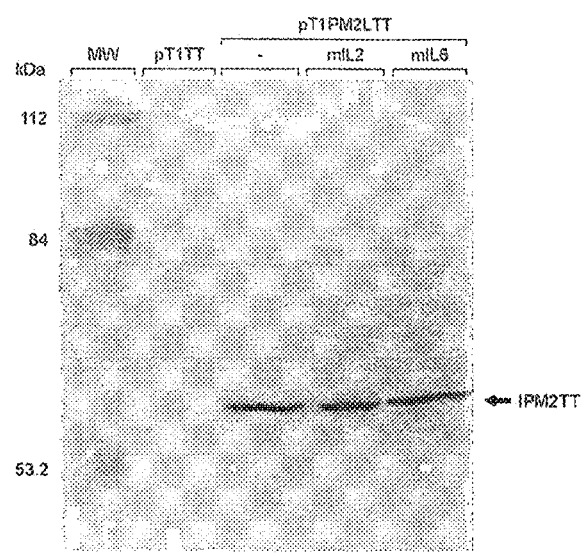

FIG. 21: Analysis of the expression of IPM2TTFC fusion protein in a Western blot. An equivalent of $10^9$ L. lactis bacteria of strain MG1363 containing respectively pT1TT (control), pT1PM2LTT (expression of IPM2TT), pT1PM2LTTIL2 (expression of IPM2TT in combination with mIL2) or pT1PM2LTTIL6 (expression of IPM2TT in combination with mIL6), was analyzed in a SDS 10% PAGE-gel. The first antibody, an IgG fraction of a polyclonal mouse anti-M2e antibody (see Materials and Methods) was diluted 2500 times. The bound antibodies were detected with a 1/2000 dilution of the polyclonal anti-mouse IgG labeled with horseradish peroxidase (Southern Biotechnology Associates, Birmingham, Ala., USA). 30 mg 4-chloro-1-naphthol (Sigma Chemical Co., St. Louis, Mo., USA), was solublized in 10 ml methanol.) Afterwards 40 ml PBS, pH 7.4 and 150 μl $H_2O_2$ was added.
MW=molecular weight marker,
−=expression of the antigen alone,
mIL2=expression of the antigen in combination with mIL2, mIL6=expression of the antigen in combination with mIL6.

FIG. 22: Primer set (SEQ ID NOs: 35 and 36) used for PCR amplification of the secretion signal of the gp67 baculovirus protein.

FIG. 23: Primer set (SEQ ID NOs: 37 and 38)used for PCR amplification of the extracellular part of the M2 protein during construction of the sgpM2C3d3 fusion.

Figure 24:
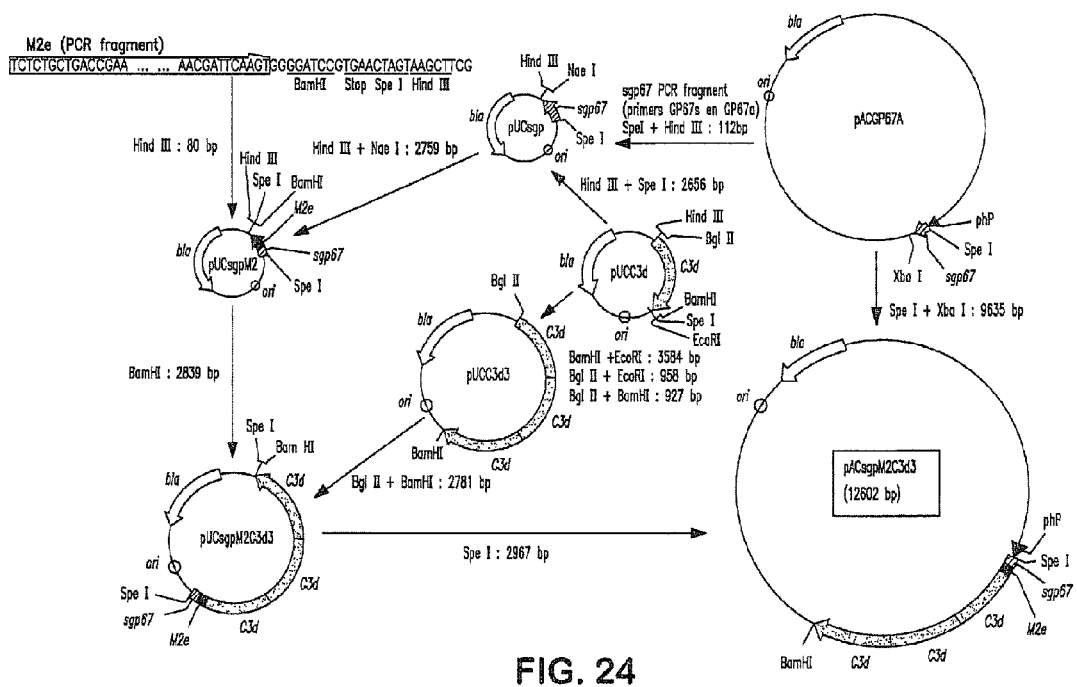

FIG. 24: Construction of the baculovirus transfer vector pACsgpM2C3d3.
Bla=β-lactamase,
bold grey line=baculovirus homology region,
C3d=complement protein 3 fragment d,
M2e=extracellular part of the M2 protein (SEQ ID NO: 64),
ori=origin of replication,
phP=baculovirus polyhedrin promoter, and
sgp67=secretion signal of the gp67 baculovirus protein.

Figure 25:
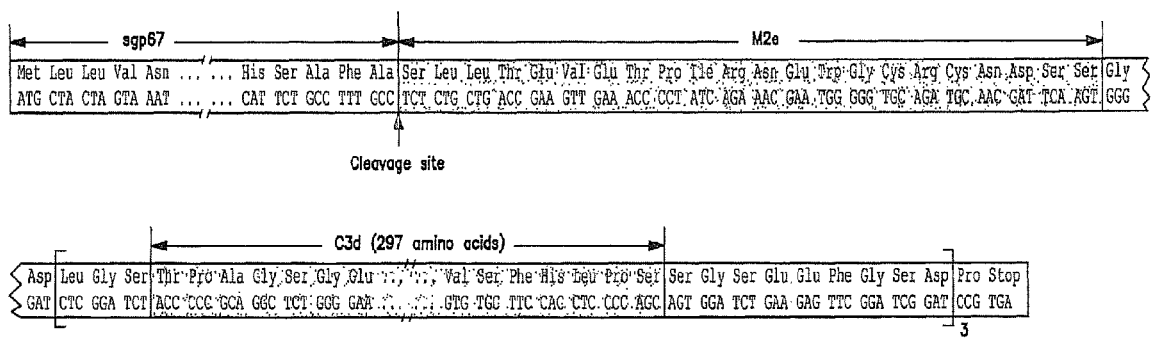

FIG. 25: Detail of nucleotide and amino acid key sequences of the sgpM2C3d3 fusion.
C3d=complement protein 3 fragment d (SEQ ID NOs: 68 and 67),
M2e=extracellular part of the M2 protein (SEQ ID NOs: 66 and 65), and
sgp67=secretion signal of the gp67 baculovirus protein.

Figure 26:
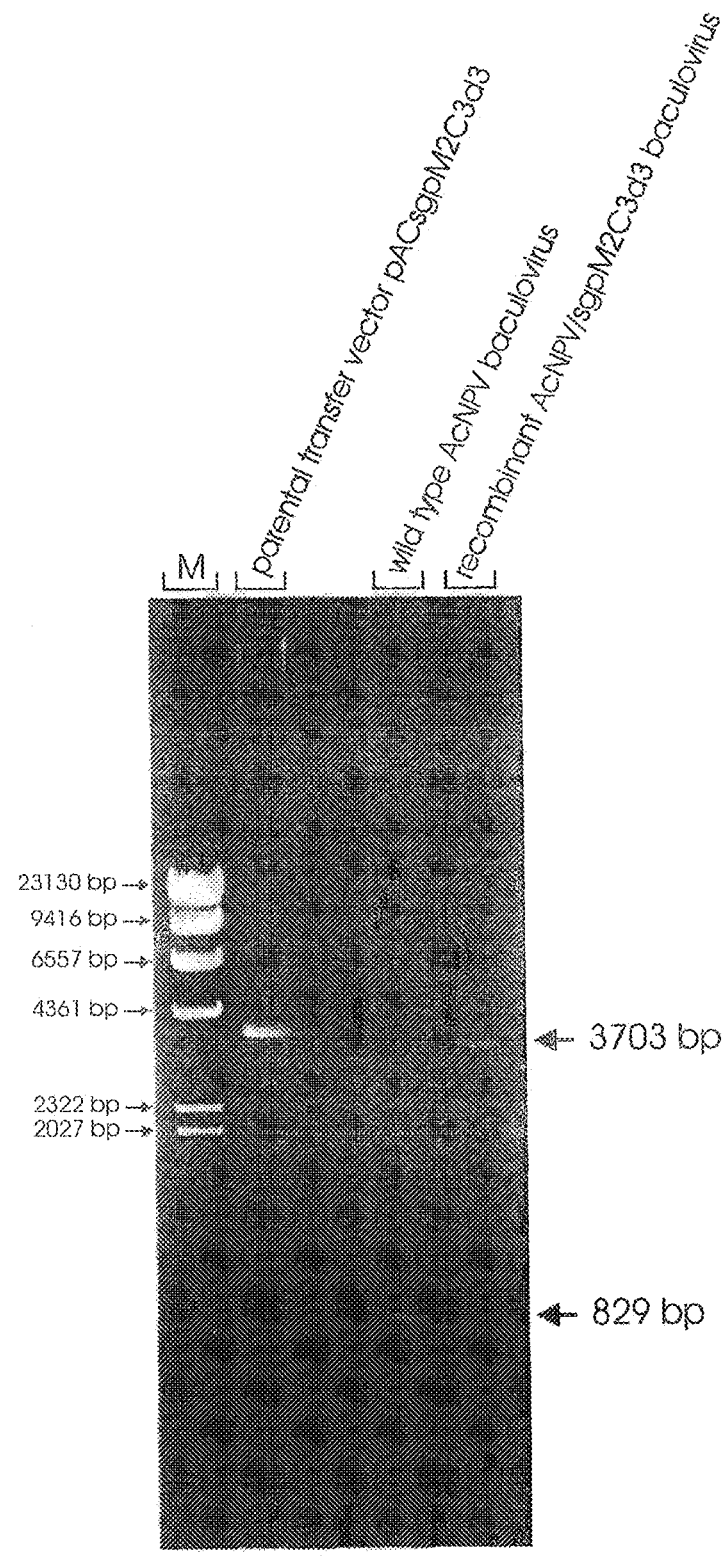

FIG. 26: Analysis of recombinant AcNPV/sgpM2C3d3 baculovirus by PCR amplification of the polyhedrin locus (primers TTTACTGTTTTCGTAACAGTTTTG and CAA-CAACGCACAGAATCTAG SEQ ID NOs: 4 and 5). Control reactions were performed with the parental transfer vector pACsgpM2C3d3 and with wild type AcNPV baculovirus.
M=DNA size markers.

Figure 27:
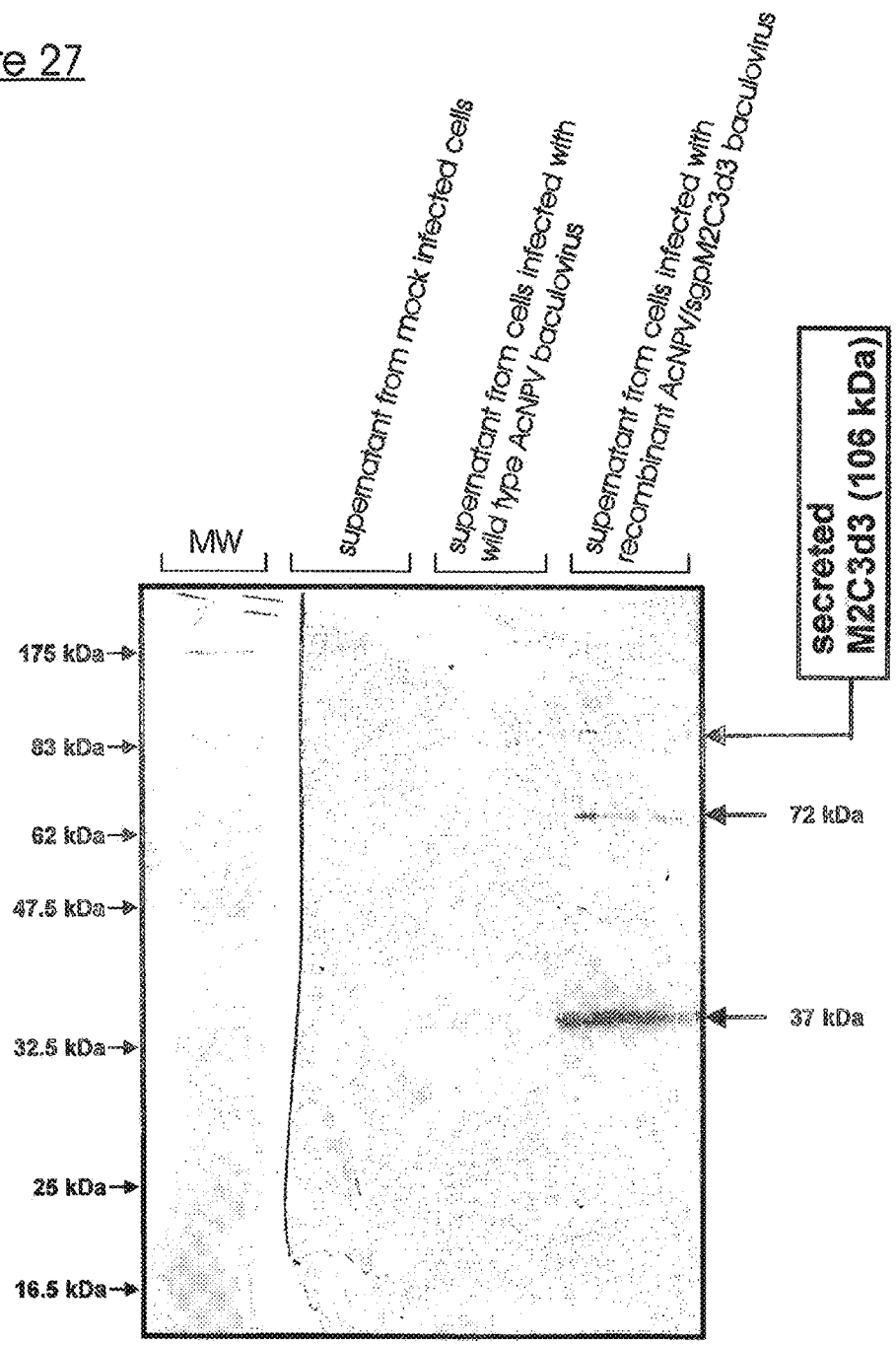

FIG. 27: Expression of secreted M2C3d3 by sf9 insect cells infected with recombinant AcNPV/sgpM2C3d3 baculovirus as demonstrated by Western analysis (10% PAGE-gel) of harvested supernatant. Supernatant from mock infected cells or obtained after infection with wild type AcNPV baculovirus are included as a control.
MW=molecular weight markers.

Figure 28:
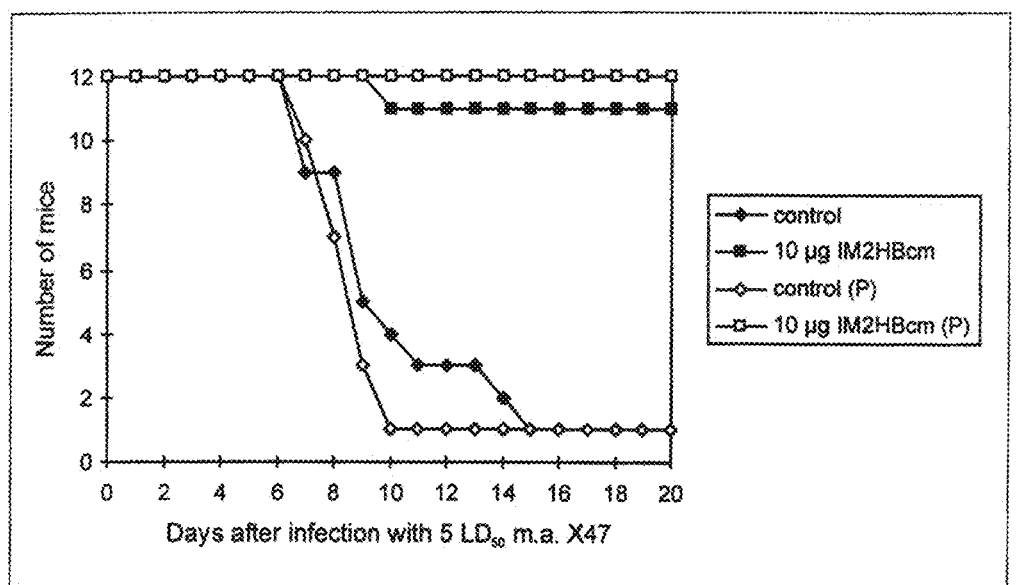

FIG. 28: Overview of the survival of mice after a lethal challenge with 5 $LD_{50}$ m.a. X47. M1ce vaccinated with 3×10 μg IM2HBcm are compared with passively immunized mice (P).

Figure 29:
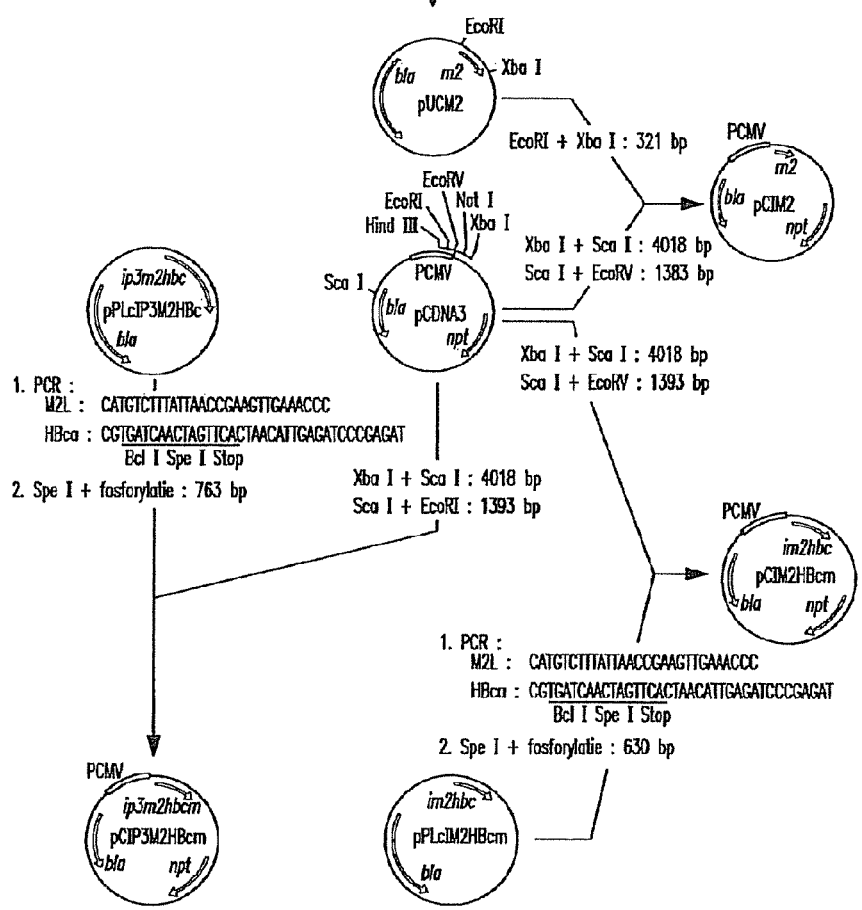

FIG. 29: Overview of the DNA vaccination constructs including the oligonucleotides of SEQ ID NOs: 39-43.
RT=reverse transcriptase
PCMV=cytomegalovirus promoter
Bla=β-lactamase
Npt=neomycin resistance.

Figure 30:
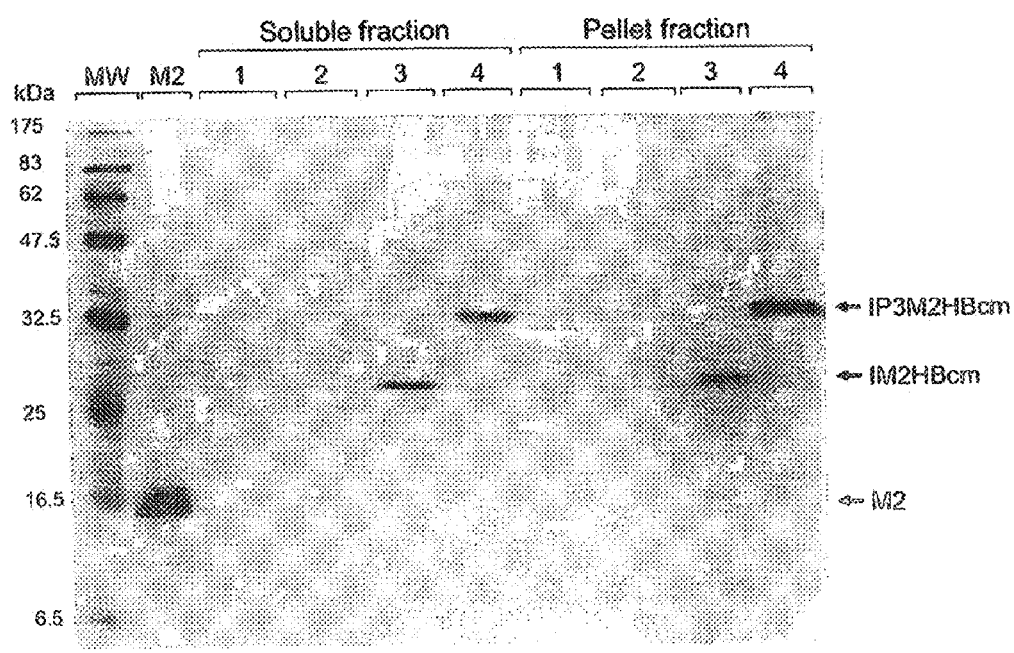

FIG. 30 Expression in HEKT cells analyzed on a Western blot. The first antibody (paM2 (see Materials and Methods)) was diluted 2000 times. The bound anti-M2 antibodies were detected with an alkaline phosphatase labeled anti-mouse IgG.
MW=molecular weight marker
M2=M2 protein expressed in insect cells
1=pcDNA3
2=pCIM2
3=pCIM2HBcm
4=pCIP3M2HBcm.

Figure 31:
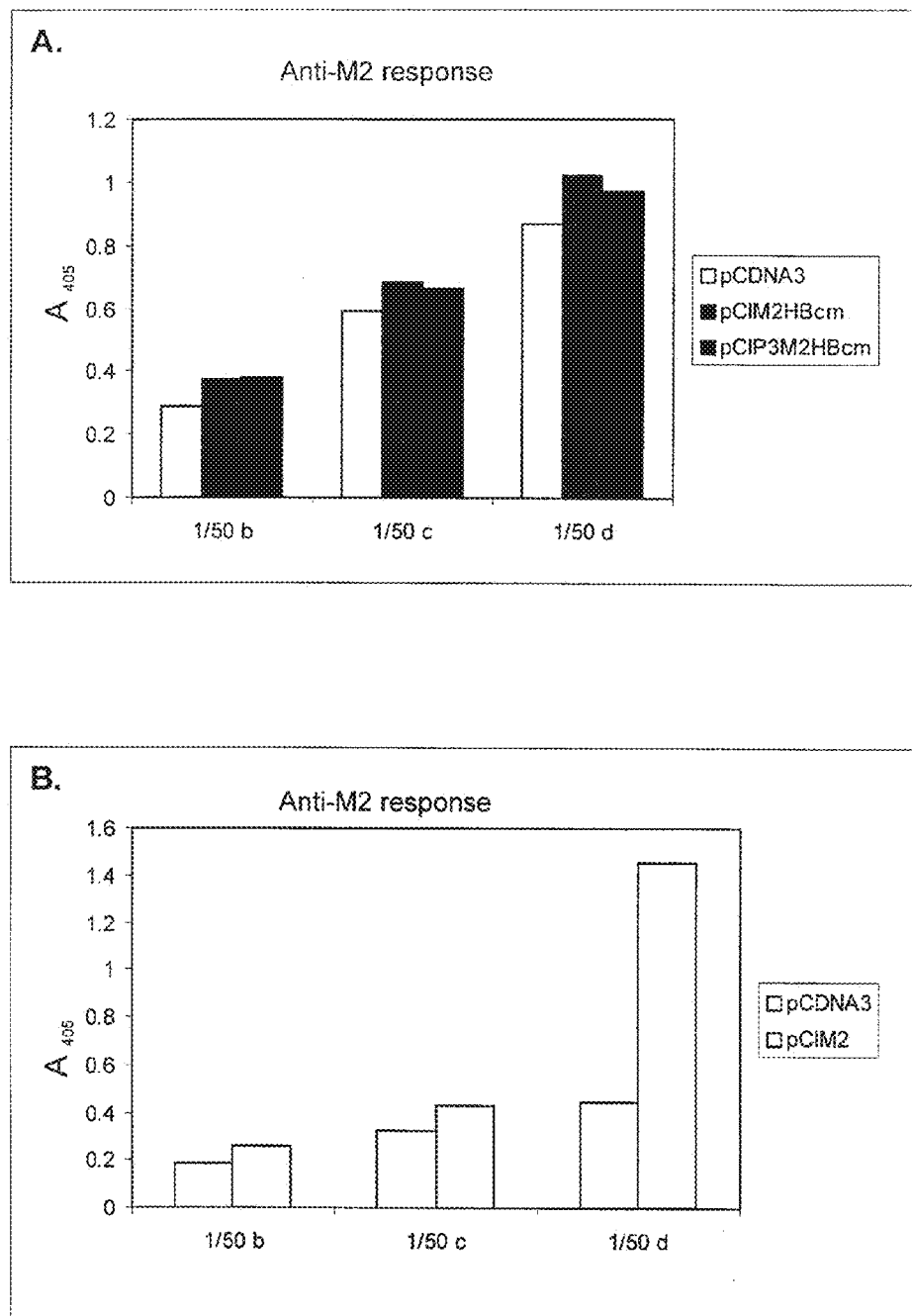

FIG. 31 Antibody response against the M2 protein analyzed in an ELISA.
A. Microtiterplates were coated with periplasm containing hB2M or IPM2hB2M respectively (see Materials and Methods).
B. Microtiterplates coated with M2 protein expressed in insect cells (see Materials and Methods).

DETAILED DESCRIPTION OF THE INVENTION

M2 mRNA is encoded by RNA segment 7 of the influenza A virus. It is encoded by a spliced mRNA (Lamb et al., 1981). Like the haemagglutinin and the neuraminidase, the M2 protein is an integral membrane protein of the influenza A virus. But the protein is much smaller, only 97 amino acids long. 24 Amino acids at the amino terminus are exposed outside the membrane surface, 19 amino acids span the lipid bilayer, while the remaining 54 residues are located on the cytoplasmic side of the membrane (Lamb et al., 1985).

The M2 protein is abundantly expressed at the cell surface of influenza A infected cells (Lamb et al., 1985). The protein is also found in the membrane of the virus particle itself, but in much smaller quantities, 14 to 68 molecules of M2 per virion (Zebedee and Lamb, 1988). The M2 protein is post-translationally modified by the addition of a palmitic acid on cysteine at position 50 (Sugrue et al., 1990).

The M2 protein is a homotetramer composed of two disulfide-linked dimers, which are held together by noncovalent interactions (Sugrue and Hay, 1991). By site-directed mutagenesis, Holsinger and Lamb (1991) demonstrated that the cysteine residue at position 17 and 19 are involved in disulfide bridge formation. Only cysteine at position 17 is present in all viruses analysed, therefore it seems likely that this is the most important residue. In the virus strains where cysteine 19 is also present, it is not known whether a second disulfide bridge is formed in the same dimer (linked by Cys 17-Cys 17) or with the other.

evident (table 1). Since the first human influenza A strain isolated in 1933, A/WS/33 (H1N1), until the most recently sequenced virus A/Guangdong/39/89 (H3N2), no amino acid change has been observed in the extracellular domain of the M2 protein. Two virus strains do not fit in this con principle the protective capacity of anti-M2 antibodies is already known. Experimental data demonstrated that a monoclonal antibody directed against the extracellular part of the M2 protein (14C2) can diminish the spread, although the infectivity of the virus in vitro was not reduced (Zebedee and Lamb, 1988). Furthermore it was demonstrated that passively administered monoclonal antibody (14C2) could inhibit viral replication in the lungs of mice (Treanor et al., 1990). Both approaches rely on the administration of anti-M2 antibodies. However, the passive administration of monoclonal antibodies is preferably avoided because of the immunogenicity of heterologous immunoglobulins which, upon repeated administration, can lead to the clearing of the antibodies from the body and thus to a reduction of the efficacy of the treatment. Even homologous antibodies can elicit anti-idiotype antibodies. Furthermore, it was found that humans infected with the virus do have anti-M2 antibodies but these do not protect against infection, (either their concentration or their nature are not sufficient to confer efficacy). This makes it unlikely that passive administration of anti-M2 antibodies is suitable for use in humans. It also teaches away from trying to develop vaccines for humans based on this antigen.

Recently, protection of mice against an infection with homologous or heterologous virus was described (Slepushkin et al., 1995). These authors used a formulation of incomplete Freund's adjuvant and a membrane extract of Sf9 cells expressing the complete M2 protein for immunizations. However, this approach is also not suitable for vaccination of humans because it relies on the use of Freund's adjuvant which is prohibited in humans.

In summary, use of antibodies for providing protection against influenza is preferably to be avoided. Moreover, it is unlikely that prophylactic treatment with antibodies will be effective in humans. Immunization with complete M2 protein in humans as described is not possible because it relies on incomplete Freund's adjuvant which cannot be used in humans, and is counter-indicated in higher animals.

It is thus the object of the invention to provide for an alternative influenza antigen that is sufficiently immunoprotective and is not dependent on Freund's adjuvant to find a use in humans.

According to the invention it has now been found that it is possible to prepare such a novel antigen that does not exist in nature. For this the extracellular part of a conserved influenza membrane protein or a functional fragment thereof is fused to a presenting carrier, for example a (poly)peptide. The conserved influenza membrane protein is for example the well conserved, extracellular part of the M2 protein. The membrane protein is preferably genetically fused to a presenting (poly)peptide as the presenting carrier, which (poly)peptide stabilises the extracellular part and surprisingly potentiates the immunogenicity of the fusion product thus obtained. It is thought that the presenting (poly)peptide brings the extracellular part into its wild type structure, thus presenting the antigen in a form that is also found on the virus and on the infected cells.

A 'functional fragment of the conserved influenza membrane protein' is a fragment that is capable of eliciting a statistically significant higher immunoprotection when administered in an immunoprotective dose to test members of a species than is found in control members of the same species not receiving the functional fragment.

In one embodiment of the invention the 23 amino acid extracellular part of the M2 protein is fused to the amino terminus of the human Hepatitis B virus core protein. In this way the wild type structure of the M2 protein in viral particles and on infected cells is mimicked, where the free N-terminus extends in the extracellular environment.

Alternative presenting (poly)peptides are multiple C3d domains (Dempsey et al., 1996), tetanus toxin fragment C or yeast Ty particles. 'Presenting (poly)peptides' are intended to encompass every stretch of amino acid(s) that can present the extracellular part, in a substantially wild type form, towards the environment.

Alternatively, the presenting carrier can be a non-peptidic structure, such as glycans, peptide mimetics, synthetic polymers, etc.

After expression of the novel antigen in a suitable acceptor cell, it can be used either as such (depending on the acceptor cell), as part of a membrane fragment or in isolated form.

The term 'presenting carrier' is used to indicate all types of presenting molecule, both (poly)peptides and others.

It will be clear for the person skilled in the art that a gene construct, comprising the coding information for the antigen and the presenting (poly)peptide, can not only be used to prepare the new antigen, as described above, but that it can also be used, optionally in the presence of suitable transcription and/or translation regulatory sequences, in a DNA vaccine, or in vaccinia based vaccine constructions.

A presenting (poly)peptide can be incorporated into the fusion product in a single copy or in multiple copies. The third complement protein fragment d (C3d) is preferably used in more copies, preferably 3.

In a preferred embodiment of the invention the fusion product further may comprise an additional peptide at an appropriate internal site (Schödel et al., 1992) or C-terminal (Borisova et al., 1989). This additional peptide is intended to further increase the protective capacity of the antigen, and may for example be a T helper cell epitope or a cytotoxic T cell epitope.

The antigen of the invention is obtainable by preparing a gene construct comprising a coding sequence for at least the extracellular part of a conserved influenza membrane protein or a functional fragment thereof and optionally the coding sequence for a presenting (poly)peptide operably linked thereto, optionally in the presence of suitable transcription and/or translation and/or secretion regulatory sequences, bringing this gene construct in a suitable acceptor cell, effecting expression of the gene construct in the acceptor cell and optionally isolating the antigen from the acceptor cell or its culture medium.

The presence of the transcription and/or translation and/or secretion regulatory sequences depends on whether the gene is to be integrated into a vector or the genome of the acceptor cell at a position already providing these signals.

The coding sequence for a presenting (poly)peptide is only present when the fusion product is a fusion between the antigen and a peptidic structure and if it is desirable to directly link the two structures in the DNA construct. In all other instances, the presenting carrier may be added to the antigen in a different manner.

The suitable acceptor cell can be selected from *E. coli, Lactococcus lactis, Lactobacillus plantarum*, yeast (e.g. *Pichia pastoris*). In the case of *L. lactis* the antigen need not be isolated but the engineered bacteria can be used directly for intranasal or oral use.

The invention further relates to vaccines that comprise at least the antigen of the invention. This antigen can be in isolated form or being part of a membrane fragment or being expressed on the acceptor cell. The antigen of the invention can be used together with suitable excipients. The person skilled in the art of vaccine design will be capable of selecting suitable excipients. Guidance may for example be found in Methods in molecular medicine: Vaccine Protocols (1996). Eds. Robinson, A., Farrar, G. H. and Wiblin, C. N. Humana Press, Totowa, N.J., USA.

The antigens of the invention may be used alone or in combination with one or more other influenza antigens, such as neuraminidase, haemagglutinin or native M2.

Furthermore, the invention relates to the use of the antigens in the preparation of a vaccine against influenza. The vaccines can be direct vaccines, i.e. vaccines containing the fusion products or indirect DNA vaccines. The latter are vaccines, comprising the fusion cDNA under the regulation of a eukaryotic promoter that can function in the recipient. The actual antigen is then produced in the recipient of the vaccine.

The vaccines of the invention are intended both for use in humans and in animals, for example pigs and horses of which it is known that they are infected by influenza A.

A similar approach as described here for preparing novel fusion antigens of influenza A can be adopted to prepare similar fusion antigens and vaccines containing the fusion antigens or DNA encoding the fusion antigens for influenza B and C.

The invention also relates to a method of preparing the antigens, comprising the steps of:

a) preparing a gene construct comprising a coding sequence for at least the extracellular part of a conserved influenza membrane protein or a functional fragment thereof and at least one coding sequence for a presenting (poly) peptide operably linked thereto, optionally in the presence of suitable transcription and/or translation and/or secretion regulatory sequences, b) bringing this gene construct in a suitable acceptor cell, c) effecting expression of the gene construct in the acceptor cell, and d) optionally isolating the antigen from the acceptor cell or its culture medium.

The invention will be further illustrated by the following example, that is in no way intended to limit the invention. The example extensively describes the preparation of fusion proteins of M2 with various presenting (poly)peptides and the use thereof in immunization. Instead of M2 and the presenting carriers described here, the skilled person will be capable of choosing another conserved influenza membrane protein and other presenting carriers.

The following abbreviations will be used:
1 $LD_{50}$: the viral challenge required to kill half of the population of infected mice
BCIP: 5-bromo-4-chloro-3-indolylphosphate
bp: base pair(s)
CIP: calf intestine phosphatase
C3d: complement protein 3 fragment d
DEA: diethylamine
HAU: haemagglutination units
hB2M: human β2-microglobulin
HBc: Hepatitis B core protein
IM2HBcm: universal influenza A M2 protein fragment fused to HBc
IPM2hB2Mm: influenza A M2 protein fragment (from A/PR/8/34) fused to hB2M
IPM2HBc: influenza A M2 protein fragment (from A/PR/8/34), fused to HBc, containing four additional amino acids between the first methionine and the start of the extracellular part of the M2 protein
IPM2HBcm: influenza A M2 protein fragment (from A/PR/8/34) fused to HBc
IPTG: isopropyl-β-D-thiogalactoside
m.a.: mouse adapted
M2C3d3: universal influenza M2 fragment fused to three copies of C3d
cM2C3d3: cytoplasmic form of M2C3d3
sM2C3d3: secreted form of M2C3d3
sM2C3d3X: form of M2C3d3 covalently attached in the cell wall
MES: 2-(N-morpholino)ethanesulphonic acid
MPLA: monophosphoryl lipid A
NBT: nitro blue tetrazolium
OmpA-ss: signal sequence of the outer membrane protein A
PCR: polymerase chain reaction
SDS-PAGE: sodium dodecylsulfate polyacrylamide gel electrophoresis
TDM: trehalose dicorynomycolate
phP: baculovirus polyhedron promoter
sgp67: secretion signal for the for the baculovirus gp67 protein

EXAMPLE

Introduction

This example demonstrates the preparation of various fusion antigens based on the influenza A virus M2 protein. The M2 fragment was fused to the amino terminus of various presenting carriers.

Materials and Methods

1. Bacterial Strains and Plasmids

All plasmid constructions, made for expression in *Escherichia coli*, were performed in strain MC 1061 (hsdR mcrB araD139Δ(araABC-leu)7697 ΔlacX74 galU galK rpsL thi (Casadaban and Cohen, 1980) because of high efficiency of transformation. The first transformation after mutagenesis was performed in WK6λmutS (Δ(lac-proAB), galE, strA, mutS::Tn10/lacI$^q$, ZΔM15, proA$^+$B$^+$; Zell and Fritz, 1987). Expression studies of human β$_2$-microglobulin and derivatives were performed in *E. coli* strain C3000 (Hfr, sup$^-$, thi(λ$^-$)). Expression studies of the Hepatitis B core protein and derivatives were carried out in MC1061 [pcI857].

pcI857 was described in Remaut et al., 1983b. A derivative of this plasmid pcI857K1 was described in Steidler et al., 1994.

The plasmid p714 (Parker and Wiley, 1989) was a kind gift of Dr. K. Parker and the plasmid pPLcA1 (Nassal, 1988) of Dr. M. Nassal. The plasmid pPLc245 was described in Remaut et al., 1983a.

For the constructions and expressions in *Lactococcus* lactis strain MG1363 (Gasson, 1983) was used. The vector for constitutive expression in *L. lactis*, pTREX1 (Wells and Schofield, 1996) was a generous gift from Dr. K. Schofield. The plasmid pL2MIL2, for the expression of interleukin 2, is described in Steidler et al., 1995. An analogous plasmid for the expression of interleukin 6, pL2MIL6, is described in Steidler et al., 1996.

The vector pSG5.C3d.YL (Dempsey et al., 1996) is a gift from Dr. Fearon.

2. Virus

A/PR/8/34 (H1N1) was adapted to mice by several lung passages. After adaptation, the virus was grown in eggs (Kendal et al, 1982) and purified over a sucrose gradient. The titer (haemagglutination units (HAU) (Hirst, 1941; Kendal et al, 1982) and the lethality in mice were determined. For m. a. A/PR/8/34, 1 $LD_{50}$ corresponded to 10 HAU present in 50 μl.

Influenza strain X-47 (H3N2) (Baez et al., 1980) was used in experiments for heterologous challenge. This strain was adapted to mice by several lung passages.

3. Animals

Female Balb/c mice were purchased from Charles River Wiga (Sulzfeld, Germany). The mice were used at the age of 6 to 7 weeks.

4. Antibodies

The monoclonal mouse antibody directed to the Hepatitis B core protein was a kind gift from Dr. Sc. H. Claeys (Bloedtransfusiecentrum, Leuven).

A mouse monoclonal antibody specific for the human $\beta_2$-microglobulin was purchased from Boehringer (Mannheim, Germany).

Alkaline phosphatase conjugated antibodies specific for mouse IgG or mouse IgG ($\gamma$ chain specific) were bought from Sigma Chemical Co. (St. Louis, Mo., USA).

5. Growth Media

E. coli was grown in LB medium (1% tryptone, 0.5% yeast extract and 0.5% NaCl) unless mentioned otherwise. The minimal M9 medium (Miller, 1972), supplemented with 0.2% casamino acids, was used in experiments when the expressed proteins were secreted into the growth medium and had to be purified.

M17 growth medium (Difco Laboratories, Detroit, Mich., USA)) supplemented with 0.5% glucose (GM 17) was used for culturing L. lactis. Erythromycin was used at a concentration of 5 μg/ml. L. lactis is grown at 28° C. without shaking.

The hybridomas and the myeloma cells were grown in RPMI 1640 (Gibco BRL, Bethesda, Md., USA) supplemented with 10% fetal calf serum, 0.3 mg/ml L-glutamine, 0.4 mM sodium pyruvate, 100 μl/ml penicillin and 100 ng/ml streptomycin.

5. Adjuvants

For the first immunization Ribi adjuvant (Ribi Immunochem Research Inc., Hamilton, Mont., USA) was used. A complete dose of Ribi adjuvant contains 50 μg MPLA (monophosphoryl lipid A), 50 μg TDM (trehalose dicorynomycolate), 2% squalene and 0.01% Tween 80. For the second and third immunization MPLA (Ribi Immunochem Research Inc., Hamilton, Mont., Usa) was used alone or mixed with an equal quantity of adjuvant peptide (Sigma Chemical Co., St. Louis, Mo., USA).

6. DNA Manipulations

Restriction enzymes, DNA polymerases, T4 polynucleotide kinase and T4 DNA ligase (Boehringer, Mannheim, Germany; Gibco BRL, Bethesda, Md. USA, or New England Biolabs, Beverly, Mass., USA) were used as recommended by the manufacturer. For analytical purposes, plasmid DNA was extracted according to Birnboim and Doly (1979). For preparative purposes, plasmid DNA was isolated according to Kahn et al. (1979). Restriction fragments of DNA were isolated by the Geneclean method according to Vogelstein and Gillespie (1979) and Struhl (1985). The required materials were purchased from Bio 101 (La Jolla, Calif., USA). For the isolation of plasmid DNA out of L. lactis, a pretreatment of the bacteria is necessary to weaken the cell wall. The bacterial pellet was resuspended in 50 μl TE (10 mM Tris-HCl pH 8-1 mM EDTA). Afterwards another 50 μl TE, supplemented with 10 mg/ml lysozyme (Boehringer, Mannheim, Germany) and 200 μl/ml mutanolysin (Sigma Chemical Co., St. Louis, Mo., USA) was added. This mixture was incubated for 10 min at 37° C. and then put on ice for 5 min. Further treatments are identical to those used for plasmid isolation out of E. coli.

For all constructions in L. lactis purified plasmid DNA (Qiagen, Hilden, Germany) were used. The DNA fragments were purified from agarose gels by using Qiaex II (Qiagen, Hilden, Germany).

7. PCR Amplification

All PCR reactions were carried out following a basic protocol. In each reaction about 50 ng pure template and 50 μmol sense and anti-sense oligonucleotides (Life Technologies, Paisley, UK) were used. Two units Vent$_R$® DNA polymerase (New England Biolabs, Beverly, Mass., USA) were added after heating of the samples to 94° C. The annealing temperature ($T_a$) was set, according to the composition of the primer, at about 7° C. below the melting temperature ($T_m$). In these PCR amplifications the best results were obtained at 60° C. The synthesis of hbc and the fusion genes ipm2hbc and im2hbc, was carried out for 45 seconds at 72° C. The synthesis of the sequence, coding for the extracellular part of the M2 protein (cm2 and sm2), was left for 20 seconds at 72° C. A total of thirty amplification rounds were performed. The control reactions did not contain oligonucleotides. Three different concentration of MgSO$_4$ were used, 2, 3 and 4 mM. The PCR reaction that produced a significant amount of the expected fragment under the most stringent conditions (lowest Mg$^{2+}$ concentration and highest $T_m$) was used for further cloning.

The C3d3 fragment was amplified from pSG5.C3d.YL with the oligonucleotides C3ds and C3da using Pwo DNA Polymerase (Boehringer, Mannheim, Germany). The annealing temperature was set at 60° C. and the synthesis was performed for 2 min at 72° C.

8. Ligation

The ligations for L. lactis were performed with Ready-To-Go™ T4 DNA Ligase (Pharmacia Biotech, Uppsala, Sweden). After incubation for 1 h at 20° C., the mixture was extracted with phenol (Life Technologies, Paisley, UK) and chloroform/iso-amyl alcohol (24/1). The DNA was precipitated with see-DNA (Amersham International, Buckinghamshire, UK). The complete resuspended pellet was used for electroporation (Wells et al., 1993).

9. Protein Purification Media

All chromatography media were purchased from Pharmacia Biotech (Uppsala,Sweden), except CF11 cellulose, which was purchased from Whatman International Ltd. (Maidstone, UK).

10. Protein Gel

Protein samples were analysed by SDS-polyacrylamide gel electrophoresis (SDS-PAGE) according to Laemmli, 1970. After electrophoresis, the proteins were fixed with 10% trichloroacetic acid and stained with 0.05% Coomassie brilliant blue R-250 in destain. Excess dye was removed by incubating the gel in destain (30% methanol-7% acetic acid). The gel was soaked in 40% ethanol before it was dried between two sheets of permeable cellophane.

11. Western Blot and Dot Blot

For immunological characterisation, proteins were electrophoretically transferred from a SDS-PAGE-gel onto a nitrocellulose membrane (pore diameter 0.45 μm, Schleicher & Schuell, Dassal, Germany) with a dry blotting apparatus (Plexi-labo, Gent, Belgium). The filter was blocked for at least 2h in PBS pH 7.4 (14.5 mM phosphate buffer pH 7.4-150 mM NaCl) with 2.5% skim milk powder and 0.1% Triton X-100 (blocking buffer). Incubation with the primary antibody, diluted in blocking buffer, was carried out at room temperature for 30 to 60 min. Excess of unbound antibody was removed by three washings with blocking buffer. The bound antibodies were detected with an alkaline phosphatase conjugated antibody of the appropriate specificity. Subsequently, the filter was washed two times with PBS pH 7.4-0.1% Triton X-100. A third washing step was carried out with substrate buffer (100 mM Tris-HCl pH 9.5-100 mM NaCl-5 mM MgCl$_2$). The filter was then incubated in substrate buffer with 165 μg/ml nitro blue tetrazolium (NBT) and 165 μg/ml 5-bromo-4-chloro-3-indolylphosphate (BCIP) until a clear signal appeared. The blot was finally washed thoroughly with tap water and dried.

The dot blot analysis was carried out in a similar way as the Western blot, except that the proteins were not transferred through electrophoresis, but by filtering the samples through a nitrocellulose membrane.

12. ELISA

In every ELISA we used a 0.1% casein solution for blocking and for the dilution of the antibodies used. The stock solution of casein (2.5%) was prepared as follows: 6.25 g casein powder was dissolved in 200 ml 300 mM NaOH by overnight stirring at 37° C. The pH was adjusted to 7.0 by adding 2N HCl. The final volume was brought to 250 ml (Nunc bulletin no. 7, December 1989). Sodium azide (0.02%) was added as a preservative.

Different ELISA's were developed to determine the concentration of Hepatitis B core or human β2-microglobulin fusion protein. Microtiter plates (type II F96 maxisorp Nunc A/S, Roskilde, Denmark) were coated for 1.5 h at room temperature or overnight at 4° C. with a 1/2 dilution series of samples containing IPM2HBcm or IPM2hB2Mm. On the same plate, a 1/2 dilution series of purified HBc or hB2M, respectively, starting from 2 μg/ml, was used as a standard. Between every incubation step, the plates were washed twice with tap water and once with PBS, pH 7.4-0.05% Triton X-100, except that after blocking, the plates were not washed. The microtiter plates were blocked with 0.1% casein solution for 2 h at room temperature or at 4° C. overnight. As primary antibody we used mouse anti-HBc or mouse anti-hB2M, respectively. The bound antibodies were detected with an alkaline phosphatase labelled anti-mouse IgG (γ chain specific) antibody. The incubation with antibody solution was carried out at room temperature for 1.5 h. Finally the microtiter plates were incubated for 1 h with substrate buffer (10% diethanolamine—0.5 mM $MgCl_2$—0.02% $NaN_3$ pH 9.8) containing 1 mg/ml p-nitrophenyl phosphate. The absorbance was measured at 405 nm and the wave length of 490 nm was used for normalization.

13. Preparation of Polyclonal Anti-M2

All mice, which had been immunized with IPM2HBcm and had survived the lethal challenge with m. a. A/PR/8/34 influenza A virus (see results, immunization) were anaesthetized with 250 μl 25 mg/ml tribromoethanol (injected i.p.) and blood samples were taken by heart puncture. The serum was isolated as described hereinbelow. The crude serum gave a high background in Western blot, therefore an IgG fraction was prepared. The crude serum was filtered through a 0.45 μm filter (Millipore Millex-HV, Millipore, Bedford, Mass., USA) and diluted 10 times in loading buffer (PBS—10 mM EDTA pH 8). This mixture was loaded on an equilibrated Protein G Sepharose 4 Fast Flow column (φ=1 cm, h=8 cm). The bound IgG molecules were eluted with 100 mM glycine-HCl pH 2.7. Fractions of 1 ml were collected in tubes containing 50 μl 1 M Tris-HCl pH 9.5 to bring the pH to neutral.

The quantity of anti-M2 antibodies in the pooled peak fractions was 2.6 μg/ml. This was determined in an ELISA, comparable to the detection of anti-M2 antibodies in the serum of immunized mice. Mouse monoclonal anti-human $β_2$-microglobulin (Cymbus Bioscience, Southampton, UK) was used as a standard.

14. Serum Preparation

Five blood samples were taken from every mouse: the pre-immune serum (a), the serum taken after the first (b), after the second (c) and after the third (d) immunization, and the serum taken after challenge (e). This blood was incubated for 30 min at 37° C. The samples were then placed on ice for at least 1 hour and centrifuged two times 5 min at 16000 g in a microcentrifuge. The serum was isolated. Equal volumes of sera obtained from different mice were pooled for the analysis of antibody production.

15. List of Plasmids 15.1 *E. Coli* pATIPM2 ml: plasmid that contains the uninterrupted m2 gene from A/PR/8/34 pIPM2hB2Mm2s2: plasmid for the expression of IPM2hB2Mm, with the correct amino terminus of M2 pPLcIPM2HBc: expression plasmid for IPM2HBc, with four amino acids between the initiating methionine and the amino terminus of M2e pPLcIPM2HBcm: expression plasmid for IPM2HBcm, with the correct amino terminus of M2e. Sequence of M2 is derived from A/PR/8/34 pPLcIM2HBcm: expression plasmid for IM2HBcm, with the correct amino terminus of the universal M2

15.2 *L. Lactis* pT1TT: plasmid for the expression of TTFC pT1PM2LTT: expression of IPM2TT, with leucine codons adapted for *L. lactis*. Sequence of M2e is derived from A/PR/8/34 pT1PM2LTTIL2: expression of IPM2TT, with adapted leucine codons, in combination with mIL2 pT1PM2LTTIL6: plasmid for the expression of IPM2TT, with adapted leucine codons, in combination with mIL6 pT1HBc: plasmid for the expression of HBc pT1HBcIL2: expression of HBc in combination with mIL2 pT1HBcIL6: expression of HBc in combination with mIL6 pT1PM2HBc: plasmid for the expression of IPM2HBcm. Sequence of M2e is derived from A/PR/8/34 pT1PM2HBcIL2: expression of IPM2HBcm in combination with mIL2 pT1PM2HBcIL6: expression of IPM2HBcm in combination with mIL6 pT1M2HBc: plasmid for the expression of IM2HBcm, with the universal sequence for M2e pT1M2HBcIL2: expression of IM2HBcm in combination with mIL2 pT1M2HBcIL6: expression of IM2HBcm in combination with mIL6 pT1PM2LHBc: plasmid for the expression of IPM2HBcm, with leucine codons adapted for *L. lactis* pT1PM2LHBcIL2: expression of IPM2HBcm, with adapted leucine codons, in combination with mIL2 pT1PM2LHBcIL6: expression of IPM2HBc, with adapted leucine codons, in combination with mIL6 pT1M2LHBc: expression of IM2HBcm, with leucine codons adapted for *L. lactis* pT1M2LHBcIL2: expression of IM2HBcm, with adapted leucine codons, in combination with mIL2 pT1M2LHBcIL6: expression of IM2HBcm, with adapted leucine codons, in combination with mIL6 pT1cM2L: plasmid for the expression of the cytoplasmic form of M2e, with leucine codons adapted for *L. lactis* pT1cM2LC3d: expression of cM2LC3d, with adapted leucine codons pT1cM2LC3d3: expression of cM2LC3d3 (with three consecutive C3d domains), with adapted leucine codons pT1sM2LX: plasmid for the expression of the secreted and anchored form of M2e, with leucine codons adapted for *L. lactis* pT1sM2LC3d: expression of sM2LC3d, with adapted leucine codons pT1sM2LC3d3: expression of sM2LC3d3 (with three consecutive C3d domains), with adapted leucine codons Experimental Section 1. Construction of pATIPM2m The RNA segment 7 of the influenza A virus, A/PR/8/34 (H1N1), was cloned by a procedure as described for RNA segment 4 in Min Jou et al., 1980. The resulting plasmid was named pATIPMA and is commercially available (LMBP catalogue 1992, no. 1774).

The mRNA of the M2 protein is not a colinear transcript of RNA segment 7. Indeed, an intron of 689 nucleotides had to be removed (Lamb et al., 1981).

In the plasmid pATIPMA, StuI cuts after the first nucleotide of the second exon (see FIG. 1a). This nucleotide was included in the synthetic oligonucleotides, that were used to code for the first exon. The synthetic first exon, encoding the amino-terminus of the mature M2 protein, was designed to contain a single stranded GATC overhang at its 5' end. This allowed us to make the connection to a preceding BamHI site in the vector pATIPMA and to replace the original first exon.

Furthermore codon usage was optimized for expression in E. coli.

Next, we introduced, by site-directed mutagenesis (Stanssens et al., 1989), a BclI site at the junction between the extracellular part and the membrane anchoring region of the M2 protein (see FIG. 1b). The amino acid sequence of the extracellular part was not changed. The resulting plasmid, pATIPM2 ml, carries the uninterrupted m2 gene of A/PR/8/34.

2. Construction of IPM2hB2Mm

Parker and Wiley (1989) expressed human β2-microglobulin in the periplasm of E. coli by making use of the plasmid p714. This plasmid contains the coding region for β2-microglobulin preceded by the signal sequence of the outer membrane protein A of E. coli (OmpA-ss) (see FIG. 2a). The OmpA signal sequence is required for the translocation of the protein, to which this sequence is fused, to the periplasm. The signal sequence is cleaved off after transport. On plasmid p714, human β2-microglobulin is under control of both the lipoprotein (lpp) and lacUV5 promoter. Addition of 1 mM IPTG to a mid-log phase culture leads to the production of β2-microglobulin.

The coding sequence of the extracellular part of the M2 protein, isolated as a BamHI-BclI fragment from pATIPM2 ml, was inserted between the signal sequence of ompA and the human β2-microglobulin (for details see FIG. 2a). Due to the construction, there were 9 additional nucleotides between the end of the ompa signal sequence and the beginning of the m2 fragment, which had to be removed (see FIG. 2b). This was done by looping out mutagenesis according to Nakamaye and Eckstein, 1986. As a result, the plasmid pIPM2hB2Mm2s2 was obtained.

3. Localisation of the IPM2hB2Mm

A freshly grown preculture of C3000 containing p714 or pIPM2hB2Mm2s2 was diluted 1/100 in LB with ampicillin. As described above, the hb2m and ipm2hb2mm genes are under control of the lacUV5 promoter. When the cultures reached a density of about $5.5 \times 10^8$ bacteria/ml, they were divided in two and one half of each culture was induced with 1 mM IPTG. After 3 h induction, the bacteria were harvested and fractionated. The periplasm of the bacteria was isolated by osmotic shock (Neu and Heppel, 1965). The remainder of the bacteria was sonicated (Vibra cell, Sonics & Materials Inc., Danbury, Conn., USA) and centrifuged for 10 min at 16000g, to isolate the cytoplasm. The different samples were analyzed on a SDS 15% PAGE-gel. Human B2M and the fusion protein IPM2hB2Mm were transported to the periplasm, whereas the precursors, where the signal sequence was still present, remained associated with the bacteria (data not shown). Determination of the amino-terminus of the mature IPM2hB2Mm (by courtesy of Dr. J. Vandekerckhove) by automated Edman degradation on a model 470A gas-phase sequencer coupled to a model 120A on-line phenylthiohydantoin amino acid analyser (Applied Biosystems, Foster City, Calif., USA), demonstrated that the OmpA signal sequence was correctly cleaved off.

4. Purification of IPM2hB2Mm

The fusion protein IPM2hB2Mm could efficiently be expressed in the periplasm of E. coli. Whereas performing an osmotic shock is a critical procedure, especially on large volumes, Steidler et al. (1994) previously described an elegant system, based on the controlled expression of the Kil protein, to release periplasmic proteins in the growth medium.

The kil gene is present on a compatible plasmid under the tightly regulated $P_L$ promoter, the leftward promoter of phage λ (Remaut et al, 1981). The plasmid pcI857K1 also carries the temperature sensitive repressor of the $P_L$ promoter, cI857. The fusion protein IPM2hB2Mm is synthesized upon induction with 1 mM IPTG and at the end of the production phase, the culture is switched from 28° C. to 42° C. to induce kil.

A fermentation (BioFlo IV fermentor, New Brunswick Scientific Co., Edison, N.J., USA) was carried out using the standard induction procedure described above. The culture was centrifuged in a contifuge 17RS (Heraeus Instruments, Hanau, Germany) at 11000g and the growth medium was isolated. The sodium chloride concentration of the growth medium was adjusted to 300 mM and buffered with 20 mM MES (2-(N-morpholino)ethanesulphonic acid), pH 6.5. This solution was loaded on a DEAE Sephacel column ($\phi$=5 cm, h=6.5 cm), equilibrated with 20 mM MES, pH 6.5-300 mM NaCl. Under these conditions IPM2hB2Mm did not bind to the matrix. The ammonium sulfate concentration of the flow through was brought to 0.8 M with a 3.8 M $(NH_4)_2SO_4$ solution, pH 7. The mixture was loaded on a Phenyl Sepharose column ($\phi$=5 cm, h=17 cm), equilibrated in 20 mM Tris-HCl, pH 7.5 0.8 M $(NH_4)_2SO_4$. A decreasing ammonium sulfate concentration gradient starting from 0.8 M and going to 0, did not release the bound fusion protein. This was achieved by eluting the column with a pH gradient from 20 mM Tris-HCl, pH 7.5 to 5 mM NaAc, pH 5.5. The peak fractions were pooled and diluted ten times in 20 mM diethylamine (DEA), pH 8.5.

The complete mixture was loaded on a Sepharose Q column ($\phi$p=0.8 cm, h=2.3 cm), equilibrated with 20 mM DEA, pH 8.5. The protein was eluted from the column with a salt gradient from 0 to 1M. The peak fractions were pooled and loaded on a Sephacryl S-100 gel filtration column ($\phi$=1.5 cm, h 47 cm). Only one peak with the expected molecular weight of about 15 kDa was observed. This purified IPM2hB2Mm was used to immunize mice for preparing hybridomas, secreting monoclonal antibodies directed against the M2 protein.

5. Production of Monoclonal Antibodies to the M2 Protein

Balb/c mice were immunized three times with 2.5 µg purified IPM2hB2Mm. For the first injection a complete dose of Ribi adjuvant was used. The second and third immunizations were performed in the presence of 50 µg MPLA. The injections were given with an interval of three weeks. Three days after the last immunization, spleen cells were isolated and fused with myeloma cells SP2/0-AG14 using standard protocols (Köhler and Milstein, 1975). Supernatants from different immunoglobulin producing cell clones were tested in ELISA and Western blot for reactivity against the other fusion protein IPM2HBcm (described further). The Hepatitis B core protein alone was used as a control to eliminate false positive clones. The isotype of the antibody was determined (Isostrip, Boehringer, Mannheim, Germany). Two different immunoglobulin subtypes that recognized the extracellular part of the M2 protein were obtained, an IgM and an IgG2a. Especially the IgG2a antibody was used in further experiments.

6. Expression of HBc and IPM2HBcm

Expression of proteins under control of the $P_L$ promoter was performed by shifting an exponentially growing culture from 28° C. to 42° C. (Remaut et al., 1981). A saturated preculture of MC1061 [pcI857] containing the plasmid pPLc245 (control), pPLcA1 (carrying the hbc gene) or pPLcIPM2HBcm (containing the fusion gene ipm2hbc) respectively, was diluted 1/100 in LB medium (50 µg/ml kanamycin and 100 µg/ml ampicillin) and grown for about 4 h at 28° C. under shaking. When the cultures reached a density of $4.5 \times 10^8$ to $5.5 \times 10^8$ bacteria/ml, they were split, one half was incubated for 4 h at 28° C., the other half was switched to 42° C. The bacteria were concentrated by centrifugation (2 min at 16000g in a microcentrifuge).

The culture medium was removed and the bacteria were resuspended in TE buffer (10 mM Tris-HCl—1 mM EDTA, pH 7.6). The bacteria were opened by sonication (Vibra cell, Sonics & Materials Inc., Danbury, Conn., USA) and the bacterial debris were pelleted for 10 min at 16000 g in a microcentrifuge. The supernatant was isolated and the pellet was resuspended in TE buffer. The samples were analysed on a SDS 12.5% PAGE-gel, in a Western blot and on a dot blot.

7. Large Scale Production of IPM2HBcm

The strain MC1061 [pcI857, pPLcIPM2HBcm] was grown in a BioFlo IV fermentor (New Brunswick Scientific Co., Edison, N.J., USA). When the culture reached a density of about $5.5 \times 10^8$ cells/ml, the temperature was increased to 42° C. After three hours of induction, the culture was centrifuged in a contifuge 17RS (Heraeus Instruments, Hanau, Germany) at 11,000g. The bacteria were collected and resuspended in a volume (in ml) buffer (50 mM Tris-HCl pH 8-150 mM NaCl-5% glycerol with one protease inhibitor cocktail tablet (Complete™; Boehringer, Mannheim, Germany) per 25 ml) corresponding to two times the weight (in g) of the pelleted bacteria. This suspension was treated with 1 mg/ml lysozyme (freshly dissolved in 25 mM Tris-HCl pH 8) for half an hour on ice. Subsequently, the bacteria were lysed with 0.2% Triton X-100 in the presence of 25 mM EDTA, pH 8. After 30 min incubation on ice, the lysates were centrifuged for 1 h in a Sorvall SS-34 rotor (Du Pont Company, Wilmington, Del., USA) at 48000 g. The supernatant was removed and used for purification of IPM2HBcm.

8. Immunization with IPM2HBcm

Balb/c mice were injected three times intraperitoneally with purified IPM2HBcm in the presence of adjuvant. Control mice received only PBS buffer, pH 7.4 and adjuvant. For the first immunization half a dose of Ribi adjuvant was used. In the second and third injection we used 25 µg MPLA and 25 µg MDP.

Mice were immunized intranasally three times by applying a light ether anesthesia, after which 50 microliter antigen solution in PBS buffer (containing either 10 microgram IPM2HBcm or IM2HBcm without any adjuvant) is put in the nostril.

9. Expression in *L. Lactis*

Single colonies from *L. lactis* strain MG 1363, containing the plasmid pT1HBc, pT1PM2HBc or pT1M2HBc, respectively or the derivatives with mIL2 (pT1HBcIL2, pT1PM2HBcIL2 and pT1M2HBcIL2) or mIL6 (pT1HBcIL6, pT1PM2HBcIL6 and pT1M2HBcIL6), were inoculated in 10 ml GM17E each. MG1363 [pTREX1] was used as control. The bacteria were grown for about 16 h at 28° C. The cells were collected by centrifugation at 2000g for 20 min (Sorvall 11 RT6000 D). The growth medium was isolated and the bacteria were resuspended in 250 µl TE. Following resuspension, an additional 250 µl TE supplemented with 10 mg/ml lysozyme and 200 u/ml mutanolysin was added. This mixture was incubated for 10 min at 37° C. and then put on ice for 5 min. Then 500 µl Laemmli sample buffer (100 mM Tris-HCl pH 6.8—5% SDS—1.2M β-mercaptoethanol—0.008% bromophenol blue—16% glycerol) was added and the samples were boiled for 5 min. An equivalent of 1 ml original culture volume, or $10^9$ bacteria was analyzed on a SDS 12.5% PAGE-gel. The production of mIL2 or mIL6 in the culture supernatant was evaluated in a bio-assay based on the proliferation of CTLL2-cells (mIL2, Gillis et al., 1978) or the proliferation of a B-cell hybridoma, 7TD1 (mIL6, Van Snick et al., 1986).

Results

1. Construction of IPM2HBcm

Figure 3B:
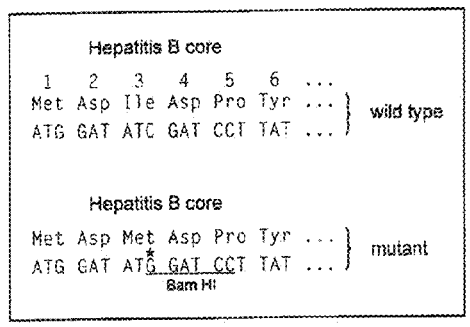
FIG. 3: Construction of pPLcIPM2HBcm.
Ori=origin of replication,
Cat=chloramphenicol acetyltransferase
Bla=β-lactamase,
HBc=hepatitis B core,
ssDNA=single-stranded DNA,
M2e=extracellular part of the M2 protein.
(a) Plasmid construction flow scheme, FIG. 3a2 mutator [SEQ ID NO:16], FIG. 3a4 mutator [SEQ ID NO:17], FIG. 3a4 selection [SEQ ID NO:18],
(b) Sequence around the introduced BamHI restriction site in the hepatitis B core gene that includes paired oligonucleotide and encoded amino acid sequences of SEQ ID NOs:52-55 (FIG. 3b),
(c) Details of key sequences that include paired oligonucleotide and encoded amino acid sequences of SEQ ID NOs:56-61 (FIG. 3c).
Figure 3C:
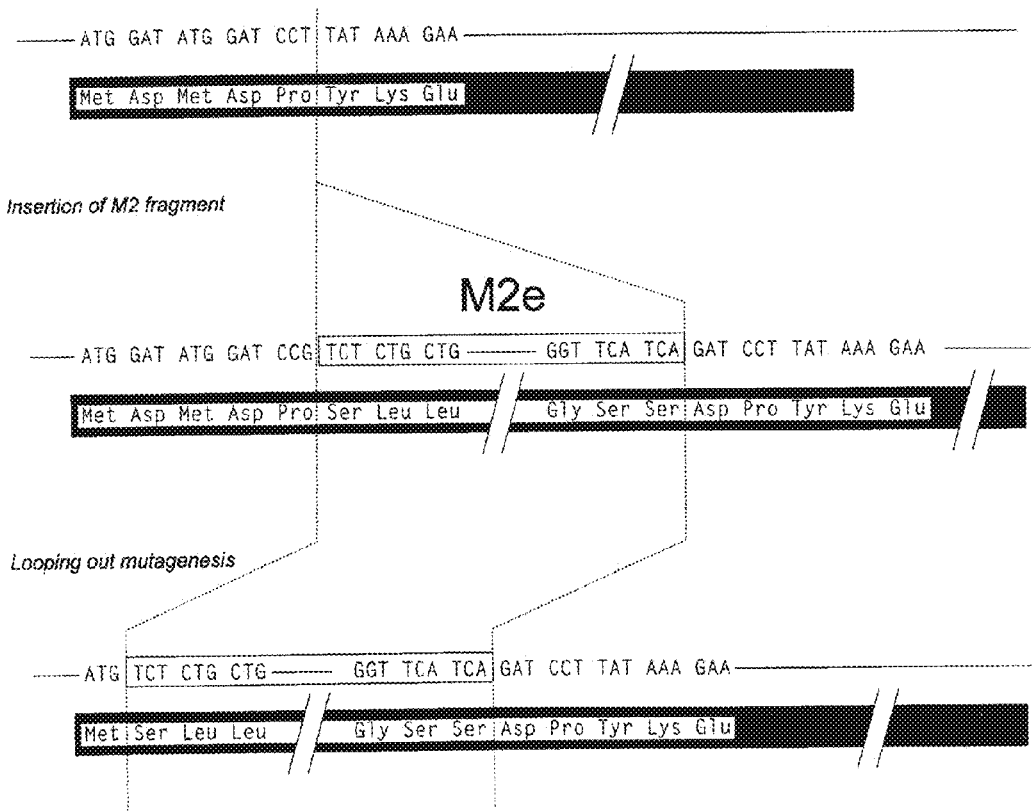

The plasmid pPLcA1 (see FIG. 3a) contains the hepatitis b core (hbc) gene under control of the $P_L$ promoter of bacteriophage λ (a gift from Dr. Nassal). The 346 by NcoI-XbaI HBc fragment, isolated from pPLcA1, was inserted into the NcoI and XbaI opened pMa581, a derivative of pMa58. This plasmid was called pMaHBc. At the 5' end of the hepatitis B core, directly following the start codon, we introduced a BamHI site by site-directed mutagenesis (Stanssens et al., 1989), correctly positioned in the reading frame of HBc (for details see FIGS. 3a and b). The resulting plasmid was named pMaHBcm. The information coding for the extracellular part of the M2 protein was cloned as a 72 by BamHI-BclI fragment, derived from pATIPM2m1, into the BamHI opened pMaHBcm, resulting in the vector pIPM2HBc. The hbc gene in the expression vector pPLcA1 was then replaced by the 418 by NcoI-XbaI m2hbc fragment, creating pPLcIPM2HBc. Due to the construction, four amino acids extra were present between the first methionine and the start of the extracellular part of the M2 protein and had to be removed (see FIG. 3c). This was done by looping out mutagenesis (Deng and Nickolov, 1992). The resulting plasmid was named pPLcIPM2HBcm (see FIGS. 3a and c).

2. Expression of the Fusion Protein

The plasmids pPLc245 (control), pPLcA1 (hbc gene) and pPLcIPM2HBcm (ipm2hbc gene) were transformed to MC1061 [pcI857]. After culture and induction the bacteria were lysed by sonication. The lysates were centrifuged and an aliquot of the supernatants was loaded on a SDS 12.5% PAGE-gel (see FIG. 4). The same fractions were also analysed by a Western blot. Two different monoclonal antibodies were used: an antibody specific for the Hepatitis B core protein and a monoclonal antibody (IgG2a) directed against the extracellular part of the M2 protein.

Figure 5:
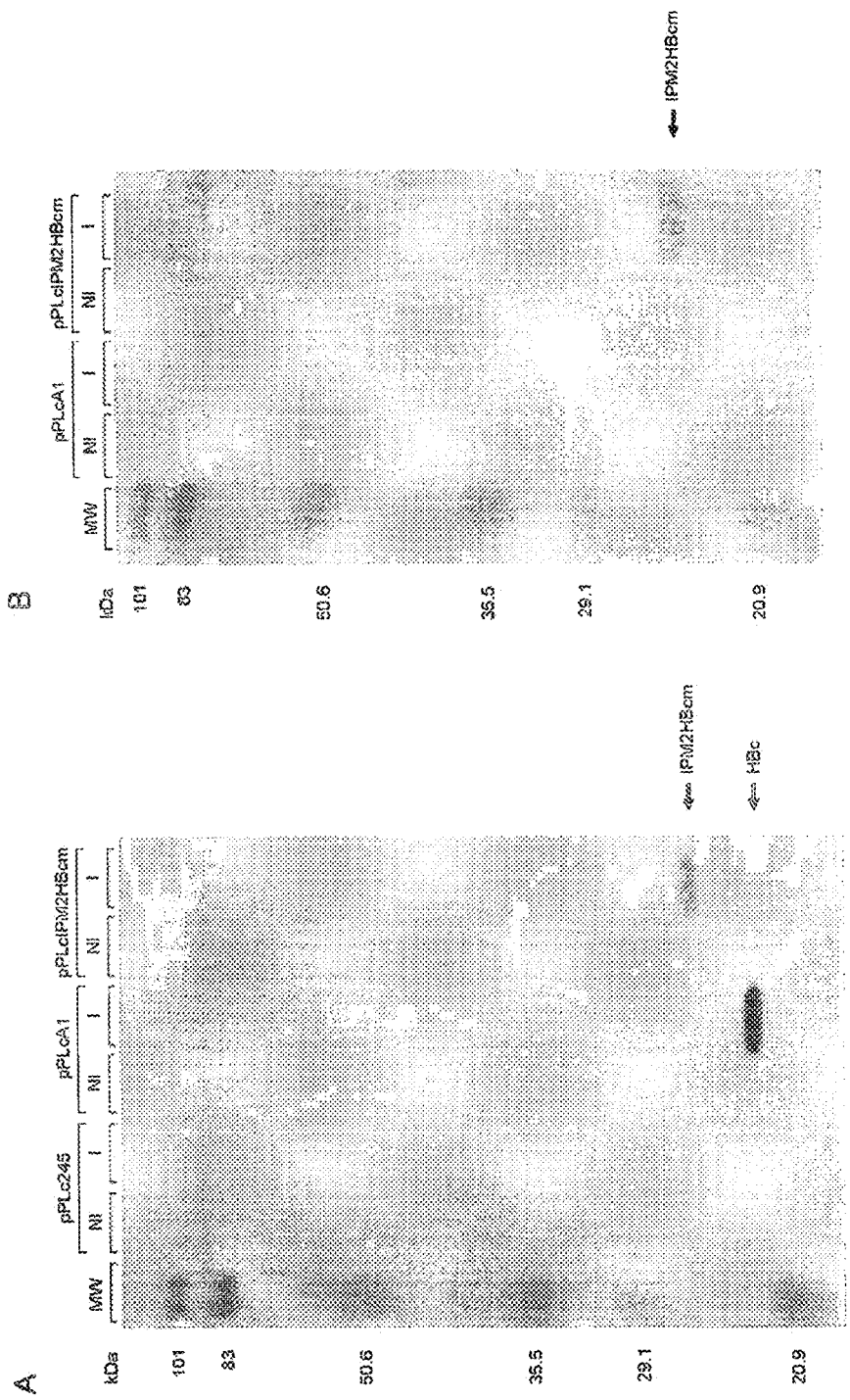
FIG. 5: Analysis of the soluble fraction, corresponding to 150 μl original culture, of strain MC1061[pcI857] transformed with pPLc245 (control), pPLcA1 (expression of HBc)

The monoclonal antibody against Hepatitis B core reveals two different bands (see FIG. 5A), one corresponding to the Hepatitis B core protein and the other to the fusion protein. The latter protein has a lower mobility, corresponding to the insertion of the extracellular domain of the M2 protein. The presence of the M2 fragment was confirmed by using the antibody specific for the extracellular part of the M2 protein (see FIG. 5B).

The N-terminal amino acid sequence of IPM2HBcm was determined (Dr. J. Vandekerckhove) by automated Edman degradation on a model 470A gas-phase sequencer coupled to a model 120A on-line phenylthiohydantoin amino acid analyzer (Applied Biosystems, Foster City, Calif., USA). This analysis revealed the N-terminal sequence Ser Leu Leu, which is exactly the same as the amino terminal sequence of the M2 protein of the influenza A virus (FIG. 6). The first amino acid, methionine, was removed in *E. coli*. The amino-terminus of the fusion protein thus corresponds to that of the wild type M2 protein (table 1; Lamb et al., 1985).

Hepatitis B core, also when expressed in *E. coil*, spontaneously associates to form particles, indistinguishable from the viral core particles circulating in the blood of Hepatitis B infected patients (Cohen and Richmond, 1982). Clarke and co-workers (1987) showed that a peptide inserted at the amino terminus of the Hepatitis B core protein could be detected at the surface of the particle.

Electron micrographs (Dr. G. Engler) showed that the IPM2HBcm fusion protein was able to form similar particles. To investigate whether the insertion of the extracellular part of the M2 protein resulted in the surface localization of this fragment, soluble fractions, containing HBc or IPM2HBcm, were loaded on a nitrocellulose membrane in a dot blot. The dot blots were treated with a monoclonal antibody directed against HBc or against M2. FIG. 7 clearly shows a signal in the soluble pPLcIPM2HBcm fraction, when revealed with the antibody directed against the M2 protein (panel B). Since the soluble fraction is loaded in a native state onto the nitrocellulose membrane, we conclude that the epitope is located at the surface of the Hepatitis B core particle.

3. Purification of IPM2HBcm

The bacterial lysates were prepared as described in Materials and methods. The concentration of Tris-HCl pH 8 and NaCl were adjusted to 20 mM and 50 mM respectively. This mixture was loaded on a DEAE Sepharose column ($\phi$=2.5 cm, h=5.5 cm), equilibrated with 20 mM Tris-HCl, pH 8-50 mM NaCl. The fusion protein was not retained on the column. To the flow through 3.8 M $(NH_4)_2SO_4$, pH 7 was added to a final concentration of 1.2 M. This mixture was incubated under stirring in the cold room during 16h. The precipitate was removed over a CF11 cellulose column ($\phi$=2.5 cm, h=3.5 cm). The column was eluted with PBS, pH 7.4. The eluate of about 50 ml was concentrated in a Centiprep 30 (Amicon Corporation, Danvers, Ill., USA) to 5 ml and loaded on a Sephacryl S-300 column ($\phi$=2.5 cm, h=91 cm), which was equilibrated with PBS, pH 7.4. The peak fractions were pooled and the concentration of IPM2HBcm was determined in an ELISA. The LPS content was assayed (LAL Coatest® Endotoxin purchased from Endosafe Inc., Charleston, S.C., USA) and was sufficiently low (5 to 9 ng/50 μg IPM2HBcm) not to interfere with immunization.

4. Immunization

The purified preparation of IPM2HBcm particles was used to immunize 7 weeks old female Balb/c mice. Four different groups of 12 mice were evaluated. The first group received 50 μg IPM2HBcm, the second 10 μg, the third 5 μg and the fourth a control group, only received buffer with adjuvant. A total of three injections were given with the appropriate adjuvant. The injections were administered with three weeks interval. Three weeks after the last inoculation, the mice were challenged with 5 $LD_{50}$ m.a. A/PR/8/34. The virus was administered intranasally in a total volume of 50 μl after ether anesthesia. Morbidity was followed by measuring rectal temperature (FIG. 8 A1) and weight (FIG. 8 A2) every other day.

All mice immunized with IPM2HBcm showed a significant degree of protection against the following influenza challenge. Depending on the administered dose, 9 to 11 mice out of 12 survived the influenza infection, versus only 2 out of 11 for the control group (see FIG. 8B).

5. Analysis of the Serum Samples

One day prior to the first (bleeding a) and two weeks after every injection (bleeding b, c and d) blood samples were taken. Three weeks after the challenge, when the mice had recovered sufficiently from the influenza infection, a last blood sample (e) was taken. The serum was analyzed in an ELISA (see Materials and Methods) to identify IgG antibodies directed towards the extracellular part of the M2 protein. To do so, we made use of the other fusion protein, IPM2hB2Mm. One half of the microtiter plate was coated with human $\beta_2$-microglobulin, the other half was coated with the fusion protein IPM2hB2Mm, both as unpurified culture supernatant. The concentration of IPM2hB2Mm used was 1 μg/ml. The same concentration of total protein was used in both set ups. Therefore, the hB2M content of the culture supernatant of bacteria expressing hB2M had to be adjusted to 1 μg/ml by adding purified hB2M (Sigma Chemical Co., St. Louis, Mo., USA). Dilution series (1/3) of the different serum samples, starting from 1/50, were loaded on the hB2M and IPM2hB2Mm, coated wells. The ELISA was further developed as described in Materials and methods.

To obtain the value for the specific reactivity towards the extracellular part of the M2 protein, the absorbance of hB2M at a given dilution was subtracted from the absorbance of IPM2hB2Mm of the corresponding dilution. FIG. 9 clearly demonstrates a high antibody response to the extracellular part of the M2 protein, in the mice which received three injections with the vaccine. The titer in the serum was further increased after the challenge.

6. Construction of IM2HBcm

It is the aim of the present invention to make a universal vaccine against influenza A viruses. In the vaccination studies described above, we showed protection against the influenza virus from which the original M2 sequence was derived, A/PR/8/34 (homologous protection). The extracellular part of the M2 protein from this virus differs from most other viruses sequenced to date, by only one amino acid (see table 1). Therefore, a construct was made in which the glycine at position 20 was changed to aspartic acid.

To do so we made use of an intermediate vector in the construction of pPLcIPM2HBcm, pMaIPM2HBc2 (see Figure). The plasmid pMaIPM2HBc2 does not yet contain the mutated $\overline{m2}$ (deletion of 12 extra nucleotides) fragment, which starts at the first mature codon of the M2 protein. Therefore this fragment was isolated from pPLcIPM2HBcm by cutting with SgrAI and EcoRI. This 499 by SgrAI-EcoRI fragment was cloned into the SgrAI and EcoRI opened vector pMaIPM2HBc2, which resulted in the construction of pMaIPM2HBc3 (see FIG. 10).

By site-directed mutagenesis according to Deng and Nickoloff (1992) the sequence of the extracellular part of the M2 protein was changed to the more universal M2 sequence (Gly20->Asp). The new plasmid was called pIM2HBcm. The sequence was determined on a model 373A sequencer (Applied Biosystems, Foster city, Calif., USA) and shown to contain the desired mutation. The mutated m2 fragment was isolated from pIM2HBcm as a 499 by SgrAI-EcoRI fragment and reintroduced into the expression vector pPLcIPM2HBcm, opened with SgrAI and EcoRI, to create pPLcIM2HBcm.

7. Expression of IM2HBcm

Strain MC1061 [pcI857] containing respectively pPLc245, pPLcA1, pPLcIPM2HBcm or pPLcIM2HBcm was cultured as described in the Experimental Section. The bacteria were collected and opened by sonication. The soluble fraction was isolated and the concentration of Hepatitis B core protein or the derived fusion proteins was determined in an ELISA. A soluble fraction containing 5 μg HBc or I(P)M2HBcm was analysed on a SDS 12.5% PAGE-gel (see FIG. 11). The same fractions were also analysed in a Western blot (see FIG. 12). The proteins of interest were detected with an antibody directed against the Hepatitis B core protein or with the monoclonal antibody specific for the extracellular part of the M2 protein. It can be concluded that the new fusion protein, IM2HBcm, is expressed as efficiently as IPM2HBcm. Moreover the amino acid change in the extracellular part of the M2 protein (Gly20-->Asp) has no effect on the binding of the monoclonal anti-M2 antibody.

8. Immunization Against Heterologous Challenge

A similar procedure as described in point 4 was used to test the efficiency of IPM2HBcm and IM2HBcm to protect mice versus heterologous challenge with influenza. 10 M1crograms of IPM2HBcm or IM2HBcm (purified in an identical way as IPM2HBcm) were used for immunization. The mice were challenged with 30 HAU X-47.

All mice immunized showed a significant degree of protection against the heterologous challenge. 8 (in case of IPM2HBcm, p<0.05) or 12 (in case of IM2HBcm, p<0.0001) mice out of 12 survived the influenza infection, versus only 2 out of 11 in the control group (FIG. 8C).

To test the effect of intranasal administration, the same procedure was followed, but instead of the intraperitoneal injection, the antigen was administered intranasally. Also in this case, the protection is evident: 12 (in case of IPM2HBcm, p<0.0001) or 11 (in case of IM2HBcm, p<0.001) mice out of 12 survived the influenza infection, versus 2 out of 11 in the control group (FIG. 8D).

9. Construction of Vectors for the Expression of M2-HBc Fusion Proteins in *L. Lactis*

The plasmid pTREX1 (Wells and Schofield, 1996) was used to express the Hepatitis B core protein and two M2-HBc fusion proteins, IPM2HBcm and IM2HBcm, in *Lactococcus*. This plasmid has a constitutive *L. lactis* chromosomal promoter, P1, which is followed by the translation initiation region of the *E. coli* bacteriophage T7 gene 10 (Wells and Schofield, 1996). The transcription terminator is derived from T7 RNA polymerase. The plasmid pTREX1 also carries two genes for resistance to erythromycin.

The expression plasmid, pTREX1, was cut with SphI, leaving a 3'CATG extension which was removed with Klenow DNA polymerase. The removed nucleotides were included in the sense linker for PCR amplification of the different genes. The linearized vector was then cut with BamHI and treated with CIP (calf intestine phosphatase, Boehringer, Mannheim, Germany).

The genes hbc, ipm2hbc and im2hbc were amplified by PCR (see Materials and methods). The anti-sense linker (HBca) was identical in all amplifications and provided a SpeI and a BclI site after the stop codon (see FIG. 13). For the amplification of ipm2hbc and im2hbc the same sense oligonucleotide (M2s) could be used, since the mutation Gly→Asp in the extracellular part of the M2 protein is located further downstream.

The amplification of hbc from pPLcA1 was only possible after the vector had been linearized with ScaI. The amplification reaction that produced a sufficient amount of fragment, under the most stringent conditions, was used for further cloning. The amplified fragment, hbc, ipm2hbc or im2hbc, was cut with BclI, phosphorylated with T4 polynucleotide kinase and inserted in the SphI and BamHI opened pTREX1 (see FIG. 14). The new plasmids were called pT1HBc, pT1PM2HBc (in which the extracellular part of the M2 protein is derived from the virus A/PR/8/34) and pT1M2HBc (in which the sequence of the extracellular part of the M2 protein corresponds to the type present in nearly all human influenza A viruses sequenced to date), respectively. The sequence of the inserted fragment was determined on a model 373A sequencer (Applied Biosystems, Foster City, Calif., USA) and shown to be correct.

In view of using *Lactococcus lactis* as an improved vaccine delivery vehicle, two murine cytokines, interleukin 2 (mIL2) and interleukin 6 (mIL6) were inserted as second cistrons in the same operon as the antigen. In that way we could obtain bacteria expressing the antigen, e.g. IM2HBcm, together with secreted murine interleukin 2 or 6. To obtain secretion of the interleukins into the growth medium, they were fused in frame to the lactococcal usp45 secretion signal peptide (van Asseldonk et al., 1990). The plasmids pT1HBc, pT1PM2HBc and pT1M2HBc were cut with SpeI and treated with CIP. The murine interleukin 2 gene was isolated as a 572 by XbaI-SpeI fragment from plasmid pL2MIL2 (Steidler et al., 1995). This fragment was inserted into the SpeI opened pT1HBc, pT1PM2HBc and pT1M2HBc giving rise to pT1HBcIL2, pT1PM2HBcIL2 and pT1M2HBcIL2, respectively.

In an analogous way the murine interleukin 6 gene was isolated as a 687 by XbaI-SpeI fragment from pL2MIL6 (Steidler et al., 1996) and inserted into the SpeI opened vectors, pT1HBc, pT1PM2HBc and pT1M2HBc, to create pT1HBcIL6, pT1PM2HBcIL6 and pT1M2HBcIL6, respectively.

10. Expression of HBc and M2HBc in *L. Lactis*

*Lactococcus* lactis strain MG1363 (Gasson, 1983) containing the plasmids for the expression of the antigen alone (pT1HBc, pT1PM2HBc and pT1M2HBc) or in combination with mouse interleukin 2 (pT1HBcIL2, pT1PM2HBcIL2 and pT1M2HBcIL2) or mouse interleukin 6 (pT1HBcIL6, pT1PM2HBcIL6 and pT1M2HBcIL6) were cultured as described in Materials and methods. MG1363 [pTREX1] was used as control.

An equivalent of $10^9$ bacteria was analysed by SDS 12.5% PAGE. The expression of the Hepatitis B core and the M2-HBc fusion proteins were analysed by Western immunoblotting (see FIG. 15) carried out as described in Materials and methods. The expression of IM2HBc in MG1363 [pT1M2HBcIL6] was not as high as in the other constructs. By screening different colonies a clone could be isolated with comparable expression levels.

The production and secretion of interleukins into the growth medium was analyzed in a biological assay. The biological activity of mIL2 was assayed by the proliferation of a T-cell line, CTLL2 (Gillis et al., 1978) as compared to a human IL2 standard. The biological activity of mIL6 was measured by the proliferation of a B-cell hybridoma, 7TD1 (Van Snick et al., 1986). Table 2 gives an overview of the level of interleukin 2 and 6 per ml culture medium produced by the different expression plasmids. The supernatant of cultures producing mIL6 did not lead to proliferation in a mIL2 assay and vice versa.

TABLE 2

| Plasmid | mIL2 production | mIL6 production |
| --- | --- | --- |
| pT1HBcIL2 | 410 ng/ml | — |
| pT1PM2HBcIL2 | 481 ng/ml | — |
| pT1M2HBcIL2 | 359 ng/ml | — |
| pT1HBcIL6 | — | 1020 ng/ml |
| pT1PM2HBcIL6 | — | 772 ng/ml |
| pT1M2HBcIL6 | — | 802 ng/ml |

11. Adaptation of the Coding Sequence of M2e to Expression in *L. Lactis*

Since the two fusion proteins, IPM2HBcm and IM2HBcm could hardly be detected in a Western blot, we tried to augment the production of these two fusion proteins by adapting the codon usage of the extracellular part of the M2 protein to *L. lactis* (van de Guchte et al., 1992).

At the 5' end of the extracellular part of the M2 protein we observed two consecutive leucine codons (CUG CUG) that were optimal for expression in *E coli* (68%), but poor for translation in *L. lactis* (8%, percentages described in van de Guchte et al., 1992). Therefore these codons were changed to UUA. The genes for ipm2hbc and im2hbc were amplified by PCR from respectively pPLcIPM2HBcm or pPLcIM2HBcm, with a new sense primer, M2Ls, containing the two changed leucine codons (see FIG. 13). As anti-sense primer we used again HBca (see FIG. 13). The cloning of the genes was analogous as depicted in FIG. 14. The vectors so created were called pT1PM2LHBc and pT1M2LHBc.

The expression level of the mutated M2HBc proteins, compared to the original fusion proteins, was analyzed in a Western blot (see FIG. 16). The expression level of the M2HBc fusion proteins with the *L. lactis* adapted leucine codons, was indeed much higher. It is concluded that the adaptation of codon usage to the *L. lactis* translation machinery, has a positive effect on the level of protein produced. In a similar way as described above, the murine interleukin 6 gene was inserted into pT1PM2LHBc and pT1M2LHBc, giving rise to pT1PM2LHBcIL6 and pT1M2LHBcIL6, respectively.

12. Construction of M2C3d in *Lactococcus Lactis*

A second carrier protein, C3d, is also an attractive molecule for the presentation of the extracellular part of the M2 protein. Dempsey et al. (1996) demonstrated that the attachment of an antigen to three consecutive C3d molecules, was much more efficient in producing a high antibody response than the antigen administered in complete Freund's adjuvant.

The universal sequence of the extracellular part of the M2 protein, with the adapted leucine codons, is used for making a fusion to the amino-terminus of the first C3d molecule. The coding sequence for three different fusion proteins are constructed. In the first situation the M2C3d3 fusion protein is expressed in the cytoplasm of *L. lactis* (cM2C3d3), similar to the M2HBc fusion proteins. In the second case the M2C3d3 protein is secreted into the growth medium by making an in frame fusion to the usp45-signal sequence (sM2C3d3) and the last construct, which is a derivative of the secreted form, contains in addition an anchor sequence (spaX) after the last C3d molecule to attach the fusion protein covalently in the cell wall (sM2C3d3X).

The amplified C3d3 fragment was first subcloned in a derivative of pUC18, namely pUCB/S. pUC18 was linearized with HindIII and a BglII linker was inserted. The resulting plasmid was then opened with SmaI and a SpeI linker was inserted, resulting in the plasmid pUCB/S (see FIG. 18). Three succeeding copies of C3d were amplified from pSG5.C3d3.YL (a gift from Dr. D. Fearon) by PCR with the oligonucleotides C3ds and C3da (see FIG. 17). This amplified fragment was cut with BglII and SpeI. The resulting 2830 bp BglII-SpeI fragment was cloned into the BglII and SpeI opened vector pUCB/S (see FIG. 18). The genes cm2 and sm2 were amplified by PCR. For the amplification of cm2 we used the sense oligonucleotide M2Ls (see FIG. 13) and the anti-sense linker M2Ca, which carried for our purposes a BamHI site in the correct reading frame (see FIG. 17). The same anti-sense linker was used for the amplification of sm2. The sense oligonucleotide for the amplification of sm2, M2LSs, started at the first codon of the mature M2 protein.

For the synthesis of the cytoplasmic form of M2C3d3, the information coding for the extracellular part of the M2 protein was inserted into pTREX1 analogous as the m2hbc gene described above (see also FIG. 18). The amplified cm2 fragment was cut with BamH I (77 bp), phosphorylated with T4 polynucleotide kinase and inserted in the Sph I and BamH I opened pTREX1, creating pT1cM2L. For the synthesis of the secreted and anchored form of M2C3d3, the information coding for the extracellular part of the M2 protein was inserted into pT1NX. The vector pT1NX carries the usp45-signalsequence (usp45-ss) and the anchor sequence derived from *Staphylococcus aureus* protein A (spaX). The plasmid pT1NX was cut with Nae I, correctly positioned at the end of the usp45-ss and BamH I. The amplified fragment, sm2, was cut with BamH I and phosphorylated with T4 polynucleotide kinase. This 73 by sm2 fragment was inserted into the Nae I and BamH I opened pT1NX, resulting in the plasmid pT1sM2LX (see FIG. 18). One single C3d fragment, isolated from pUCC3d, can then be inserted into the BamH I site at the end of the cm2 or sm2 sequence. Afterwards one or two additional C3d copies will be inserted.

13. Construction of M2TTFC in *Lactococcus lactis*

A third carrier protein, tetanus toxin fragment C (TTFC), can also be used. TTFC has already been expressed in *L. lactis* under control of the P1 promoter, pT1TT (Wells and Schofield, 1996). L. lactis expressing TTFC in combination with mIL2 or mIL6 to raise the antibody production, was successfully used in immunization experiments (Patent GB 9521568.7). As positive control for analysis of antibody response in the present immunization experiments with *L. lactis* expressing I(P)M2HBcm, a fusion was made between the extracellular part of the M2 protein and the amino terminus of TTFC.

The ttfc gene was amplified by PCR (see Materials and Methods) from pT1TT. The sense oligonucleotide (TTFCs) provided a BamH I site, positioned in the correct reading frame, before the second codon of ttfc, corresponding to threonine. The anti-sense linker (TTFCa) provided a Spe I and a BamH I site after the stop codon (see FIG. 19). The amplification reaction that produced a sufficient amount of fragment, under the most stringent conditions, was used for further cloning (see Materials and Methods). The amplified ttfc fragment was cut with BamH I, phosphorylated with T4 polynucleotide kinase and inserted in the Bcl I opened pATIPM2 ml (see FIG. 20). This plasmid construct was called pATIPM2TT. From this plasmid the m2ttfc gene was amplified by PCR (see Materials and methods) with M2Ls and TTFCa (see FIG. 19). The amplified m2ttfc fragment was cut with BamH I, phosphorylated with T4 polynucleotide kinase and inserted in the Sph I and BamH I opened pTREX1 (see FIG. 20). The new plasmid was called, pT1PM2LTT. In this construct the extracellular part of the M2 protein is derived from the virus A/PR/8/34, with the two leucine codons adapted for use in *L. lactis*. The sequence of the inserted fragment was determined on a model 373A sequencer (Applied Biosystems, Foster City, Calif., USA) and shown to be correct.

The murine interleukin genes, mIL2 and mIL6, were inserted in the same operon as m2ttfc. The murine interleukin 2 gene was isolated as a 572 by Xba I—Spe I fragment from plasmid pL2MIL2 (Steidler et al., 1995). This fragment was inserted into the Spe I opened pT1PM2LTT giving rise to pT1PM2LTTIL2 (see FIG. 20). In an analogous way the murine interleukin 6 gene was isolated as a 687 by Xba I—Spe I fragment from pL2MIL6 (Steidler et al., 1996) and inserted into the Spe I opened vector pT1PM2LTT to create pT1PM2LTTIL6 (see FIG. 20).

14. Expression of TTFC and M2TTFC in *L. Lactis*

*Lactococcus lactis* strain MG1363 (Gasson, 1983) containing the plasmids for the expression of the antigen alone (pT1PM2LTT) or in combination with mouse interleukin 2 (pT1PM2LTTIL2) or mouse interleukin 6 (pT1PM2LTTIL6) were cultured as described in Materials and methods. MG1363 [pT1TT] was used as a control.

An equivalent of $10^9$ bacteria was analyzed by SDS 10% PAGE. The expression of the IPM2TTFC fusion protein was analyzed by Western immunoblotting (see FIG. 21) carried out as described in Materials and methods.

The production and secretion of interleukins into the growth medium was analyzed by a biological assay. *L. lactis* [pT1PM2LTTIL2] produced about 500 ng/ml mIL2 and *L. lactis* [pT1PM2LTTIL6] about 1 pg/ml mIL6. These results are comparable with the expression levels obtained with I(P)M2HBcm in combination with the two interleukins.

Discussion

The present example describes several systems for the presentation of the highly conserved extracellular part of the influenza A virus M2 protein to the immune system. The M2 fragment was fused to the amino terminus of the carrier protein in order to retain a free N-terminus of the M2-domain and in this way mimic the wild type structure of the M2 protein. The first fusion protein, M2 linked to human $\beta_2$-microglobulin (IPM2hB2Mm), was used to produce monoclonal antibodies. A second fusion protein, M2 linked to Hepatitis B core protein (IPM2HBcm) was used for vaccination studies. Both proteins could also be used in the detection of a specific antibody response against the extracellular part of the M2 protein, since a correction has to be made for antibodies directed against the carrier protein, which are also produced during the immunization process.

The vaccination studies with IPM2HBcm showed that the administered dose in the range that was used, was apparently not a very critical parameter for obtaining protection, as a dose ranging from 5 to 50 µg protected the mice, although the immunized mice still showed a high morbidity. This may have been due to the high dose of virus (5 $LD_{50}$) that was used for the challenge in order to obtain a clear-cut result for the degree of protection. In a natural influenza infection the number of infecting virus particles is much lower, so that it can be assumed that the morbidity would decrease accordingly.

Analysis of the serum of immunized mice showed a substantial antibody response towards the extracellular part of the M2 protein, especially after viral challenge. This latter, high response can be due to another way of administration, intraperitoneal versus intranasal. Or it can be explained on the basis of a more complete defense mechanism against the incoming virus.

Slepushkin et al. (1995) described a vaccination strategy, based on a membrane extract containing the natural complete M2 protein for homologous and heterologous virus challenge. But they used a very strong adjuvant, incomplete Freund's, which is not appropriate for medical use.

In contrast, the M2 extracellular domain fusions of the invention described here can be obtained in a pure form (at least 95% purity), and can be administered in combination with safe adjuvants. A high degree of protection was obtained, despite the fact that the challenge was fairly severe. In view of the almost invariant sequence of the M2 extracellular domain (see table 1 which shows an overview of the amino acid sequences of the extracellular domain of the influenza A M2 protein) it may be expected that the protection achieved will be similar against all human influenza A strains known so far.

The vaccine may be further improved by the inclusion of an influenza specific T helper epitope as well as a CTL epitope into the fusion protein, for example internally or linked to the C-terminus of the Hepatitis B core protein. Other immunization routes are possible as well, for example intraperitoneal versus intranasal.

Besides the gram negative organism, *E. coli*, also *L. lactis* was used, a gram positive organism, for the expression of the M2HBcm fusion proteins. In *L. lactis* it is not necessary to purify the expressed fusion protein. The bacteria can be administered directly either intranasally or orally.

A third promising carrier protein is also described, namely the third complement protein fragment d (C3d) (Dempsey et al., 1996). In a preferred construction, three copies of the C3d protein are preceded by the extracellular domain of the M2 protein. This M2C3d3 fusion protein can be expressed either intracellular, anchored in the cell wall or secreted into the growth medium by genetic fusion to appropriate regulatory sequences.

REFERENCES

Allen et al. (1980) Virology 107, 548-551
Baez et al. (1980) J. Infect. dis. 141, 362-365
Belshe et al. (1988) J. Virol. 62, 1508-1512
Birnboim and Doly (1979) N.A.R. 7, 1513-1523
Borisova et al. (1989) FEBS Lett. 259, 121-124
Casadaban and Cohen (1980) J. Mol. Biol. 0.138, 179-207
Clarke et al. (1987) Nature 330, 381-384
Cohen and Richmond (1982) Nature 296, 677-678
Cox et al. (1988) Virology 167, 554-567
Dempsey et al. (1996) Science 271, 348-350
Deng and Nickolov (1992) Anal. Biochem. 200, 81-88
Gasson (1983) J. Bact. 154, 1-9
Gillis et al. (1978) J. Immunol. 120, 2027-2032
Hirst (1941) Science 94, 22-23
Holsinger and Lamb (1991) Virology 183, 32-43
Kahn et al. (1979) Methods Enzymol. 68, 268-280
Kendal et al. (1982) Concepts and procedures for laboratory-based influenza surveillance. p. B7-Bl 2, Bl 7-Bl 9
Klimov et al. (1992) Virology 186, 795-797
Köhler and Milstein (1975) Nature 256, 495-497
Laemmli (1970) Nature 227, 680-685
Lamb and Lai (1981) Virology 112, 746-751
Lamb et al. (1981) Proc. Natl. Acad. Sci. USA 78, 4170-4174
Lamb et al. (1985) Cell 40, 627-633
Levi and Amon (1996) Vaccine 14, 85-92
Markushin et al. (1988) Virus Res. 10, 263-272
Miller (1972) Experiments in Molecular Genetics. Cold Spring Harbor Laboratory Press, Cold Spring Harbor, N.Y., p. 431
Min Jou et al. (1980) Cell 19, 683-696
Nakamaye and Eckstein (1986) N.A.R. 14, 9679-9698
Nassal (1988) Gene 66, 279-294
Neu and Heppel (1965) J. Biol. Chem. 240, 3685-3692
Ortin et al. (1983) Gene 23, 233-239
Parker and Wiley (1989) Gene 83, 117-124
Remaut et al. (1981) Gene 15, 81-93
Remaut et al. (1983a) N.A.R. 11, 4677-4688
Remaut et al. (1983b) Gene 22, 103-113
Schader et al. (1992) J. Virol. 66, 106-114
Slepushkin et al. (1995) Vaccine 13, 1399-1402
Stanssens et al. (1989) N.A. R. 17, 4441-4454
Steidler et al. (1994) Biotechn. Bioeng. 44, 1074
Steidler et al. (1995) Appl. Environ. Microbiol. 61, 1627-1629
Steidler et al. (1996) NATO ASI Series H 98 p 63-79. eds. Bozoglu, T. F. and Ray, B. Springer, Berlin
Struhl (1985) Biotechniques 3, 452-453
Sugrue et al. (1990) Virology 179, 51-56
Sugrue and Hay (1991) Virology 180, 617-624
Treanor et al. (1990) J. Virol. 64, 1375-1377
van Asseldonk et al. (1990) Gene 95, 155-160
van de Guchte et al. (1992) FEMS Microbiol. Rev. 88, 73-92
Van Snick et al. (1986) Proc. Natl. Acad. Sci. USA 83, 9679

Vogelstein and Gillespie (1979) Proc. Natl. Acad. Sci. USA 76, 615-619
Wells et al. (1993) J. Appl. Bact. 74, 629-636
Wells and Schofield (1996) NATO ASi Series H 98 p 37-62. eds. Bozoglu, T. F. and Ray, B. Springer, Berlin
Winter and Fields (1980) N.A.R. 8, 1965-1974
Zebedee and Lamb (1988) J. Virol. 62, 2762-2772
Zebedee and Lamb (1989) N.A.R. 17, 2870
Zell and Fritz (1987) EMBO J. 6, 1809-1815

The invention claimed is:

1. A human influenza immunogenic composition comprising a fusion product, said fusion product comprising
   (i) an antigen comprising an immunogenic extracellular part of an M2 membrane protein of a human influenza A virus, wherein said extracellular immunogenic part consists of SEQ ID NOs: 1, 2, or 3, or an immunogenic fragment thereof that induces antibodies to human influenza A virus, and
   (ii) a presenting carrier.

2. The composition of claim 1, wherein the presenting carrier is heterologous peptide or polypeptide.

3. The composition of claim 2, wherein the heterologous peptide or polypeptide is selected from the group consisting of a hepatitis B core protein, C3d, a polypeptide comprising multiple copies of C3d, tetanus toxin fragment C and yeast Ty particles.

4. The composition of claim 1, wherein the presenting carrier is a non-peptidic structure.

5. The composition of claim 4, wherein the presenting non-peptidic structure is selected from the group consisting of glycans, polyethylene glycols, peptide mimetics, and synthetic polymers.

6. The composition of claim 1, wherein the presenting carrier enhances the immunogenicity of the antigen.

7. The composition of claim 6, wherein the presenting carrier comprises an epitope recognized by an influenza-specific T helper cell or cytotoxic T cell.

8. The composition of claim 1, wherein the composition comprises *Lactococci* cells expressing said fusion product in or on their cell membrane, and said cells can release said fusion product.

9. The composition of claim 1, wherein the fusion product is in an isolated form.

10. The composition of claim 1, wherein the fusion product is anchored in the membrane of an acceptor cell expressing the fusion product.

11. The composition of claim 1, wherein the fusion product is part of a lipid bilayer or cell wall.

12. The composition of claim 1, wherein the composition comprises *Lactococci* cells expressing said fusion product in or on their cell wall.

13. The composition of claim 1, further comprising an influenza antigen selected from the group consisting of hemagglutinin, neuraminidase, nucleoprotein and native M2.

14. A method of obtaining a human influenza immunogenic composition, comprising
   providing a fusion product, said fusion product comprising
      (i) an antigen comprising an immunogenic extracellular part of an M2 membrane protein of a human influenza A virus, wherein said extracellular immunogenic part consists of SEQ ID NOs: 1, 2, or 3, or an immunogenic fragment thereof that induces antibodies to human influenza A virus, and
      (ii) a presenting carrier; and mixing said fusion product with an excipient.

15. The method according to claim 14, wherein the presenting carrier is heterologous peptide or polypeptide.

16. The method according to claim 14, wherein the heterologous peptide or polypeptide is selected from the group consisting of a hepatitis B core protein, C3d, a polypeptide comprising multiple copies of C3d, tetanus toxin fragment C and yeast Ty particles.

17. The method according to claim 14, wherein the presenting carrier is a non-peptidic structure.

18. The method according to claim 14, wherein the presenting non-peptidic structure is selected from the group consisting of glycans, polyethylene glycols, peptide mimetics, and synthetic polymers.

19. A human influenza immunogenic composition obtained by the following steps:
   providing a nucleic acid construct that encodes a fusion product, said fusion product comprising (i) an antigen comprising an immunogenic extracellular part of an M2 membrane protein of a human influenza A virus, wherein said extracellular immunogenic part consists of SEQ ID NOs: 1, 2, or 3, or an immunogenic fragment thereof that induces antibodies to human influenza A virus, and (ii) a heterologous peptide or polypeptide presenting carrier;
   introducing the nucleic acid construct into an acceptor cell form a transformed acceptor cell;
   culturing the transformed acceptor cell in a culture medium under conditions that permit expression of the fusion product; and
   optionally isolating the fusion product from the acceptor cell or its culture medium; and
   optionally admixing the fusion product with an excipient, thereby obtaining a human influenza immunogenic composition.

20. The influenza immunogenic composition of claim 19, wherein the heterologous peptide or polypeptide is selected from the group consisting of a hepatitis B core protein, C3d, a polypeptide comprising multiple copies of C3d, tetanus toxin fragment C and yeast Ty particles.

21. The influenza immunogenic composition of claim 20, wherein the influenza immunogenic composition comprises a cytokine.

22. The influenza immunogenic composition of claim 20, wherein the influenza immunogenic composition comprises a vaccine adjuvant that is not Freund's adjuvant.

23. An influenza immunogenic composition for an animal species comprising a fusion product, said fusion product comprising
   (i) an antigen comprising an immunogenic extracellular part of an M2 membrane protein of an influenza A virus, wherein said extracellular immunogenic part consists of SEQ ID NOs: 1, 2, or 3, or an immunogenic fragment thereof that induces antibodies to human influenza A virus; and
   (ii) a presenting carrier.

24. The composition of claim 23, wherein the presenting carrier is heterologous peptide or polypeptide.

25. The composition of claim 24, wherein the heterologous peptide or polypeptide is selected from the group consisting of a hepatitis B core protein, C3d, a polypeptide comprising multiple copies of C3d, tetanus toxin fragment C and yeast Ty particles.

26. The composition of claim 24, wherein the presenting carrier is a non-peptidic structure.

27. The composition of claim 25, wherein the presenting non-peptidic structure is selected from the group consisting of glycans, polyethylene glycols, peptide mimetics, and synthetic polymers.

28. A human influenza immunogenic composition comprising a fusion polypeptide, said fusion polypeptide comprising
   (i) an antigen comprising an immunogenic extracellular part of an M2 membrane protein of an influenza A virus, wherein said extracellular immunogenic part consists of SEQ ID NOs: 1, 2, or 3, or an immunogenic fragment thereof that induces antibodies to human influenza A virus; and
   (ii) a heterologous peptide or polypeptide presenting carrier,
   said fusion polypeptide being the expression product of a gene construct comprising a coding sequence for said antigen of (i) linked to a coding sequence for said presenting carrier of (ii).

29. The influenza immunogenic composition of claim 28, wherein said heterologous peptide or polypeptide presenting carrier is selected from the group consisting of a hepatitis B core protein, C3d, a polypeptide comprising multiple copies of C3d, and tetanus toxin fragment C.

30. The influenza immunogenic composition of claim 20, wherein said heterologous peptide or polypeptide presenting carrier is the hepatitis B core protein.

* * * * *

SEQUENCE LISTING

```
<160> NUMBER OF SEQ ID NOS: 43

<210> SEQ ID NO 1
<211> LENGTH: 23
<212> TYPE: PRT
<213> ORGANISM: Influenza virus

<400> SEQUENCE: 1

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 2
<211> LENGTH: 23
<212> TYPE: PRT
<213> ORGANISM: Influenza virus

<400> SEQUENCE: 2

Ser Leu Leu Thr Glu Val Glu Thr Pro Ile Arg Asn Glu Trp Gly Cys
1               5                   10                  15

Arg Cys Asn Gly Ser Ser Asp
            20

<210> SEQ ID NO 3
<211> LENGTH: 23
<212> TYPE: PRT
<213> ORGANISM: Influenza virus

<400> SEQUENCE: 3

Ser Leu Leu Thr Glu Val Glu Thr Pro Thr Lys Asn Glu Trp Glu Cys
1               5                   10                  15

Arg Cys Asn Asp Ser Ser Asp
            20

<210> SEQ ID NO 4
<211> LENGTH: 24
<212> TYPE: DNA
<213> ORGANISM: Artificial sequence
<220> FEATURE:
<223> OTHER INFORMATION: synthetic sequence

<400> SEQUENCE: 4
tttactgttt tcgtaacagt tttg                                          24

<210> SEQ ID NO 5
<211> LENGTH: 20
<212> TYPE: DNA
<213> ORGANISM: Artificial sequence
<220> FEATURE:
<223> OTHER INFORMATION: synthetic sequence

<400> SEQUENCE: 5
caacaacgca cagaatctag                                               20

<210> SEQ ID NO 6
<211> LENGTH: 30
```

```
<212> TYPE: DNA
<213> ORGANISM: Artificial sequence
<220> FEATURE:
<223> OTHER INFORMATION: synthetic sequence

<400> SEQUENCE: 6
gatccgtctc tgctgaccga agttgaaacc                                              30

<210> SEQ ID NO 7
<211> LENGTH: 26
<212> TYPE: DNA
<213> ORGANISM: Artificial sequence
<220> FEATURE:
<223> OTHER INFORMATION: synthetic sequence

<400> SEQUENCE: 7
gcagagacga ctggcttcaa ctttgg                                                  26

<210> SEQ ID NO 8
<211> LENGTH: 21
<212> TYPE: DNA
<213> ORGANISM: Artificial sequence
<220> FEATURE:
<223> OTHER INFORMATION: synthetic sequence

<400> SEQUENCE: 8
cggttcaagt gatcatctcg c                                                       21

<210> SEQ ID NO 9
<211> LENGTH: 69
<212> TYPE: DNA
<213> ORGANISM: Influenza virus

<400> SEQUENCE: 9
tctctgctga ccgaagttga aacccctatc agaaacgaat gggggtgcag atgcaacggt            60
tcaagtgat                                                                    69

<210> SEQ ID NO 10
<211> LENGTH: 23
<212> TYPE: PRT
<213> ORGANISM: Influenza virus

<400> SEQUENCE: 10

Ser Leu Leu Thr Glu Val Glu Thr Pro Ile Arg Asn Glu Trp Gly Cys
1               5                   10                  15

Arg Cys Asn Gly Ser Ser Asp
            20

<210> SEQ ID NO 11
<211> LENGTH: 17
<212> TYPE: DNA
<213> ORGANISM: Artificial sequence
<220> FEATURE:
<223> OTHER INFORMATION: synthetic sequence

<400> SEQUENCE: 11
gcgcaggcct tccagcg                                                            17

<210> SEQ ID NO 12
<211> LENGTH: 23
<212> TYPE: DNA
<213> ORGANISM: Artificial sequence
<220> FEATURE:
<223> OTHER INFORMATION: synthetic sequence

<400> SEQUENCE: 12
```
gcgcaggccc tgcagcgtac tcc                                              23

<210> SEQ ID NO 13
<211> LENGTH: 16
<212> TYPE: DNA
<213> ORGANISM: Artificial sequence
<220> FEATURE:
<223> OTHER INFORMATION: synthetic sequence

<400> SEQUENCE: 13
cctcagatct tctgca                                                      16

<210> SEQ ID NO 14
<211> LENGTH: 12
<212> TYPE: DNA
<213> ORGANISM: Artificial sequence
<220> FEATURE:
<223> OTHER INFORMATION: synthetic sequence

<400> SEQUENCE: 14
ggagtctaga ag                                                          12

<210> SEQ ID NO 15
<211> LENGTH: 27
<212> TYPE: DNA
<213> ORGANISM: Artificial sequence
<220> FEATURE:
<223> OTHER INFORMATION: synthetic sequence

<400> SEQUENCE: 15
ccgtagcgca ggcctctctg ctgaccg                                          27

<210> SEQ ID NO 16
<211> LENGTH: 17
<212> TYPE: DNA
<213> ORGANISM: Artificial sequence
<220> FEATURE:
<223> OTHER INFORMATION: synthetic sequence

<400> SEQUENCE: 16
ggatccatat ccatggc                                                     17

<210> SEQ ID NO 17
<211> LENGTH: 25
<212> TYPE: DNA
<213> ORGANISM: Artificial sequence
<220> FEATURE:
<223> OTHER INFORMATION: synthetic sequence

<400> SEQUENCE: 17
cggtcagcag agacatgggt aatcc                                            25

<210> SEQ ID NO 18
<211> LENGTH: 26
<212> TYPE: DNA
<213> ORGANISM: Artificial sequence
<220> FEATURE:
<223> OTHER INFORMATION: synthetic sequence

<400> SEQUENCE: 18
ccagaccgtt cagctggata ttacgg                                           26

<210> SEQ ID NO 19
<211> LENGTH: 24
<212> TYPE: DNA
<213> ORGANISM: Influenza virus

```
<400> SEQUENCE: 19
atgtctctgc tgaccgaagt tgaa                                          24

<210> SEQ ID NO 20
<211> LENGTH: 8
<212> TYPE: PRT
<213> ORGANISM: Inlfuenza virus

<400> SEQUENCE: 20

Met Ser Leu Leu Thr Glu Val Glu
1               5

<210> SEQ ID NO 21
<211> LENGTH: 7
<212> TYPE: PRT
<213> ORGANISM: Artificial sequence
<220> FEATURE:
<223> OTHER INFORMATION: synthetic sequence

<400> SEQUENCE: 21

Ser Leu Leu Thr Glu Val Glu
1               5

<210> SEQ ID NO 22
<211> LENGTH: 29
<212> TYPE: DNA
<213> ORGANISM: Artificial sequence
<220> FEATURE:
<223> OTHER INFORMATION: synthetic sequence

<400> SEQUENCE: 22
ggatcacttg aatcgttaca tctgcaccc                                     29

<210> SEQ ID NO 23
<211> LENGTH: 26
<212> TYPE: DNA
<213> ORGANISM: Artificial sequence
<220> FEATURE:
<223> OTHER INFORMATION: synthetic sequence

<400> SEQUENCE: 23
ccagaccgtt cagctggata ttacgg                                        26

<210> SEQ ID NO 24
<211> LENGTH: 27
<212> TYPE: DNA
<213> ORGANISM: Artificial sequence
<220> FEATURE:
<223> OTHER INFORMATION: synthetic sequence

<400> SEQUENCE: 24
catggatatg gatccttata aagaatt                                       27

<210> SEQ ID NO 25
<211> LENGTH: 23
<212> TYPE: DNA
<213> ORGANISM: Artificial sequence
<220> FEATURE:
<223> OTHER INFORMATION: synthetic sequence

<400> SEQUENCE: 25
catgtctctg ctgaccgaag ttg                                           23

<210> SEQ ID NO 26
<211> LENGTH: 29
```

```
<212> TYPE: DNA
<213> ORGANISM: Artificial sequence
<220> FEATURE:
<223> OTHER INFORMATION: synthetic sequence

<400> SEQUENCE: 26
catgtcttta ttaaccgaag ttgaaaccc                                       29

<210> SEQ ID NO 27
<211> LENGTH: 39
<212> TYPE: DNA
<213> ORGANISM: Artificial sequence
<220> FEATURE:
<223> OTHER INFORMATION: synthetic sequence

<400> SEQUENCE: 27
cgtgatcaac tagttcacta acattgagat tcccgagat                            39

<210> SEQ ID NO 28
<211> LENGTH: 33
<212> TYPE: DNA
<213> ORGANISM: Artificial sequence
<220> FEATURE:
<223> OTHER INFORMATION: synthetic sequence

<400> SEQUENCE: 28
cgggatcccc acttgaatcg ttacatctgc acc                                  33

<210> SEQ ID NO 29
<211> LENGTH: 30
<212> TYPE: DNA
<213> ORGANISM: Artificial sequence
<220> FEATURE:
<223> OTHER INFORMATION: synthetic sequence

<400> SEQUENCE: 29
tctttattaa ccgaagttga aaccctatc                                       30

<210> SEQ ID NO 30
<211> LENGTH: 35
<212> TYPE: DNA
<213> ORGANISM: Artificial sequence
<220> FEATURE:
<223> OTHER INFORMATION: synthetic sequence

<400> SEQUENCE: 30
ccgcgcccac ccgacgagat ctcggatcta ccccc                                35

<210> SEQ ID NO 31
<211> LENGTH: 38
<212> TYPE: DNA
<213> ORGANISM: Artificial sequence
<220> FEATURE:
<223> OTHER INFORMATION: synthetic sequence

<400> SEQUENCE: 31
gcactagttc aaggatccga tccgaactct tcagatcc                             38

<210> SEQ ID NO 32
<211> LENGTH: 35
<212> TYPE: DNA
<213> ORGANISM: Artificial sequence
<220> FEATURE:
<223> OTHER INFORMATION: synthetic sequence

<400> SEQUENCE: 32
cgggatccga caccaattcc attttcttat tctaa                                35
```

<210> SEQ ID NO 33
<211> LENGTH: 25
<212> TYPE: DNA
<213> ORGANISM: Artificial sequence
<220> FEATURE:
<223> OTHER INFORMATION: synthetic sequence

<400> SEQUENCE: 33
ggggatccac tagtttaatc atttg                                    25

<210> SEQ ID NO 34
<211> LENGTH: 29
<212> TYPE: DNA
<213> ORGANISM: Artificial sequence
<220> FEATURE:
<223> OTHER INFORMATION: synthetic sequence

<400> SEQUENCE: 34
catgtcttta ttaaccgaag ttgaaaccc                                29

<210> SEQ ID NO 35
<211> LENGTH: 25
<212> TYPE: DNA
<213> ORGANISM: Artificial sequence
<220> FEATURE:
<223> OTHER INFORMATION: synthetic sequence

<400> SEQUENCE: 35
gctactagta aatcagtcac accaa                                    25

<210> SEQ ID NO 36
<211> LENGTH: 33
<212> TYPE: DNA
<213> ORGANISM: Artificial sequence
<220> FEATURE:
<223> OTHER INFORMATION: synthetic sequence

<400> SEQUENCE: 36
cgaagcttgc cggcaaaggc agaatgcgcc gcc                           33

<210> SEQ ID NO 37
<211> LENGTH: 23
<212> TYPE: DNA
<213> ORGANISM: Artificial sequence
<220> FEATURE:
<223> OTHER INFORMATION: synthetic sequence

<400> SEQUENCE: 37
tctctgctga ccgaagttga aac                                      23

<210> SEQ ID NO 38
<211> LENGTH: 50
<212> TYPE: DNA
<213> ORGANISM: Artificial sequence
<220> FEATURE:
<223> OTHER INFORMATION: synthetic sequence

<400> SEQUENCE: 38
cgaagcttac tagttcacgg atccccactt gaatcgttgc atctgcaccc          50

<210> SEQ ID NO 39
<211> LENGTH: 18
<212> TYPE: DNA
<213> ORGANISM: Artificial sequence
<220> FEATURE:
<223> OTHER INFORMATION: synthetic sequence

```
<400> SEQUENCE: 39
ggtagatatt gaaagatg                                                    18

<210> SEQ ID NO 40
<211> LENGTH: 33
<212> TYPE: DNA
<213> ORGANISM: Artificial sequence
<220> FEATURE:
<223> OTHER INFORMATION: synthetic sequence

<400> SEQUENCE: 40
cgtctagatt actccagctc tatgctgaca aaa                                   33

<210> SEQ ID NO 41
<211> LENGTH: 57
<212> TYPE: DNA
<213> ORGANISM: Artificial sequence
<220> FEATURE:
<223> OTHER INFORMATION: synthetic sequence

<400> SEQUENCE: 41
cgagatctat gagtcttcta accgaggtcg aaacgcctat cagaaacgaa tgggggt         57

<210> SEQ ID NO 42
<211> LENGTH: 29
<212> TYPE: DNA
<213> ORGANISM: Artificial sequence
<220> FEATURE:
<223> OTHER INFORMATION: synthetic sequence

<400> SEQUENCE: 42
catgtcttta ttaaccgaag ttgaaaccc                                        29

<210> SEQ ID NO 43
<211> LENGTH: 38
<212> TYPE: DNA
<213> ORGANISM: Artificial sequence
<220> FEATURE:
<223> OTHER INFORMATION: synthetic sequence

<400> SEQUENCE: 43
cgtgatcaac tagttcacta acattgagat cccgagat                              38
```